(12) United States Patent
Filla et al.

(10) Patent No.: US 6,953,805 B2
(45) Date of Patent: Oct. 11, 2005

(54) EXCITATORY AMINO ACID RECEPTOR ANTAGONISTS

(75) Inventors: Sandra Ann Filla, Ashland, MA (US); Kevin John Hudziak, Indianapolis, IN (US); Brian Michael Mathes, Indianapolis, IN (US); Paul Leslie Ornstein, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 72 days.

(21) Appl. No.: 10/451,819

(22) PCT Filed: Dec. 20, 2001

(86) PCT No.: PCT/US01/44714

§ 371 (c)(1),
(2), (4) Date: Jun. 25, 2003

(87) PCT Pub. No.: WO02/053555

PCT Pub. Date: Jul. 11, 2002

(65) Prior Publication Data

US 2005/0170999 A1 Aug. 4, 2005

Related U.S. Application Data

(60) Provisional application No. 60/259,921, filed on Jan. 5, 2001.

(51) Int. Cl.$^7$ ...................... C07D 401/04; A61K 31/47
(52) U.S. Cl. ........................ 514/307; 546/307
(58) Field of Search ........................ 546/147; 514/307

(56) References Cited

U.S. PATENT DOCUMENTS

| | | | |
|---|---|---|---|
| 5,356,902 A | 10/1994 | Ornstein | |
| 5,446,051 A | 8/1995 | Ornstein | |
| 5,670,516 A | 9/1997 | Arnold et al. | |
| 5,767,117 A | 6/1998 | Moskowitz | |
| 6,579,886 B2 | 5/2003 | Bleakman et al. | |
| 6,566,370 B1 | 6/2003 | Bell et al. | |

FOREIGN PATENT DOCUMENTS

| | | |
|---|---|---|
| EP | 0 590 789 | 4/1994 |
| WO | WO 98/45270 | 10/1998 |
| WO | WO 01/01972 | 1/2001 |
| WO | WO 01/02367 | 1/2001 |

OTHER PUBLICATIONS

Neuroparmacoligy, 37, pp. 25–36 (1998), "Kainate GluR5 receptor subtype mediates the nociceptive response to formalin in the rat".

Neuropharmacology, 37, pp. 1211–1222 (1998), "Decahydroisoquinolines: novel competitive AMPA/kainite antagonists with neuroprotective effects in global cerebral ischaemia".

Y. Sahara, et al., "Glutamate Receptor Subunits GluR5 and KA–2 Are Coexpressed in Rat Trigeminal Ganglion Neurons," The Journal of Neuroscience, vol. 17, No. 17, pp. 6611–6620 (1997).

Z. Alam, et al., "Plasma levels of neuroexcitatory amino acids in patients with migraine or tension headache," Journal of Neurological Sciences, vol. 156, pp. 102–106 (1998).

Procter, et al., "Possible role of Glu54 glutamate receptors in spinal nociceptive processing in the anaesthetized rat," Journal of Physiology, 504.P, 101P–102P (1997).

Nikam, et al., The search for AMPA/Gly(N) receptor antagonists: Drugs of the Future, vol. 24, No. 10, pp. 1107–1124 (1999).

Proctor, et al., "Actions of kainite and AMPA selective glutamate receptor ligands on nociceptive processing in the spinal cord," Neuropharmacology, vol. 37, pp. 1287–1297 (1998).

Bleakman, et al., "Kainate receptor pharmacology and physiology," Cellular and Molecular Life Sciences, 56/7–8 (1999) 558–556.

National Library of Medicine (NLM), Bethesda, MD, US: Mitsilostas, et al., "Non–NMDA glutamate receptors modulate capsaicin induced c–fos expression within trigeminal nucleus caudalis," Database accession No. 10003939 & British Journal of Pharmacology, vol. 127, No. 3, pp. 623–630 (1999).

*Primary Examiner*—Zinna Northington Davis
(74) *Attorney, Agent, or Firm*—Alexander Wilson

(57) ABSTRACT

The present invention provides novel compounds of Formula I or Formula II, or the pharmaceutically acceptable salts or prodrugs thereof, pharmaceutical compositions comprising an effective amount of a compound of Formula I or Formula II in combination with a suitable carrier, diluent, or excipient, and methods for treating neurological disorders and neurodegenerative diseases, particularly pain and migraine.

28 Claims, No Drawings

EXCITATORY AMINO ACID RECEPTOR ANTAGONISTS

REFERENCE TO RELATED APPLICATIONS

This application is a 371 of PCT/US01/44714 filed Dec. 20, 2201, which claims benefit of the provisional application No. 60/259,921 filed Jan. 5, 2001.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathways in mammals, and is referred to as an excitatory amino acid (EAA). The receptors that respond to glutamate are called excitatory amino acid receptors (EAA receptors). See Watkins & Evans, *Ann. Rev. Pharmacol, Toxicol.,* 21, 165 (1981); Monaghan, Bridges, and Cotman, *Ann. Rev. Pharmacol, Toxicol.,* 29, 365 (1989); Watkins, Krogsgaard-Larsen, and Honore, *Trans. Pharm. Sci.,* 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). Molecular biological studies have established that AMPA receptors are composed of subunits ($GluR_1$–$GluR_4$), which can assemble to form functional ion channels. Five kainate receptors have been identified which are classified as either High Affinity (KA1 and KA2) or Low Affinity (composed of $GluR_5$, $GluR_6$, and/or $GluR_7$ subunits). Bleakman et al., *Molecular Pharmacology,* 49, No.4,581, (1996). The second general type of receptor is the G-protein coupled or second messenger-linker "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.,* 14, 13 (1993). Both types of excitatory amino acid receptor appear not only to mediate normal synaptic transmission along excitatory pathways, but also to participate in the modification of synaptic connections during development and throughout life. Schoepp, Bockaert, and Sladeczek, *Trends in Pharmacol. Sci.,* 11, 508 (1990); McDonald and Johnson, *Brain Research Reviews,* 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of neurological disorders and conditions. The medical consequences of such neuronal degeneration makes the abatement of these degenerative neurological processes an important therapeutic goal. For instance, excitatory amino acid receptor excitotoxicity has been implicated in the pathophysiology of numerous neurological disorders, including the etiology of cerebral deficits subsequent to cardiac bypass surgery and grafting, stroke, cerebral ischemia, spinal cord lesions resulting from trauma or inflammation, perinatal hypoxia, cardiac arrest, and hypoglycemic neuronal damage. In addition, excitotoxicity has been implicated in chronic neurodegenerative conditions including Alzheimer's Disease, Huntington's Chorea, inherited ataxias, AIDS-induced dementia, amyotrophic lateral sclerosis, idiopathic and drug-induced Parkinson's Disease, as well as ocular damage and retinopathy. Other neurological disorders implicated with excitotoxicity and/or glutamate dysfunction include muscular spasticity including tremors, drug tolerance and withdrawal, brain edema, convulsive disorders including epilepsy, depression, anxiety and anxiety related disorders such as post-traumatic stress syndrome, tardive dyskinesia, and psychosis related to depression, schizophrenia, bipolar disorder, mania, and drug intoxication or addiction (see generally U.S. Pat. No. 5,446, 051 and 5,670,516). Excitatory amino acid receptor antagonists may also be useful as analgesic agents and for treating or preventing various forms of headache, including cluster headache, tension-type headache, and chronic daily headache. In addition, published International Patent application WO 98/45720 reports that excitatory amino acid receptor excitotoxicity participates in the etiology of acute and chronic pain states including severe pain, intractable pain, neuropathic pain, post-traumatic pain.

It is also known that trigeminal ganglia, and their associated nerve pathways, are associated with painful sensations of the head and face such as headache and, in particular, migraine. Moskowitz (*Cephalalgia,* 12, 5–7, (1992) proposed that unknown triggers stimulate the trigeminal ganglia which in turn innervate vasculature within cephalic tissue, giving rise to the release of vasoactive neuropeptides from axons innervating the vasculature. These neuropeptides initiate a series of events leading to neurogenic inflammation of the meninges, a consequence of which is pain. This neurogenic inflammation is blocked by sumatriptan at doses similar to those required to treat acute migraine in humans. However, such doses of sumatriptan are associated with contraindications as a result of sumatriptan's attendant vasoconstrictive properties.(see MacIntyre, PD., et al., *British Journal of Clinical Pharmacology,* 34, 541–546 (1992); Chester, A. H., et al., *Cardiovascular Research,* 24, 932–937 (1990); Conner, H. E., et al., *European Journal of Pharmacology,* 161, 91–94 (1990)). Recently, it has been reported that all five members of the kainate subtype of ionotropic glutamate receptors are expressed on rat trigeminal ganglion neurons, and in particular, high levels of $GluR_5$ and KA2 have been observed. (Sahara et at., *The Journal of Neuroscience,* 17(17), 6611 (1997)). As such, migraine presents yet another neurological disorder which may be implicated with glutamate receptor excitotoxicity.

The use of a neuroprotective agent, such as an excitatory amino acid receptor antagonist, is believed to be useful in treating or preventing all of the aforementioned disorders and/or reducing the amount of neurological damage associated with these disorders. For example, studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported effective in preventing global and focal ischemic damage. Sheardown et al., *Science,* 247, 571 (1900); Buchan et al., *Neuroreport,* 2, 473 (1991); LePeillet et al., *Brain Research,* 571, 115 (1992). The noncompetitive AMPA receptor antagonists GKYI 52466 has been shown to be an effective neuroprotective agent in rat global ischemia models. LaPeillet et al., *Brain Research,* 571, 115 (1992). European Patent Application Publication Nos. 590789A1 and U.S. Pat. Nos. 5,446,051 and 5,670,516 disclose that certain decahydroisoquinoline derivative compounds are AMPA receptor antagonists and, as such, are useful in the treatment of a multitude of disorders conditions, including pain and migraine headache. WO 98/45270 discloses that certain decahydroisoquinoline derivative compounds are selective antagonists of the iGluR$_5$ receptor and are useful for the treatment of various types of pain, including; severe, chronic, intractable, and neuropathic pain.

In accordance with the present invention, Applicants have discovered novel compounds that are antagonists of the iGluR$_5$ receptor subtype and, thus, could be useful in treating the multitude of neurological disorders or neurodegenerative diseases, as discussed above. Such antagonists could address a long felt need for safe and effective treatments for neruological disorders, without attending side effects. The treatment of neurological disorders and neurodegenerative diseases is hereby furthered.

SUMMARY OF THE INVENTION

The present invention provides a compound of Formula I

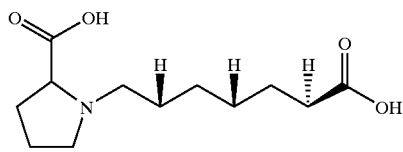

Formula I wherein,

R$^1$ represents hydrogen, chlorine, bromine, iodine, fluorine, SR$^3$, or hydroxy;

R$^2$ represents hydrogen or fluorine, with the proviso that where R$^1$ is other than fluorine, then R$^2$ represents hydrogen; and R$^3$ represents tetrazole, substituted tetrazole, triazole, (C$_1$–C$_4$)alkyl, or (C$_1$–C$_4$)alkyl-CO$_2$H;

with the further proviso that where R$^1$ and R$^2$ each independently represent fluorine, the compound is of the formula

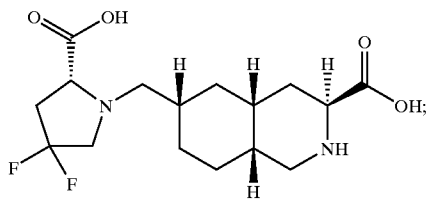

or a pharmaceutically acceptable salt or prodrug thereof.

In addition, the present invention provides a compound of Formula II

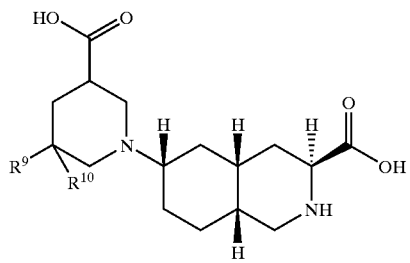

Formula II wherein,

R9 represents hydrogen, chlorine, bromine, iodine, fluorine, hydroxy, tetrazole, or a group of the formula:

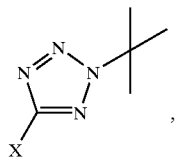

wherein X represents (C$_1$–C$_4$)alkyl or phenyl; and

R10 represents hydrogen or fluorine, with the proviso that where R$^9$ is other than fluorine, then R$^{10}$ represents hydrogen, or a pharmaceutically acceptable salt or prodrug thereof.

In another embodiment, the present invention provides a method of treating or preventing a neurological disorder, or neurodegenerative condition, comprising administering to a patient in need thereof an effective amount of a compound of Formula I or or Formula II, or a pharmaceutically acceptable salt thereof. Examples of such neurological disorders, or neurodegenerative conditions, include: cerebral deficits subsequent to cardiac bypass surgery and grafting; stroke; cerebral ischemia; spinal cord lesions resulting from trauma or inflammation; perinatal hypoxia; cardiac arrest; hypoglycemic neuronal damage; Alzheimer's Disease; Huntington's Chorea; inherited ataxias; AIDS-induced dementia; amyotrophic lateral sclerosis; idiopathic and drug-induced Parkinson's Disease; ocular damage and retinopathy; muscular spasticity including tremors; drug tolerance and withdrawal; brain edema; convulsive disorders including epilepsy; depression; anxiety and anxiety related disorders such as post-traumatic stress syndrome; tardive dyskinesia; psychosis related to depression, schizophrenia, bipolar disorder, mania, and drug intoxication or addiction; headache, including cluster headache, tension-type headache, and chronic daily headache; migraine; and acute and chronic pain states including severe pain, intractable pain, neuropathic pain, and post-traumatic pain.

More specifically, the present invention provides a method of treating or preventing pain or migraine comprising administering to a patient in need thereof an effective amount of a compound of Formula I or Formula II, or a pharmaceutically acceptable salt or prodrug thereof.

In addition, the present invention provides pharmaceutical compositions of compounds of Formula I or Formula II, including the pharmaceutically acceptable salts, prodrugs, and hydrates thereof, comprising, a compound of Formula I or Formula II in combination with a pharmaceutically acceptable carrier, diluent or excipient. This invention also encompaeees novel intermediates, and processes for the synthesis of the compounds of Formula I and Formula II.

The present invention also provides the use of a compound of Formula I or Formula II for the manufacture of a medicament for treating or preventing a neurological disorder, or neurodegenerative condition.

More specifically, the present invention provides the use of a compound of Formula I or Formula II for the manufacture of a medicament for treating or preventing pain or migraine.

DETAILED DESCRIPTION OF THE INVENTION

The present invention provides compounds functional as iGluR$_5$ receptor antagonists as well as pharmaceutically acceptable salts, prodrugs, and compositions thereof. These compounds are useful in treating or preventing neurological disorders, or neurodegenerative diseases, particularly pain and migraine. As such, methods for the treatment or prevention of neurological disorders, or neurodegenerative diseases, are also provided by the present invention.

In addition, it should be understood by the skilled artisan that all of the compounds useful for the methods of the present invention are available for prodrug formulation. As used herein, the term "prodrug" refers to a compound of Formula I or Formula II which has been structurally modified such that in vivo the prodrug is converted, for example, by hydrolytic, oxidative, reductive, or enzymatic cleavage into the parent compound (e.g. the carboxylic acid (drug), or as the case may be the parent dicarboxylic acid (drug)) as given by Formula I or Formula II. Such prodrugs may be, for example, metabolically labile mono- or di-ester derivatives of the parent compounds having a carboxylic acid group. It is to be understood that the present invention includes any such prodrugs, such as metabolically labile ester or diester derivatives of compounds of Formula I or Formula II. In all cases, the use of the compounds described herein as prodrugs is contemplated, and often is preferred, and thus, the prodrugs of all of the compounds provided are encompassed in the names of the compounds herein. Conventional procedures for the selection and preparation of suitable prodrugs are well known to one of ordinary skill in the art.

More specifically, examples of prodrugs of Formula I which are understood to be included within the scope of the present invention, are represented by Formula Ia below:

Formula Ia

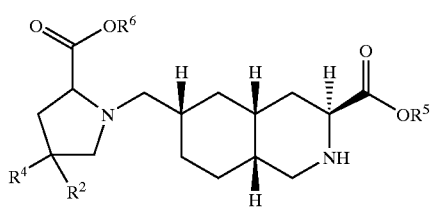

wherein, $R^2$ is as previously defined hereinabove;

$R^4$ represents hydrogen, chlorine, bromine, iodine, fluorine, $SR^7$, or hydroxy, with the proviso that where $R^4$ is other than fluorine, then $R^2$ represents hydrogen;

$R^7$ represents tetrazole, substituted tetrazole, triazole, $(C_1–C_4)$alkyl, $(C_1–C_4)$alkyl-$CO_2R^8$; and $R^5$, $R^6$, and $R^8$ each independently represent hydrogen, $(C_1–C_{20})$alkyl, $(C_2–C_6)$alkenyl, $(C_1–C_6)$alkylaryl, $(C_1–C_6)$alkyl$(C_3–C_{10})$cycloalkyl, $(C_1–C_6)$alkyl-N,N—C—C6 dialkylamine, $(C_{1-C6})$alkyl-pyrrolidine, $(C_{1-C6})$alkyl-piperidine, or $(C_{1-C6})$alkyl-morpholine, with the proviso that at least one of $R^5$, $R^6$, or $R^8$ is other than hydrogen;

with the further proviso that where $R^2$ and $R^4$ each independently represent fluorine, then the compound is of the formula

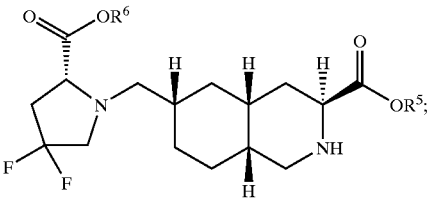

or a pharmaceutically acceptable salt thereof.

Examples of prodrugs of Formula II, which are also understood to be included within the scope of the present invention, are represented by Formula IIa below:

Formula IIa

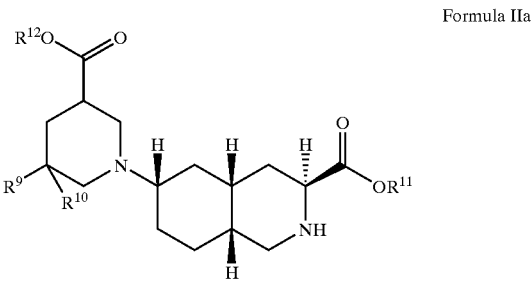

wherein, $R^9$ and $R^{10}$ are as defined hereinabove; and $R^{11}$ and $R^{12}$ each independently represent hydrogen, $(C_{1-C20})$alkyl, $(C_{2-C6})$alkenyl, $(C_{1-C6})$alkylaryl, $(C_{1-C6})$alkyl$(C_{3-C10})$-cycloalkyl, $(C_{1-C6})$alkyl-N,N—$C_{1-C6}$ dialkylamine, $(C_{1-C6})$alkyl-pyrrolidine, $(C_{1-C6})$ alkyl-piperidine, or $(C_{1-C6})$alkyl-morpholine, with the proviso that at least one of $R^{11}$ or $R^{12}$ is other than hydrogen, or a pharmaceutically acceptable salt thereof.

It is understood that the iGluR$_5$ receptor antagonists of the present invention may exist as pharmaceutically acceptable salts and, as such, salts are therefore included within the scope of the present invention. The term "pharmaceutically acceptable salt" as used herein, refers to salts of the compounds provided by, or employed in the present invention which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described herein as salts is contemplated in the description herein, and often is preferred, and the pharmaceutically acceptable salts of all of the compounds are included in the names of them.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihyroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, mandelic acid, and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemnic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I and fromula II can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. AU such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of Formula I and Formula II can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein the term "Pg" or "PG" refers to a suitable nitrogen protecting group. Examples of a suitable nitrogen protecting group as used herein refers to those groups intended to protect or block the nitrogen group against undesirable reactions during synthetic procedures. Choice of the suitable nitrogen protecting group used will depend upon the conditions that will be employed in subsequent reaction steps wherein protection is required, and is well within the knowledge of one of ordinary skill in the art. Commonly used nitrogen protecting groups are disclosed in Greene, "Protective Groups In Organic Synthesis," (John Wiley & Sons, New York (1981)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro4,5-methoxybenzyloxycarbonyl, 3,4,5-trimethoxybenzyloxycarbonyl, 1-(p-biphenylyl)-1-methylethoxycarbonyl, .alpha.alpha.-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-thichloroethoxycarbonyl, phenoxycarbonyl, 4 nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable nitrogen protecting groups are formyl, acetyl, methyloxycarbonyl, benzoyl, pivaloyl, t-butylacetyl, phenylsulfonyl, benzyl, t-butyloxycarbonyl (Boc) and benzyloxycarbonyl (Cbz).

As used herein the term "$(C_1-C_4)$alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "$(C_1-C_4)$alkyl" is included within the definition of "$(C_1-C_6)$alkyl".

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-methyl-3-pentyl, 2-methyl-2-hexyl, octyl, 4-methyl-3-heptyl and the like. It is understood that the terms "$(C_1-C_{10})$alkyl" and "$(C_1-C_6)$alkyl" are included within the definition of "$(C_1-C_{10})$alkyl".

As used herein the terms "$(C_1-C_{20})$alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like. It is understood that the terms "$(C_1-C_4)$alkyl", "$(C_1-C_6)$alkyl", and "$(C_1-C_{10})$alkyl" are included within the definition of "$(C_1-C_{20})$alkyl".

As used herein, the terms "Me", "Et", "Pr", "iPr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methyoxy, ethyoxy, n-propoxy, isopropoxy, n-butoxy, and the like.

As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like.

As used herein, the term "$(C_1-C_6)$alkyl$(C_1-C_6)$alkoxy" refers to a straight or branched, monovalent, saturated aliphatic chain of 1 to 6 carbon atoms which has a $(C_1-C_6)$ alkoxy group attached to the aliphatic chain.

As used herein, the terms "Halo", "Halide" or "Hal" refer to a chlorine, bromine, iodine or fluorine atom, unless otherwise specified herein.

As used herein the term "$(C_2-C_6)$alkenyl" refers to a straight or branched, monovalent, unsaturated aliphatic chain having from two to six carbon atoms. Typical $C_2-C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like. The term "substituted aryl" refers to an aryl group substituted with one or two moieties chosen from the group consisting of halogen, hydroxy, cyano, nitro, $(C_1-C_6)$alkyl, $(C_1-C_4)$alkoxy, $(C_1-C_6)$alkyl $(C_3-C_{10})$cycloalkyl, $(C_1-C_6)$alkylaryl, $(C_1-C_6)$ alkoxycarbonyl, protected carboxy, carboxymethyl, hydroxymethyl, amino, aminomethyl, or trifluoromethyl.

As used herein, the term "$(C_1-C_6)$alkylaryl" refers to a straight or branched, monovalent, saturated aliphatic chain of 1 to 6 carbon atoms which has an aryl group attached to the aliphatic chain. Included within the term "$C_1-C_6$ alkylaryl" are the following:

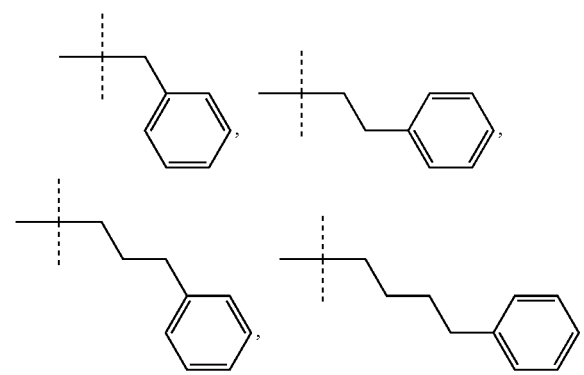

and the like.

As used herein, the term "aryl$(C_1-C_6)$alkyl" refers to an aryl group which has a straight or branched, monovalent, saturated aliphatic chain of 1 to 6 carbon atoms attached to the aryl group. Included within the term "aryl$(C_1-C_6)$alkyl" are the following:

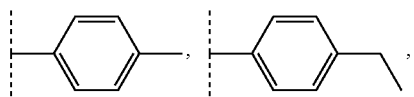

-continued

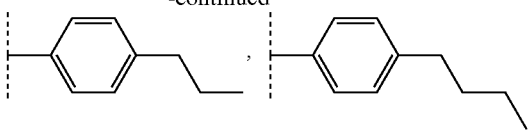

and the like.

As used herein the term "$(C_3-C_{10})$cycloalkyl" refers to a saturated hydrocarbon ring structure composed of one or more fused or unfused rings containing from three to ten carbon atoms. Typical $C_3-C_{10}$ cycloalkyl groups include cyclopropyl, cyclobutyl, cyclopentyl, cyclohexyl, cycloheptyl, cyclooctyl, adamantanyl, and the like.

As used herein, the term "$C_1-C_6$ alkyl($C_3-C_{10}$) cycloalkyl" refers to a straight or branched, monovalent, saturated aliphatic chain of 1 to 6 carbon atoms which has a $(C_3-C_{10})$cycloalkyl attached to the aliphatic chain. Included within the term "$C_1-C_6$ alkyl($C_3-C_{10}$)cycloalkyl" are the following:

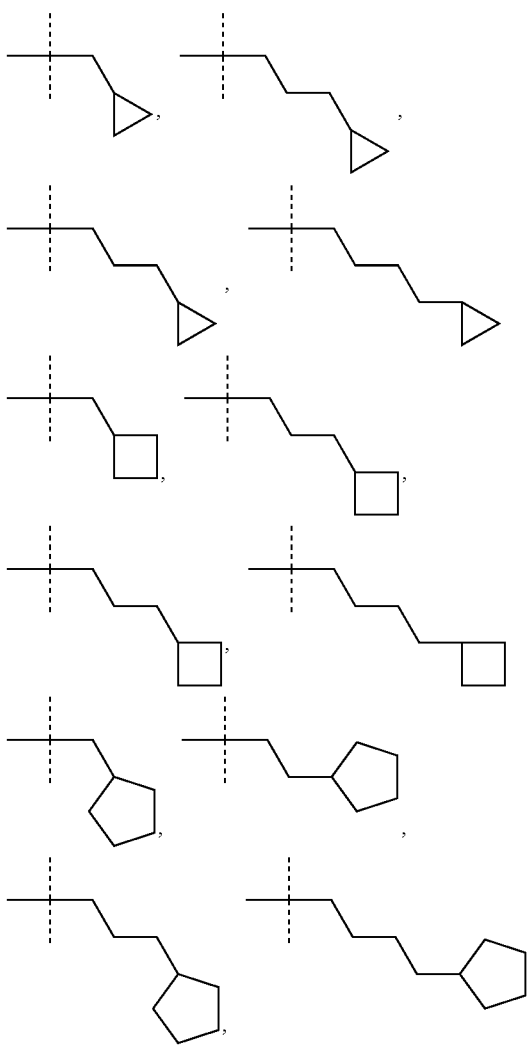

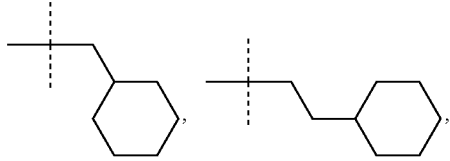

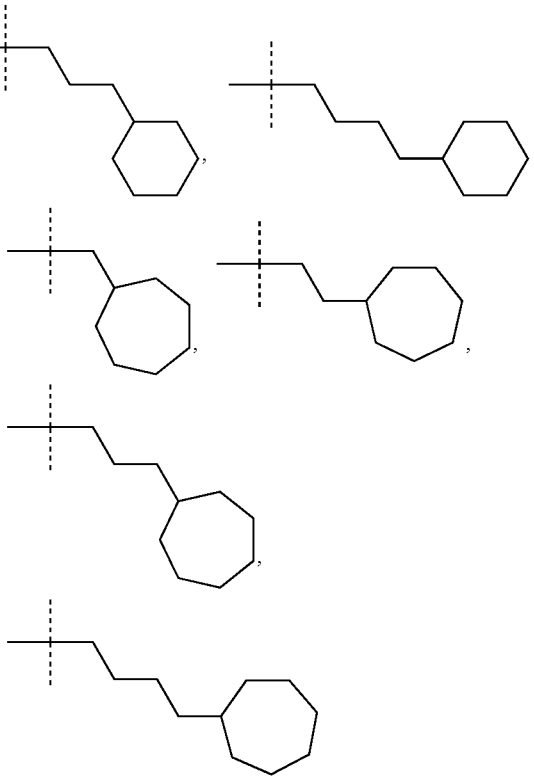

and the like.

As used herein, the term "$(C_1-C_6)$ alkoxycarbonyl" refers to a carbonyl group having a $(C_1-C_6)$alkyl group attached to the carbonyl carbon through an oxygen atom. Examples of this group include t-buoxycarbonyl, methoxycarbonyl, and the like.

As used herein the term "heterocycle" refers to a five- or six-membered ring, which contains one to four heteroatoms selected from the group consisting of oxygen, sulfur, and nitorgen. The remaining atoms of the ring are recognized as carbon by those of skill in the art. Rings may be saturated or unsaturated. Examples of heterocycle groups include thiophenyl, furyl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidinyl, morpholinyl, pyranyl, thiomorpholinyl, and the like. The term "substituted heterocycle" represents a heterocycle group substituted with one or two moieties chosen from the group consisting of aryl, halogen, hydroxy, cyano, nitro, oxo, $(C_1-C_6)$alkyl, $(C_1-C_4)$alkoxy, $C_1-C_6$ alkyl($C_3-C_{10}$)cycloalkyl, $(C_1-C_6)$alkylaryl, $(C_1-C_6)$ alkoxycarbonyl, protected carboxy, carboxymethyl, hydroxymethyl, amino, aminomethyl, or trifluoromethyl. Further, the heterocycle group can be optionally fused to one or two aryl groups to form a benzo-fused group. Examples of substituted heterocycle include 1,2,3,4-tetrahydrodibenzeofuranyl, 2-methylbezylfuranyl, and 3,5 dimethylisoxazolyl, and the like.

As used herein, the term "substituted tetrazole" refers to a tetrazole group substituted with a $(C_1-C_4)$alkyl moiety. Examples of substituted tetrazole as used herein include:

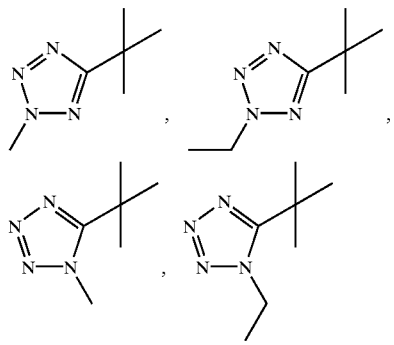

and the like.

As used herein, the term "$(C_1-C_6)$alkyl-heterocycle" refers to a straight or branched, monovalent, saturated aliphatic chain of 1 to 6 carbon atoms bearing a heterocycle group. Further, as used herein, the term "$(C_1-C_6)$alkyl-(substituted)heterocycle" refers to a straight or branched, monovalent, saturated aliphatic chain of 1 to 6 carbon atoms bearing a substituted heterocycle group.

As used herein, the term "$(C_1-C_6)$alkyltetrazole" refers to a straight or branched, monovalent, saturated aliphatic chain of 1 to 6 carbon atoms bearing a tetrazole group.

As used herein the term "N,N—$C_1-C_6$ dialkylamine" refers to a nitrogen atom substituted with two straight or branched, monovalent, saturated aliphatic chains of 1 to 6 carbon atoms. Included within the term "N,N—$C_1-C_6$ dialkylamine" are —$N(CH_3)_2$, —$N(CH_2CH_3)_2$, —$N(CH_2CH_2CH_3)_2$, —$N(CH_2CH_2CH_2CH_3)_2$, and the like.

As used herein the term "$C_1-C_6$alkyl-N,N—$C_1-C_6$-dialkylamine" refers to straight or branched, monovalent, saturated aliphatic chain of 1 to 6 carbon atoms which has an N,N—$C_1-C_6$ dialkylamine attached to the aliphatic chain. Included within the term "$C_1-C_6$ alkyl-N,N—$C_1-C_6$ dialkylamine" are the following:

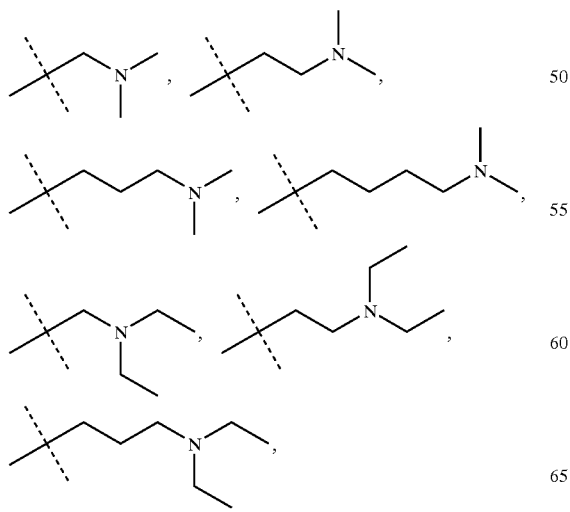

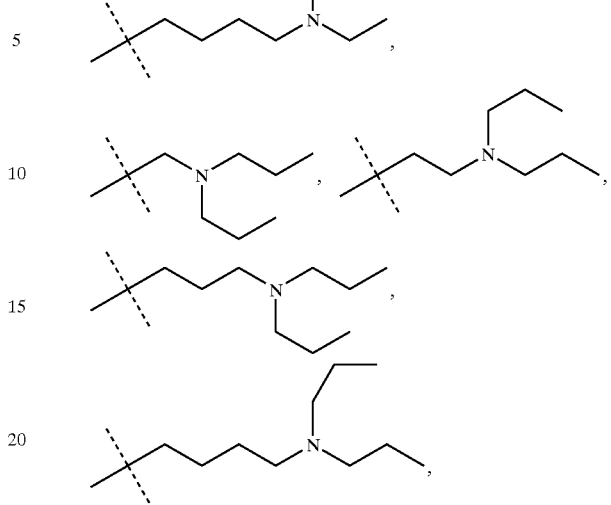

and the like.

As used herein the term "$(C_1-C_6)$alkyl-pyrrolidine" refers to a straight or branched, monovalent, saturated aliphatic chain of 1 to 6 carbon atoms which has a pyrrolidine attached to the aliphatic chain. Included within the scope of the term "$(C_1-C_6)$alkyl-pyrrolidine" are the following

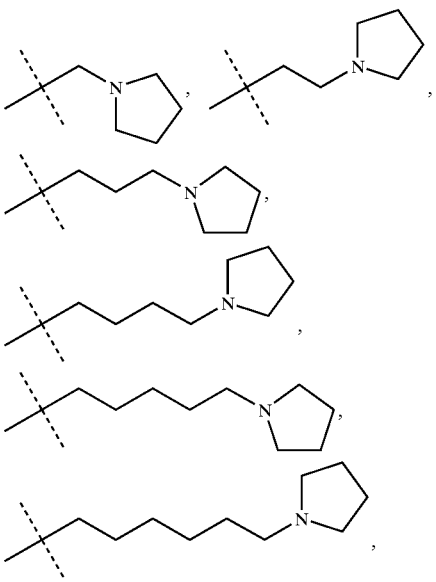

and the like.

As used herein the term "$(C_1-C_6)$alkyl-piperidine" refers to a straight or branched, monovalent, saturated aliphatic chain of 1 to 6 carbon atoms which has a piperidine attached to the aliphatic chain. Included within the scope of the term "$(C_1-C_6)$alkyl-piperidine" are the following:

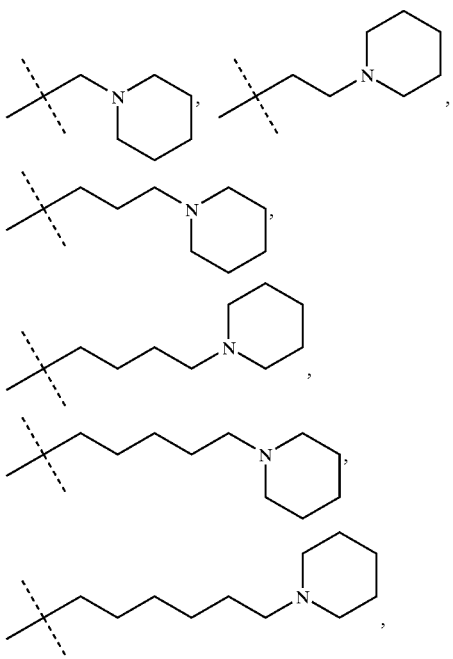

and the like.

As used herein the term "$(C_1-C_6)$alkyl-morpholine" refers to a straight or branched, monovalent, saturated aliphatic chain of 1 to 6 carbon atoms which has a morpholine attached to the aliphatic chain. Included within the scope of the term "$C_1-C_6$ alkyl-morpholine" are the following:

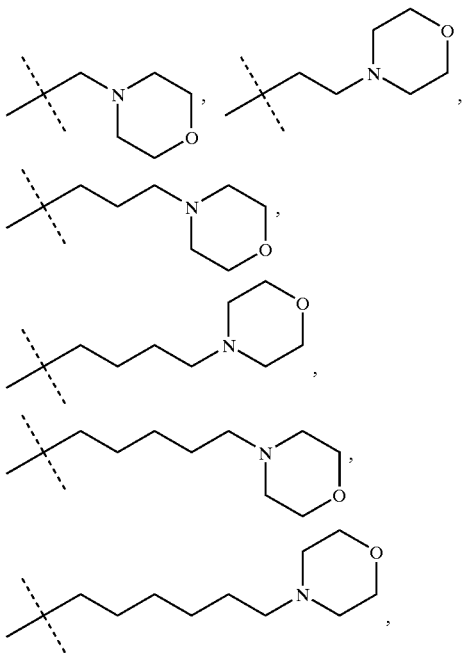

and the like.

The designation "◀" refers to a bond that protrudes forward out of the plane of the page.

The designation "⦀⦀" refers to a bond that protrudes backward out of the plane of the page.

As used herein the term "iGluR$_5$" refers to the kainate ionotropic glutamate receptor, subtype 5, of the larger class of excitatory amino acid receptors.

As used herein the term "migraine" refers a disorder of the nervous system characterized by recurrent attacks of head pain (which are not caused by a structural brain abnormality such as those resulting from tumor or stroke), gasrointestinal disturbances, and possibly neurological symptoms such as visual distortion. Characteristic headaches of migraine usually last one day and are commonly accompanied by nausea, emesis, and photophobia.

Migraine may represent a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of migraine contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human.

The term "iGluR$_5$ receptor antagonist" or "iGluR$_5$ antagonist", as used herein, refers to those excitatory amino acid receptor antagonists which bind to, and antagonize the activity of, the iGluR$_5$ kainate receptor subtype. As a preferred embodiment, the present invention further provides selective iGluR$_5$ receptor antagonists. "Selective iGluR$_5$ receptor antagonist" or "selective iGluR$_5$ antagonist" as used herein, includes those excitatory amino acid receptor antagonists which selectively bind to, and antagonize, the iGluR$_5$ kainate receptor subtype, relative to the iGluR$_2$ AMPA receptor subtype. Preferably the "selective iGluR$_5$ antagonists" for use according to the methods of the present invention have a binding affinity at least 10 fold greater for iGluR$_5$ than for iGluR$_2$, more preferably at least 100 fold greater. WO 98/45270 provides examples of selective iGluR$_5$ receptor antagonists and discloses methods for synthesis.

As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as an $iGluR_5$ receptor antagonist. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the $iGluR_5$ receptor antagonist is administered as a combination of compounds, one of the compounds may be administered by one route, such as oral, and the other may be administered by the transdermal, percutaneous, pulmonary, intravenous, intramuscular, intranasal, buccal, sublingual, or intraectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I or Formula II are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I or Formula II, including the pharmaceutically acceptable salts, prodrugs, and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following table provides an illustrative list of formulations suitable for use with the compounds employed in the present invention. The following is provided only to illustrate the invention and should not be interpreted as limiting the present invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| Active Ingredient | 0.25 |
| Ethanol | 29.75 |
| Propellant 22 | 70.00 |
| (Chlorodifluoromethane) |  |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60.0 mg |
| --- | --- |
| Starch | 45.0 mg |
| Microcrystalline cellulose | 35.0 mg |
| Polyvinylpyrrolidone | 4.0 mg |
| Sodium carboxymethyl starch | 4.5 mg |
| Magnesium stearate | 0.5 mg |
| Talc | 1.0 mg |
| Total | 150 mg |

The active ingredient, starch, and cellulose are passed through a No 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules each containing 80 mg medicament are made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| Active Ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| Active Ingredient | 50 mg |
| --- | --- |
| Sodium carboxymethyl cellulose | 50 mg |
| Syrup | 1.25 ml |
| Benzoic acid solution | 0.10 ml |

| | |
|---|---|
| -continued | |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| Active Ingredient | 100 mg |
| Mannitol | 100 mg |
| 5N Sodium hydroxide | 200 ml |
| Purified water to total | 5 ml |

It is understood by one of ordinary skill in the art that the procedures as described above can also be readily applied to a method of treating neurological disorders or neurodegenerative conditions, particularly pain and migraine, comprising administering to a patient an effective amount of a compound of Formula I or Formula II.

Compounds of Formula I and Formula II can be prepared, for example, by following the procedures set forth in the Schemes below. All substituents, unless otherwise indicated, are previously defined. The reagents and starting materials are readily available to one of ordinary skill in the art. For example, certain starting materials can be prepared by one of ordinary skill in the art following procedures disclosed in U.S. Pat. Nos. 5,356,902 (issued Oct. 18, 1994); 5,446,051 (issued Aug. 29, 1995); and 5,670,516 (issued Sep. 23, 1997) the entire contents, all of which, are herein incorporated by reference. Certain reagents may be prepared by one of ordinary skill in the art following procedures disclosed by Demange et al., *Tetrahedron Lett.*, 39, 1169–1172 (1998).

Scheme I provides procedures for the synthesis of compounds of Formula I wherein $R^1$ and $R^2$ each independently represent fluorine.

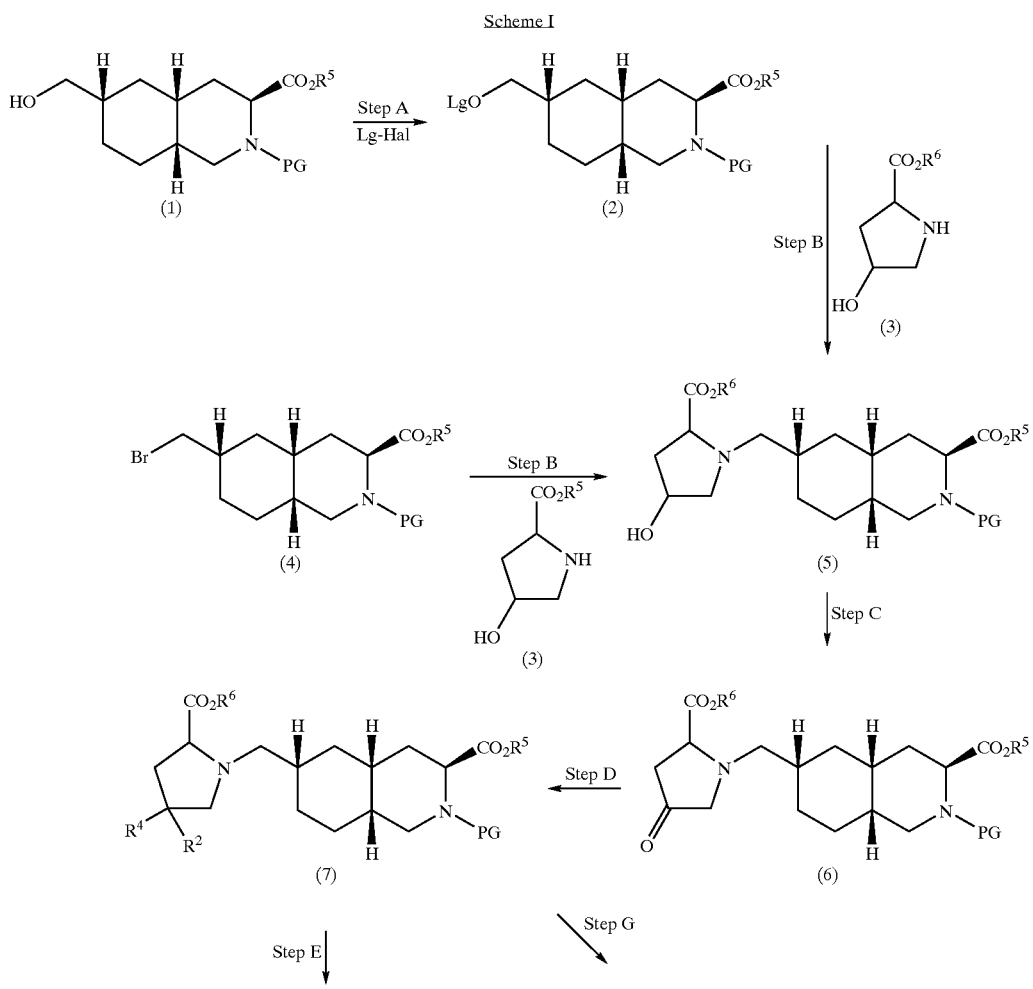

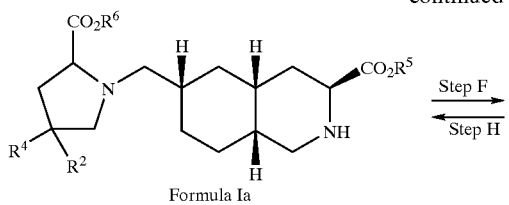 Formula Ia

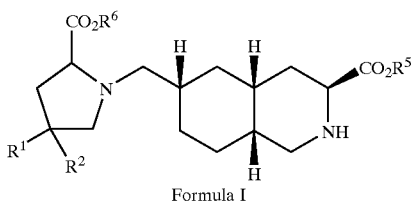 Formula I

In Scheme I, Step A, the compound of structure (1) (PG is a suitable nitrogen protecting group as defined hereinabove, with methoxylcarbonyl being preferred) is treated under standard conditions with a compound of formula Lg-Hal wherein Lg is a suitable leaving group and Hal represents a chloro, bromo or iodo atom, to provide structure (2). Examples of Lg-Hal include m-nitrobenzenesulfonyl chloride, P-nitrobenzenesulfonyl chloride, p-bromobenzenesulfonyl chloride, p-toluenesulfonyl chloride, benzenesulfonyl chloride, methanesulfonyl chloride, trifluoromethanesulfonyl chloride, and the like. For example, a solution of 6-hydroxymethyl-2-methoxycarbonyl-decahydroisoquinoline-3-carboxylate, dissolved in a suitable organic solvent such as dichloromethane and cooled to 0° C., is treated with an excess of a suitable organic base, such as triethylamine, followed by about 1 to 2 equivalents of p-toluenesulfonyl chloride. The reaction mixture is warmed to room temperature and stirred for about 5 to 20 hours. The compound of structure (2) is then isolated using standard procedures. For example, the reaction mixture is washed with water, the organic layer separated and dried over anhydrous sodium sulfate, filtered, and concentrated under vacuum to provide crude compound (2). Column chromatography can then be performed on silica gel with a suitable eluent such as 10–50% ethyl acetate/hexane to provide the purified compound (2).

In Scheme I, Step B, compound (2) is treated under standard conditions with a pyrrolidine of structure (3) to provide the compound of structure (5). Alternatively, compound (4) can be treated under the same conditions to provide the compound of strucure (5). For example, compound (2) of Step A above, or alternatively 6-bromomethyl-2-methoxycarbonyl-decahydroisoquinoline-3-carboxylate, compound (4), is mixed with about 1–1.5 equivalents of 4-hydroxy-L-proline ethyl ester and 1–1.5 equivalents of potassium carbonate and heated at reflux in a suitable solvent such as acetonitrile for about 60–70 hours. The reaction mixture is cooled to room temperature and solvents removed under vacuum. Compound (5) is then isolated using standard procedures such as extraction techniques. For example, the reaction mixture is partitioned between water and an organic solvent such as diethyl ether, and the aqueous layer extracted 2–6 times with diethyl ether. The organic layers are combined, dried over anhydrous sodium sulfate, filtered, and concentrated under vacuum to provide compound (5). Compound (5) can then be purified by chromatography on silica gel with a suitable eluent such as ethyl acetate/hexanes or methanol/chloroform.

In Scheme I, Step C, treatment of compound (5) with standard oxidizing conditions provides the ketone of structure (6). For example, compound (5) can be added to a mixture of oxalyl chloride and DMSO, followed by addition of triethylamine and warming the reaction to room temperature. The reaction mixture is partitioned between water and an organic solvent such as methylene chloride, and the aqueous layer extracted 2–6 time with methylene chloride. The organic layers are combined, dried over anhydrous sodium sulfate, filtered, and concentrated under vacuum to provide compound (6). Compound (6) can then be purified using standard procedures such as chromatography on silica gel with a suitable eluent such as ethyl acetate/hexanes or methanol/chloroform.

In Scheme I Step D, the compound of strucure (6) is treated with diethylamino sulfur trifluoride to yield the intermediate of structure (7) wherein for purposes of the present scheme, $R^4$ and $R^2$ each represent flurorine. For example, to a mixture of compound (6), cooled to about −78° C. in $CH_2Cl_2$, is added dropwise diethylamino sulfur trifluoride. The reaction is allowed to warm to room temperature, stirred for about 48 hours, and quenched by addition of MeOH. The compound of structure (7) wherein for purposes of the present scheme, $R^4$ and $R^2$ each represent flurorine, is then concentrated under standard conditions. For example, compound (7) is first concentrated under vacuum, then the residue partitioned between $CH_2Cl_2$ and aqueous $NaHCO_3$. The aqueous layer is then extracted with $CH_2Cl_2$ and the combined organics dried over $MgSO4$, filtered, and concentrated under vacuum to provide the concentrated compound (7) wherein for purposes of the present scheme, $R^4$ and $R^2$ each represent flurorine. This material may then be purified by techniques well known in the art such as chromatography on silica gel with a suitable eluent, such as 25–50% EtOAc/hexane to provide the purified compound of structure (7).

In Scheme I, Step E, compound (7) is deprotected under standard conditions well known in the art to provide the compound of Formula Ia, wherein $R^4$ and $R^2$ both represent fluorine. For example, when Pg is a methoxycarbonyl protecting group, compound (7) is dissolved in a suitable organic solvent such as dichloromethane under an atmosphere of nitrogen and treated with trimethylsilyl iodide. The reaction mixture is allowed to warm to room temperature and stirred for about 10–20 hours. The reaction is quenched by addition of saturated aqueous $NaHCO_3$. The aqueous layer is then extracted 2–6 times with dichloromethane. The organics are then combined, washed with a 1N solution of sodium thiosulfate, dried over magnesium sulfate, filtered, and concentrated in vacuo to provide the compound of Formula Ia, wherein $R^4$ and $R^2$ both represent fluorine. This material can then be purified by chromatography on silica gel with a suitable eluent such as methanol/dichloromethane, to provide the purified compound of Formula Ia, wherein $R^4$ and $R^2$ both represent fluorine.

In Scheme I, Step F, the compound of Formula Ia, from Step E is hydrolyzed to the compound of Formula I, wherein $R^1$ and $R^2$ both represent fluorine, under conditions well known in the art. For example, the compound of Formula Ia is dissolved in a suitable organic solvent such as methanol, and treated with an excess of a suitable base. Examples of suitable bases include aqueous lithium hydroxide, sodium hydroxide, potassium hydroxide, and the like, with lithium hydroxide being preferred. The reaction is stirred for about 10–20 hours. The reaction mixture is then neutralized to pH 6 with 1N HCl and concentrated under vacuum to provide the crude compound of Formula I, wherein $R^1$ and $R^2$ both represent fluorine. This material can then be purified by techniques well known in the art, such as cation exchange chromatography eluting with THF/water followed by 10% pyridine in water to provide the purified compound of Formula I, wherein $R^1$ and $R^2$ both represent fluorine.

In Scheme I, Step G, compound (7) is deprotected and hydrolyzed concomitantly to provide the compound of Formula I, wherein $R^1$ and $R^2$ both represent fluorine. For example, a solution of compound (7) dissolved in 5N HCl is heated to reflux (90–95° C.) for about 15–20 hours. The reaction mixture is then allowed to cool to room temperature and concentrated in vacuo to provide the compound of Formula I, wherein $R^1$ and $R^2$ both represent fluorine. The compound of Formula I can then be purified by techniques well known in the art, such as cation exchange chromatography eluting with THF/water followed by 10% pyridine in water to provide the purified compound of Formula I, wherein $R^1$ and $R^2$ both represent fluorine.

In Scheme I, Step H, the compound of Formula I from Step F or G above, can be esterified under conditions well known in the art, to provide the compound of Formula Ia, wherein $R^4$ and $R^2$ both represent fluorine. For example, the compound of Formula I is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78–85° C.) for about 15–25 hours. The reaction mixture is concentrated under vacuum to provide the crude compound of Formula Ia, wherein $R^4$ and $R^2$ both represent fluorine. This material can then be purified by techniques well known in the art, such as cation exchange chromatography eluting with ethanol/water followed by 2N ammonia in ethanol to provide the purified compound of Formula Ia, wherein $R^4$ and $R^2$ both represent fluorine.

Scheme II provides procedures for the synthesis of compounds of Formula I, wherein $R^1$ is fluorine and $R^2$ is hydrogen.

In Scheme II, Step B, the compound of structure (4) (PG is a suitable nitrogen protecting group as defined hereinabove, with methoxylcarbonyl being preferred) is treated under standard conditions with a pyrrolidine of structure (8) (wherein for purposes of the present scheme $R^4$ is fluorine and $R^2$ is hydrogen) to provide the compound of structure (9). For example, 6-bromomethyl-2-methoxycarbonyl-decahydroisoquinoline-3-carboxylate is mixed with about 1–1.5 equivalents of trans-4-fluoro-L-proline ethyl ester (prepared by one of ordinary skill in the art following the procedures as disclosed in *Tetrahedron Lett.*, 39, 1169–1172 (1998)) and about 1–1.5 equivalents of potassium carbonate and heated at reflux in a suitable solvent such as acetonitrile for about 60–70 hours. The reaction mixture is cooled to room temperature and then loaded onto an SCX-cation exchange cartridge. Following elution with MeOH, then 2 M NH3/MeOH, compound (9) can then be purified by chromatography on silica gel with a suitable eluent such as ethyl acetate/hexanes or methanol/chloroform.

In Scheme II, Step E, compound (9) is deprotected under standard conditions well known in the art as described previously in Scheme I, Step E to provide the compound of Formula Ia, wherein for purposes of the present scheme $R^4$ is fluorine and $R^2$ is hydrogen. This material can then be concentrated and purified, again by procedures well known in the art as described in Scheme I, Step E to provide the purified compound of Formula Ia, wherein $R^4$ is fluorine and $R^2$ is hydrogen.

In Scheme II, Step F, following the procedures as described in Scheme I, Step F, the compound of Formula Ia, wherein for purposes of the present scheme $R^4$ is fluorine and $R^2$ is hydrogen, is hydrolyzed to the compound of Formula I under conditions well known in the art. This material can then be concentrated and purified by techniques well known in the art as described in Scheme I, Step F, to provide the purified compound of Formula I, wherein for purposes of the present scheme $R^1$ is fluorine and $R^2$ is hydrogen.

In Scheme II, Step G, following the procedures as described in Scheme I, Step G, compound (9) is deprotected and hydrolyzed concomitantly to provide the compound of Scheme II

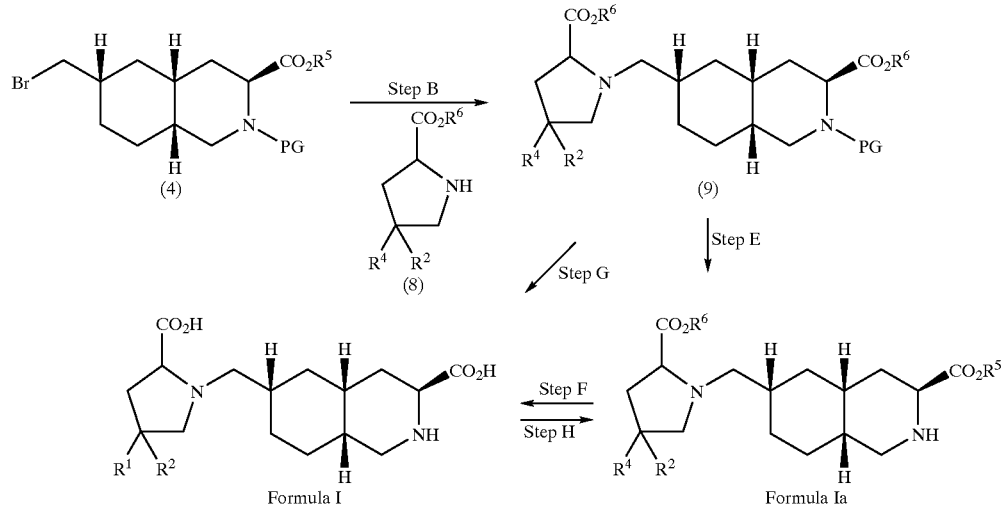

Formula I, wherein for purposes of the present scheme $R^1$ is fluorine and $R^2$ is hydrogen. The compound of Formula I can then be concentrated and purified by techniques well known in the art as described in Scheme I, Step G, to provide the purified compound of Formula I, wherein $R^1$ is fluorine and $R^2$ is hydrogen.

In Scheme II, Step H, following the procedures as described in Scheme I, Step H, the compound of Formula I, wherein for purposes of the present scheme $R^1$ is fluorine and $R^2$ is hydrogen, can be esterified under conditions well known in the art, to provide the compound of Formula Ia, wherein $R^4$ is fluorine and $R^2$ is hydrogen. This material can then be concentrated and purified by techniques well known in the art as described in Scheme I, Step H, to provide the purified compound of Formula Ia, wherein $R^4$ is fluorine and $R^2$ is hydrogen.

Scheme III provides procedures for the synthesis of compounds of Formula I wherein $R^1$ represents chlorine, bromine, or iodine, and $R^2$ represents hydrogen.

known in the art to provide the compound of Formula Ia, wherein for the purposes of the present scheme $R^4$ represents chlorine, bromine, or iodine and $R^2$ represents hydrogen. The material can then be concentrated and purified by procedures well known in the art as described in Scheme I, Step E, to provide the purified compound of Formula Ia, wherein $R^4$ represents chlorine, bromine, or iodine and $R^2$ represents hydrogen.

In Scheme III, Step F, following the procedures as described in Scheme I, Step F, the compound of Formula Ia, wherein for the purposes of the present scheme $R^4$ represents chlorine, bromine, or iodine and $R^2$ represents hydrogen, is hydrolyzed to the compound of Formula I, wherein $R^1$ represents chlorine, bromine, or iodine and $R^2$ represents hydrogen, under conditions well known in the art. This material can then be concentrated and purified by techniques well known in the art as described in Scheme I, Step F, to provide the purified compound of Formula I, wherein $R^1$ represents chlorine, bromine, or iodine and $R^2$ represents hydrogen.

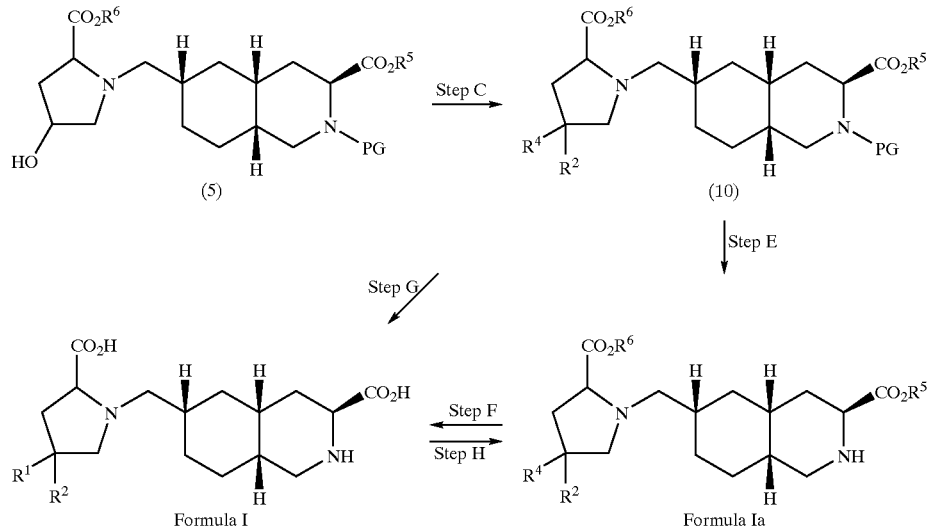

In Scheme III, Step C, the intermediate of structure (5) (prepared as described in Scheme I above) is treated under standard conditions with a halogenating source to provide the compound of structure (10), wherein $R^4$ for the purposes of this scheme represents chlorine, bromine, or iodine and $R^2$ represents hydrogen. For example, compound (5) is mixed with about 1–1.5 equivalents of a solution of triphenylphosphine and $CCl_4$ and stirred at room temperature in a suitable solvent such as methylene chloride for about 20 hours. The compound of structure (10) is then isolated using standard procedures. For example, the reaction mixture is washed with water, the organic layer separated and dried over anhydrous sodium sulfate, filtered, and concentrated under vacuum to provide crude compound (10), wherein $R^4$ represents chlorine, bromine, or iodine and $R^2$ represents hydrogen. Column chromatography can then be performed on silica gel with a suitable eluent such as 10–50% ethyl acetate/hexane to provide the purified compound (10), wherein $R^4$ represents chlorine, bromine, or iodine and $R^2$ represents hydrogen.

In Scheme III, Step E, following the procedures as described in Scheme I, Step E, compound (10) from Scheme III, Step C is deprotected under standard conditions well In Scheme III, Step G, following the procedures as described in Scheme I, Step G, compound (10), wherein for the purposes of the present scheme $R^4$ represents chlorine, bromine, or iodine and $R^2$ represents hydrogen, is deprotected and hydrolyzed concomitantly to provide the compound of Formula I, wherein $R^1$ represents chlorine, bromine, or iodine and $R^2$ represents hydrogen. The compound of Formula I can then be concentrated and purified by techniques well known in the art as described in Scheme I, Step G, to provide the purified compound of Formula I, wherein for the purposes of the present scheme $R^1$ represents chlorine, bromine, or iodine and $R^2$ represents hydrogen.

In Scheme III, Step H, following the procedures as described in Scheme I, Step H, the compound of Formula I, wherein for the purposes of the present scheme $R^1$ represents chlorine, bromine, or iodine and $R^2$ represents hydrogen, can be esterified, under conditions well known in the art, to provide the compound of Formula Ia, wherein $R^4$ represents chlorine, bromine, or iodine and $R^2$ represents hydrogen. This material can then be concentrated and purified by techniques well known in the art as described in Scheme I, Step H to provide the purified compound of Formula Ia, wherein for purposes of the present scheme $R^4$ represents chlorine, bromine, or iodine and $R^2$ represents hydrogen.

Scheme IV provides procedures for the synthesis of compounds of Formula I wherein $R^1$ represents $SR^3$, $R^2$ represents hydrogen, and $R^3$ represents tetrazole, substituted tetrazole, or triazole.

separated and dried over anhydrous sodium sulfate, filtered, and concentrated under vacuum to provide crude compound (11). Column chromatography can then be performed on silica gel with a suitable eluent such as 10–50% ethyl acetate/hexane to provide the purified compound (11).

Alternatively, compound (5) is added to a solution of about 1.5 equivalents of triphenylphosphine and about 1.5

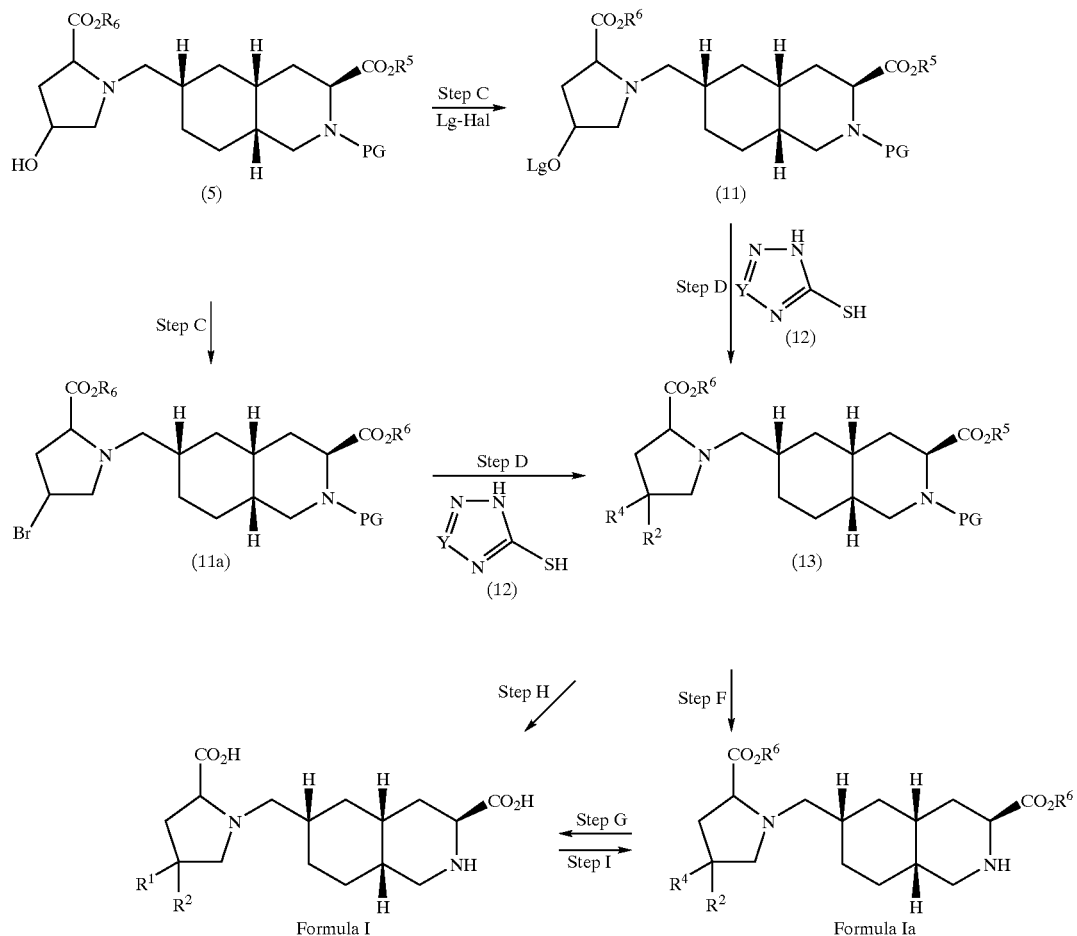

In Scheme IV, Step C, the intermediate (5) (prepared as described in Scheme I) is treated under standard conditions with a compound of formula Lg-Hal, wherein LG is a suitable leaving group and Hal represents a chloro, bromo or iodo atom, to provide the compound of structure (11). Alternatively (5) may be treated under standard conditions with a brominating source, providing intermediate (11a). For example, a solution of compound (5), dissolved in a suitable organic solvent such as dichloromethane and cooled to 0° C., is treated with an excess of a suitable organic base, such as triethylamine, followed by about 1 to 2 equivalents of a compound of formula Lg-Hal. Examples of Lg-Hal include m-nitrobenzenesulfonyl chloride, p-nitrobenzenesulfonyl chloride, p-bromobenzenesulfonyl chloride, p-toluenesulfonyl chloride, benzenesulfonyl chloride, methanesulfonyl chloride, trifluoromethanesulfonyl chloride, and the like. The reaction mixture is warmed to room temperature and stirred for about 5 to 20 hours. The compound (11) is then isolated using standard procedures. For example, the reaction mixture is washed with water, the organic layer equivalents of bromine premixed in a suitable solvent such as methylene chloride. The reaction is further treated with approximately 2 equivalents of pyridine, then stirred for about 20 hours. The compound of structure (11a) is then isolated using standard procedures. For example, the reaction mixture is washed with water, the organic layer separated and dried over anhydrous sodium sulfate, filtered, and concentrated under vacuum to provide crude compound (11a). Column chromatography can then be performed on silica gel with a suitable eluent such as 10–50% ethyl acetate/hexane to provide the purified compound of structure (11a).

In Scheme IV, Step D, compound (11) or compound (11a) is treated with a compound of structure (12), wherein Y represents CH or N, in the presence of potassium carbonate to give the compound of structure (13), wherein for purposes of the present scheme $R^2$ is hydrogen, $R^4$ is $SR^7$, and $R^7$ represents tetrazole or triazole. For example, a solution of (11), about 3 equivalents of thiotetrazole, and about 1.5 equivalents of potassium carbonate in acetonitrile is heated to 80° C. for about 60 hours. The compound (13) is then isolated using standard procedures. For example, the reaction mixture is washed with water, the organic layer separated and dried over anhydrous sodium sulfate, filtered, and concentrated under vacuum to provide crude compound (13), wherein for purposes of the present scheme $R^2$ is hydrogen, $R^4$ is $SR^7$, and $R^7$ represents tetrazole or triazole. Column chromatography can then be performed on silica gel with a suitable eluent such as 10–50% ethyl acetate/hexane to provide the purified compound (13).

This intermediate can be deprotected as describe infra, or alternatively, where $R^7$ represents tetrazole, the compound (13) may be further alkylated with a compound of formula Z-halo, (wherein Z represents $(C_1-C_4)$alkyl and halo represents a chloro, bromo or iodo atom) to provide a compound of structure (14a) or (14b) below:

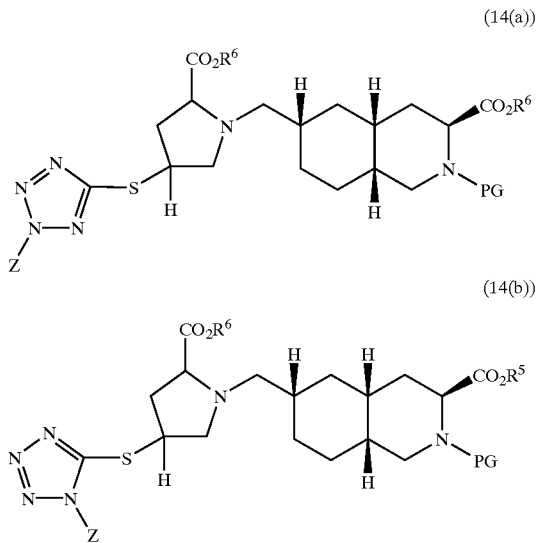

(14(a))

(14(b))

wherein Z represents a $(C_1-C_4)$alkyl group.

For example, a solution of compound (13), wherein $R^7$ represents tetrazole, dissolved in a suitable organic solvent such as THF and cooled to 0° C., is treated with an excess of NaH, followed by iodomethane. The compound (14), wherein $R^2$ is hydrogen, $R^4$ is $SR^7$, and $R^7$ represents a substituted tetrazole, is then isolated using standard procedures. For example, the reaction mixture is washed with water, the organic layer separated and dried over anhydrous sodium sulfate, filtered, and concentrated under vacuum to provide the crude mixture of compounds (14a) and (14b) wherein $R^2$ is represented by hydrogen, $R^4$ is represented by $SR^7$, and $R^7$ represents a substituted tetrazole (Z represents a $(C_1-C_4)$alkyl group). Column chromatography can then be performed on silica gel with a suitable eluent such as 10–50% ethyl acetate/hexane to separate isomers (14a) and (14b), providing the purified compound (14a) or (14b).

In Scheme IV, Step F, compound (13), or alternatively, compound (14(a) or (b)) (both as defined previously above) is deprotected under standard conditions well known in the art to provide the compound of Formula Ia, wherein $R^2$ is hydrogen, $R^4$ is $SR^7$, and $R^7$ represents tetrazole, substituted tetrazole, or triazole. For example, when PG is a methoxycarbonyl protecting group, compound (14) is dissolved in a suitable organic solvent such as dichloromethane under an atmosphere of nitrogen and treated with trimethylsilyl iodide. The reation mixture is allowed to warm to room temperature and stirred for about 10–20 hours. The reaction is quenched by addition of saturated aqueous $NaHCO_3$. The aqueous layer is then extracted 2–6 times with dichloromethane. The organics are then combined, washed with a 1N solution of sodium thiosulfate, dried over magnesium sulfate, filtered, and concentrated in vacuo to provide the compound of Formula Ia, wherein $R^2$ is hydrogen, $R^4$ is $SR^7$, and $R^7$ represents tetrazole, substituted tetrazole, or triazole. The material can then be purified by chromatography on silica gel with a suitable eluent such as methanol/dichloromethane, to provide the purified compound of Formula Ia, wherein $R^2$ is hydrogen, $R^4$ is $SR^7$, and $R^7$ represents tetrazole, substituted tetrazole, or triazole.

In Scheme IV, Step G, the compound of Formula Ia is hydrolyzed to the compound of Formula I, wherein $R^2$ is hydrogen, $R^1$ is $SR^3$, and $R^3$ represents tetrazole, substituted tetrazole, or triazole, under conditions well known in the art. For example, the compound of Formula Ia, wherein $R^2$ is hydrogen, $R^4$ is $SR^7$, and $R^7$ represents tetrazole, substituted tetrazole, or triazole, is dissolved in a suitable organic solvent such as methanol, and treated with an excess of a suitable base. Examples of suitable bases include aqueous lithium hydroxide, sodium hydroxide, potassium hydroxide, and the like, with lithium hydroxide being preferred. The reaction is stirred for about 10–20 hours. The reaction mixture is then neutralized to pH 6 with 1N HCl and concentrated under vacuum to provide the crude compound of Formula I, wherein $R^2$ is hydrogen, $R^1$ is $SR^3$, and $R^3$ represents tetrazole, substituted tetrazole, or triazole. This material can then be purified by techniques well known in the art, such as cation exchange chromatography eluting with THF/water followed by 10% pyridine in water to provide the purified compound of Formula I.

In Scheme IV, Step H, compound (13) or compound (14) (as described previously in Scheme IV, Step D above) is deprotected and hydrolyzed concomitantly to provide the compound of Formula I, wherein $R^2$ is hydrogen, $R^1$ is $SR^3$, and $R^3$ represents tetrazole, substituted tetrazole, or triazole. For example, a solution of compound (13) or compound (14) dissolved in 5N HCl is heated to reflux (90–95° C.) for about 15–20 hours. The reaction mixture is then allowed to cool to room temperature and concentrated in vacuo to provide the compound of Formula I, wherein $R^2$ is hydrogen, $R^1$ is $SR^3$, and $R^3$ represents tetrazole, substituted tetrazole, or triazole. The compound of Formula I can then be purified by techniques well known in the art, such as cation exchange chromatography eluting with THF/water followed by 10% pyridine in water to provide the purified compound of Formula I.

In Scheme IV, Step I, the compound of Formula I, wherein $R^2$ is hydrogen, $R^1$ is $SR^3$, and $R^3$ represents tetrazole, substituted tetrazole, or triazole, can be esterified, under conditions well known in the art, to provide the compound of Formula Ia, wherein $R^2$ is hydrogen, $R^4$ is $SR^7$, and $R^7$ represents tetrazole, substituted tetrazole, or triazole. For example, the compound of Formula I is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78–85° C.) for about 15–25 hours. The reaction mixture concentrated under vacuum to provide the crude compound of Formula Ia, wherein $R^2$ is hydrogen, $R^4$ is $SR^7$, and $R^7$ represents tetrazole, substituted tetrazole, or triazole. This material can then be purified by techniques well known in the art, such as cation exchange chromatography eluting with methanol/water followed by 2N ammonia in ethanol to provide the purified compound of Formula Ia.

Scheme V provides procedures for the synthesis of compounds of Formula I, wherein $R^1$ represents $SR^3$, $R^2$ represents hydrogen, and $R^3$ represents $(C_1-C_4)$alkyl or $(C_1-C_4)$alkyl-$CO_2H$.

lyzed under conditions well known in the art. This material can then be concentrated and purified by techniques well known in the art as described in Scheme I, Step F to provide the purified compound of Formula I, wherein wherein $R^2$

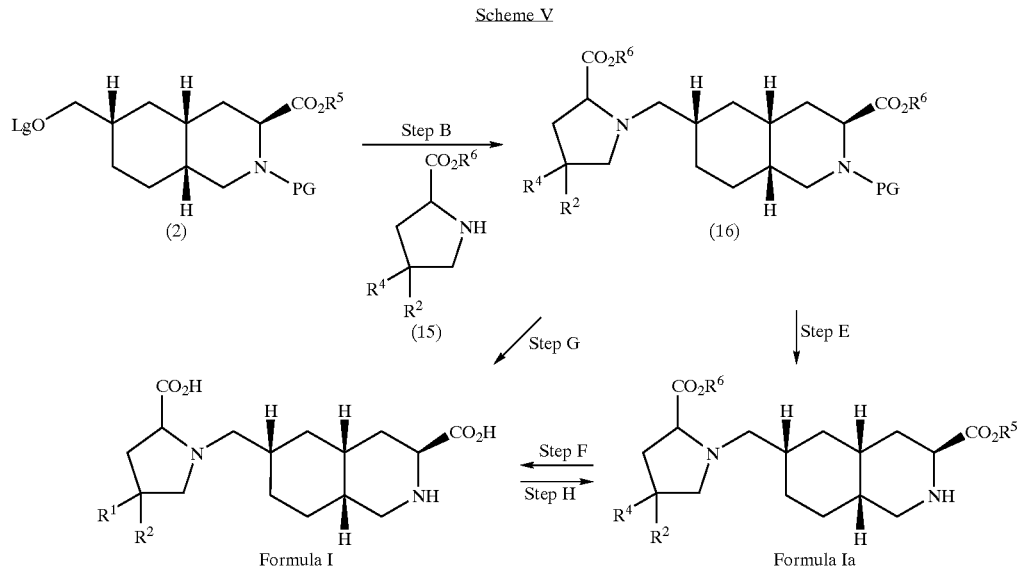

Scheme V

In Scheme V, Step B, the intermediate (2) (prepared as described in Scheme I) is treated under standard conditions with a compound of formula (15), wherein $R^2$ represents hydrogen, $R^4$ represents $SR^7$, and $R^7$ represents $(C_1-C_4)$alkyl or $(C_1-C_4)$alkyl-$CO_2R^8$, to provide the compound of structure (16). For example, a solution of compound (2), dissolved in a suitable organic solvent such as acetonitrile is treated with about 1.4 equivalents of a compound of formula (15), such as ethyl 2S,4S, 4-ethoxycarbonylmethylsulfanylpyrrolidine2-carboxylate, followed by about 1.5 equivalents of potassium carbonate. The reaction mixture is heated at 80° C. and stirred for about 72 hours. The compound of structure (16), wherein $R^2$ represents hydrogen, $R^4$ represents $SR^7$, and $R^7$ represents $(C_1-C_4)$alkyl or $(C_1-C_4)$alkyl-$CO_2R^8$, is then isolated using standard procedures. For example, the reaction mixture is washed with water, the organic layer separated and dried over anhydrous sodium sulfate, filtered, and concentrated under vacuum to provide crude compound (16). Column chromatography can then be performed on silica gel with a suitable eluent such as 10–50% ethyl acetate/hexane to provide the purified compound (16), wherein $R^2$ represents hydrogen, $R^4$ represents $SR^7$, and $R^7$ represents $(C_1-C_4)$alkyl or $(C_1-C_4)$alkyl-$CO_2R^8$.

In Scheme V, Step E, following the procedures as described in Scheme I, Step E, compound (16) is deprotected under standard conditions well known in the art to provide the compound of Formula Ia, wherein $R^2$ represents hydrogen, $R^4$ represents $SR^7$, and $R^7$ represents $(C_1-C_4)$alkyl or $(C_1-C_4)$alkyl-$CO_2R^8$. The material can then be concentrated and purified by procedures well known in the art as described in Scheme I, Step E, to provide the purified compound of Formula Ia.

In Scheme V, Step F, following the procedures as described in Scheme I, Step F, the compound of Formula Ia is hydrolyzed to the compound of Formula I, wherein wherein $R^2$ represents hydrogen, $R^1$ represents $SR^3$, and $R^3$ represents $(C_1-C_4)$alkyl or $(C_1-C_4)$alkyl-$CO_2H$, is hydrorepresents hydrogen, $R^1$ represents $SR^3$, and $R^3$ represents $(C_1-C_4)$alkyl or $(C_1-C_4)$alkyl-$CO_2H$.

In Scheme V, Step G, following the procedures as described in Scheme I, Step G, compound (16)(as described above) is deprotected and hydrolyzed concomitantly to provide the compound of Formula I, wherein $R^2$ represents hydrogen, $R^1$ represents $SR^3$, and $R^3$ represents $(C_1-C_4)$alkyl or $(C_1-C_4)$alkyl-$CO_2H$. The compound of Formula I can then be concentrated and purified by techniques well known in the art to provide the purified compound of Formula I, wherein $R^2$ represents hydrogen, $R^1$ represents $SR^3$, and $R^3$ represents $(C_1-C_4)$alkyl or $(C_1-C_4)$alkyl-$CO_2H$.

In Scheme V, Step H, the compound of Formula I can be esterified, under conditions well known in the art as described in Scheme I, Step H, to provide the compound of Formula Ia, wherein $R^2$ represents hydrogen, $R^4$ represents $SR^7$, and $R^7$ represents $(C_1-C_4)$alkyl or $(C_1-C_4)$alkyl-$CO_2R^8$. For example, the compound of Formula I is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78–85° C.) for about 15–25 hours. The reaction mixture is concentrated under vacuum to provide the crude compound of Formula Ia, wherein $R^2$ represents hydrogen, $R^4$ represents $SR^7$, and $R^7$ represents $(C_1-C_4)$alkyl or $(C_1-C_4)$alkyl-$CO_2R^8$. This material can then be purified by techniques well known in the art, such as cation exchange chromatography eluting with methanol/water followed by 2N ammonia in ethanol to provide the purified compound of Formula Ia.

Scheme VI provides compounds of Formula I, wherein $R^1$ represents hydrogen or hydroxy and $R^2$ represents hydrogen.

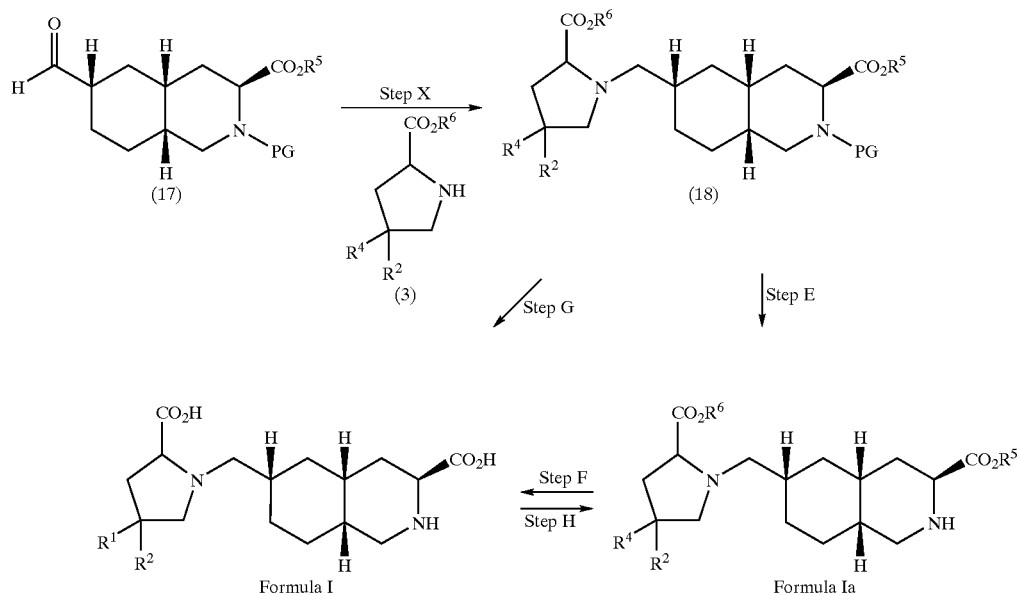

Scheme VI

In Scheme VI, Step I, the intermediate (17) is treated under standard reductive amination conditions with a compound of formula (3), wherein $R^2$ represents hydrogen and $R^4$ represents hydrogen or hydroxy, to provide the compound of structure (18). For example, a solution of compound (17), dissolved in a suitable organic solvent such as THF is treated with 1.0 equivalents of a compound of formula (3), such as 4-hydroxy-L-proline ethyl ester, followed by about 1.4 equivalents of sodium triacetoxyborohydride and about 1.0 equivalent of acetic acid. The reaction mixture is stirred at room temperature for about 18 hours. The compound (18), wherein $R^2$ represents hydrogen and $R^4$ represents hydrogen or hydroxy, is then isolated using standard procedures. For example, the reaction mixture is partitioned between 3:1 $CHCl_3$/IPA and water, the organic layer is separated and dried over anhydrous sodium sulfate, filtered, and concentrated under vacuum to provide crude compound (18), wherein $R^2$ represents hydrogen and $R^4$ represents hydrogen or hydroxy. Column chromatography can then be performed on silica gel with a suitable eluent such as 75% ethyl acetate/hexane to provide the purified compound (18).

In Scheme VI, Step E, following the procedures as described in Scheme I, Step E, compound (18) is deprotected under standard conditions well known in the art to provide the compound of Formula Ia, wherein $R^2$ represents hydrogen and $R^4$ represents hydrogen or hydroxy. The material can then be purified by techniques well known n the art as described in Scheme I, Step E, to provide the purified compound of Formula Ia, wherein $R^2$ represents hydrogen and $R^4$ represents hydrogen or hydroxy.

In Scheme VI, Step F, following the procedures as described in Scheme I, Step F, the compound of Formula Ia is hydrolyzed to the compound of Formula I, wherein $R^2$ represents hydrogen and $R^1$ represents hydrogen or hydroxy, under conditions well known in the art. This material may then be concentrated and purified by techniques well known in the art as described in Scheme I, Step F, to provide the purified compound of Formula I, wherein $R^2$ represents hydrogen and $R^1$ represents hydrogen or hydroxy.

In Scheme VI, Step G, following the procedures as described in Scheme I, Step G, compound (18) is deprotected and hydrolyzed concomitantly to provide the compound of Formula I, wherein $R^2$ represents hydrogen and $R^1$ represents hydrogen or hydroxy. The compound of Formula I can then be concentrated and purified by techniques well known in the art as described in Scheme I, Step G, to provide the purified compound of Formula I, wherein $R^2$ represents hydrogen and $R^1$ represents hydrogen or hydroxy.

In Scheme VI, Step H, following the procedures as described in Scheme I, Step H, the compound of Formula I can be esterified, under conditions well known in the art as described in Scheme I, Step H, to provide the compound of Formula Ia. For example, the compound of Formula I, wherein $R^2$ represents hydrogen and $R^1$ represents hydrogen or hydroxy. This material can then be concentrated and purified by techniques well known in the art as described in Scheme I, Step H such as cation exchange chromatography eluting with methanol/water followed by 2N ammonia in ethanol to provide the purified compound of Formula Ia, wherein $R^2$ represents hydrogen and $R^4$ represents hydrogen or hydroxy.

Scheme VII provides procedures for the synthesis of compounds of Formula II, wherein $R^9$ is fluorine or hydroxy, and $R^{10}$ is hydrogen.

Scheme VII

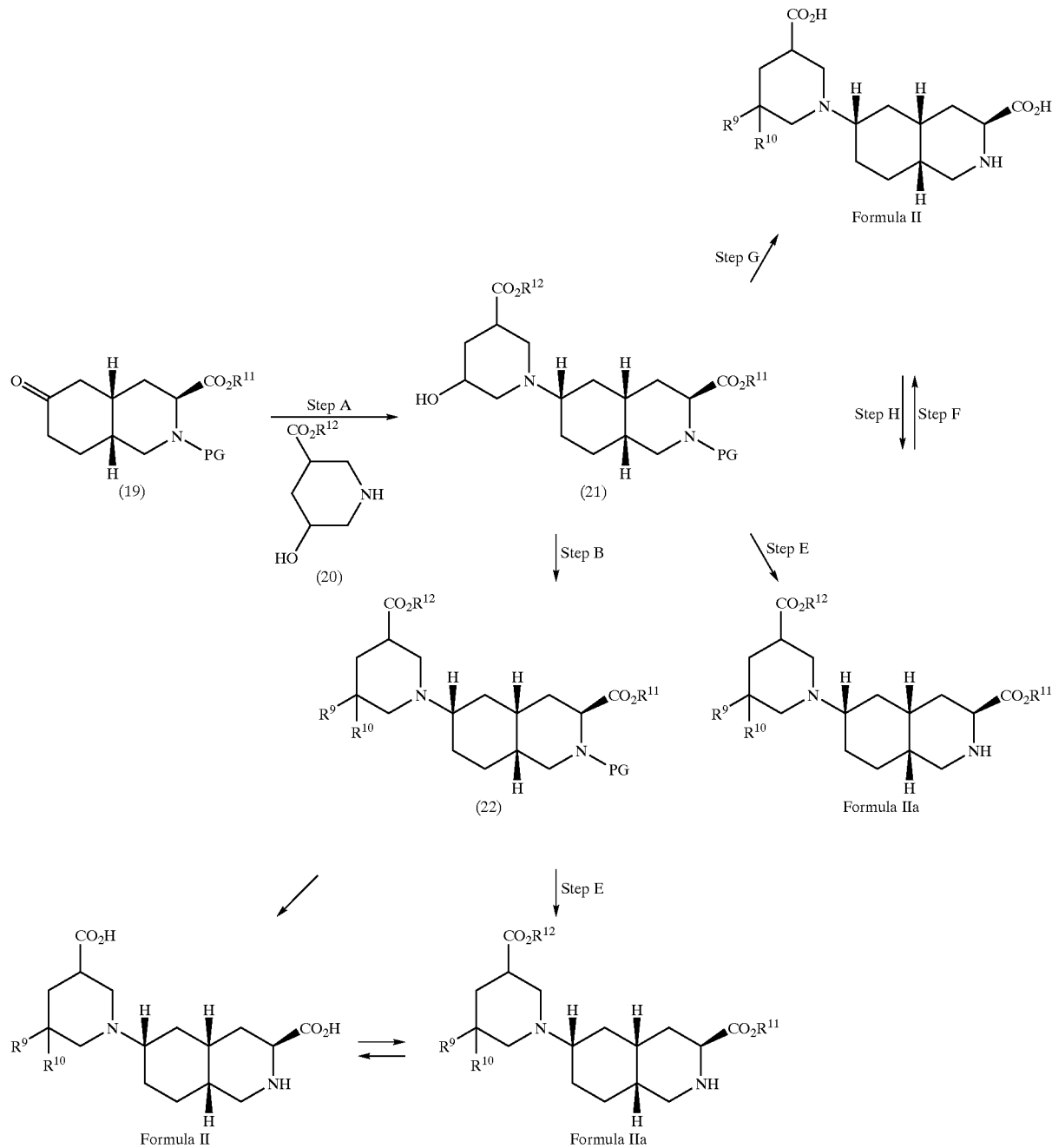

In Scheme VII, Step A, the intermediate (19) is treated under standard reductive amination conditions with a compound of formula (20), to provide the compound of structure (21). For example, a solution of compound (19) (ethyl-2-methoxycarbonyl-6-oxodecahydroisoquioline 3-carboxylate), dissolved in a suitable organic solvent such as THF is treated with 0.5 equivalents of a compound of formula (3), such as 3R, 5S ethyl 5-hydroxypiperidine-3-carboxylate, followed by about 1.0 equivalents of sodium triacetoxyborohydride and 1.0 equivalent of acetic acid. The reaction mixture is stirred at room temperature for about 72 hours. The compound (21) is then isolated using standard procedures. For example, the reaction mixture is partitioned between 3:1 $CHCl_3$/IPA and water, the organic layer is separated and dried over anhydrous sodium sulfate, filtered, and concentrated under vacuum to provide crude compound (21). Column chromatography can then be performed on silica gel with a suitable eluent such as 5% MeOH/ methylene chloride to provide the purified compound (21).

In Scheme VII, Step E, the compound of structure (21) can be deprotected directly under standard conditions to provide the compound of Formula IIa, wherein for purposes of the present step, $R^9$ represents hydroxy and $R^{10}$ represents hydrogen. For example, when PG is a methoxycarbonyl protecting group, compound (21) is dissolved in a suitable organic solvent such as dichloromethane under an atmosphere of nitrogen and treated with trimethylsilyl iodide. The reaction mixture is allowed to warm to room temperature and stirred for about 10–20 hours. The reaction is quenched by addition of saturated aqueous $NaHCO_3$. The aqueous layer is then extracted 2–6 times with dichloromethane. The organics are then combined, washed with a 1N solution of sodium thiosulfate, dried over magnesium sulfate, filtered, and concentrated in vacuo to provide the compound of Formula IIa, wherein $R^9$ represents hydroxy and $R^{10}$ represents hydrogen. The material can then be purified by chromatography on silica gel with a suitable eluent such as methanol/dichoromethane, to provide the purified compound of Formula IIa, wherein $R^9$ represents hydroxy and $R^{10}$ represents hydrogen.

In Scheme VII, Step F, the compound of Formula IIa is hydrolyzed to the compound of Formula II, wherein $R^9$ represents hydroxy and $R^{10}$ represents hydrogen, under conditions well known in the art. For example, the compound of Formula IIa is dissolved in a suitable organic solvent such as methanol, and treated with an excess of a suitable base. Examples of suitable bases include aqueous lithium hydroxide, sodium hydroxide, potassium hydroxide, and the like, with lithium hydroxide being preferred. The reaction is stirred for about 10–20 hours. The reaction mixture is then neutralized to pH 6 with 1N HCl and concentrated under vacuum to provide the crude compound of Formula II, wherein $R^9$ represents hydroxy and $R^{10}$ represents hydrogen. This material is then purified by techniques well known in the art, such as cation exchange chromatography eluting with THF/water followed by 10% pyridine in water to provide the purified compound of Formula II, wherein $R^9$ represents hydroxy and $R^{10}$ represents hydrogen.

In Scheme VII, Step G, compound (21) is deprotected and hydrolyzed concomitantly to provide the compound of Formula II, wherein $R^9$ represents hydroxy and $R^{10}$ represents hydrogen. For example, a solution of compound (21) dissolved in 5N HCl is heated to reflux (90–95° C.) for about 15–20 hours. The reaction mixture is then allowed to cool to room temperature and concentrated in vacuo to provide the compound of Formula II, wherein $R^9$ represents hydroxy and $R^{10}$ represents hydrogen. The compound of Formula II can then be purified by techniques well known in the art, such as cation exchange chromatography eluting with tetrahydrofuran/water followed by 10% pyridine/water to provide the purified compound of Formula II, wherein $R^9$ represents hydroxy and $R^{10}$ represents hydrogen.

In Scheme VII, Step H, the compound of Formula II can be esterified, under conditions well known in the art, to provide the compound of Formula IIa, wherein $R^9$ represents hydroxy and $R^{10}$ represents hydrogen. For example, the compound of Formula II is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78–85° C.) for about 15–25 hours. The reaction mixture is concentrated under vacuum to provide the crude compound of Formula IIa. This material can then be purified by techniques well known in the art, such as cation exchange chromatography eluting with methanol/water followed by 2N ammonia in ethanol to provide the purified compound of Formula IIa, wherein $R^9$ represents hydroxy and $R^{10}$ represents hydrogen.

Alternatively, in Step B, Compound (21) from Step A above can be converted, under standard fluorination conditions well known in the art, to provide compound (22), wherein $R^9$ represents fluorine and $R^{10}$ represents hydrogen. For example, in Scheme VII, Step B, the compound of structure (21), is treated with diethylamino sulfur trifluoride to yield the intermediate of structure (22) wherein for purposes of the present scheme, $R^9$ represents fluorine and $R^{10}$ represents hydrogen. For example, to a mixture of compound (21), cooled to about −78° C. in $CH_2Cl_2$, is added dropwise diethylamino sulfur trifluoride. The reaction is allowed to warm to room temperature, stirred for about 48 hours, and quenched by addition of MeOH. The compound of structure (22) wherein for purposes of the present scheme, $R^9$ represents fluorine and $R^{10}$ represents hydrogen, is then isolated under standard conditions. For example, compound (22) is first concentrated under vacuum, then the residue partitioned between 3:1 $CHCl_3$/IPA and aqueous $NaHCO_3$. The aqueous layer is then extracted with 3:1 $CHCl_3$/IPA and the combined organics dried over $MgSO_4$, filtered, and concentrated under vacuum to provide the concentrated compound (22) wherein for purposes of the present scheme, $R^9$ represents fluorine and $R^{10}$ represents hydrogen. This material may then be purified by techniques well known in the art such as chromatography on silica gel with a suitable eluent, such as 25–50% EtOAc/hexane to provide the purified compound of structure (22).

Compound (22) can then be deprotected and hydrolyzed under standard conditions well known in the art, as previously described herein for Scheme VII, Steps E and F above, to provide the compounds of Formula IIa and Formula II, wherein $R^9$ represents fluorine and $R^{10}$ represents hydrogen. Alternatively, the compound of structure (22) may be deprotected and hydrolyzed concomitantly under standard conditions, as previously described herein for Scheme VII, Step G, to provide the compound of Formula II wherein $R^9$ represents fluorine and $R^{10}$ represents hydrogen. The compound of Formula II may then be esterified, again under standard conditions well known in the art as described previously for Scheme VII, Step H, to provide the compound of Formula IIa, wherein $R^9$ represents fluorine and $R^{10}$ represents hydrogen.

In order to obtain compounds of Formula II, wherein $R^9$ represents fluorine or hydroxy and $R^{10}$ represents hydrogen, and wherein the 3,5 substituents of the piperidine moiety are trans in relation to each other, the C-5 hydroxy group of structure (21) may be inverted via a standard Mitsunobu reaction, as shown in Scheme VII(a)

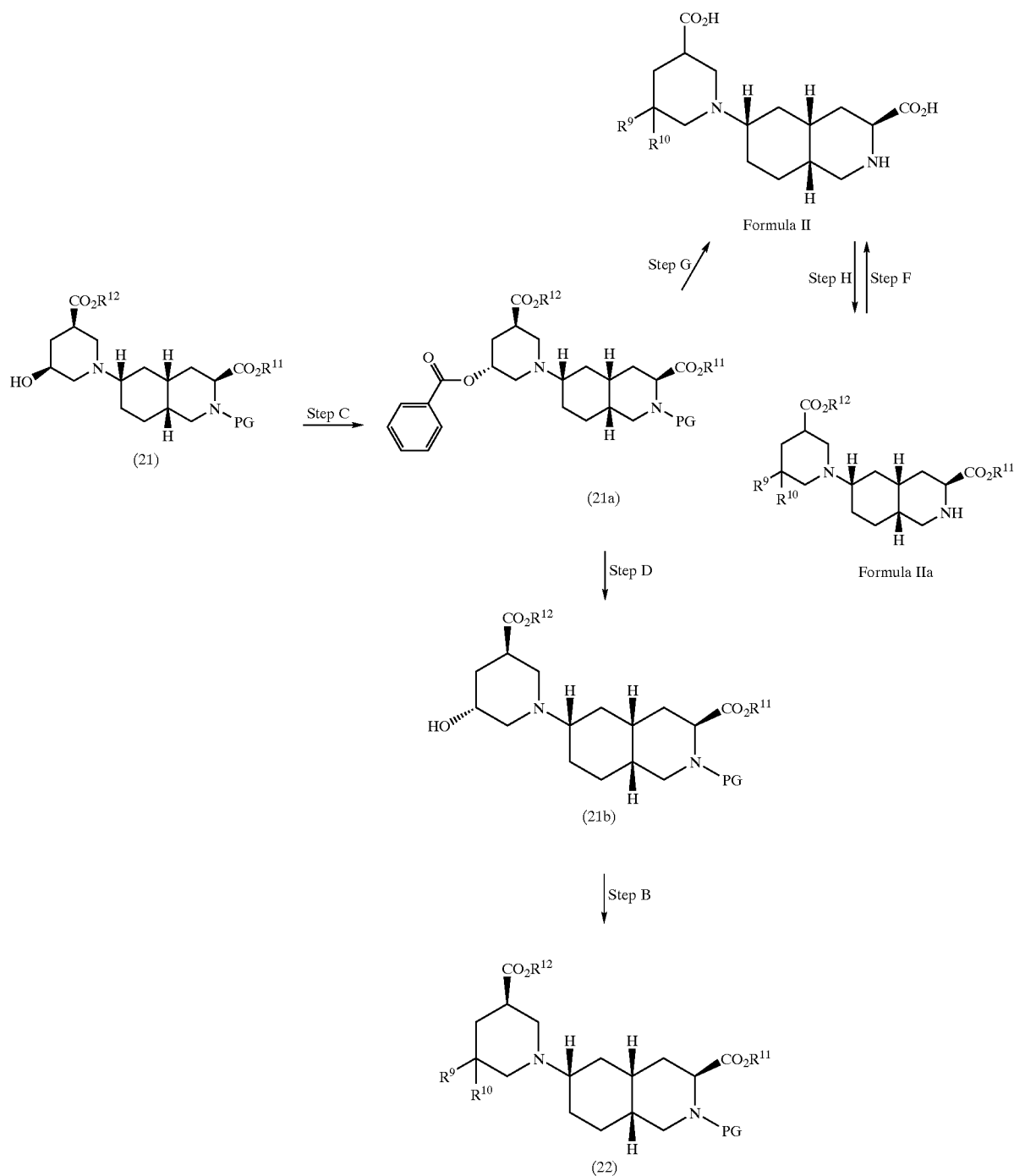

Scheme VII(a)

For example, In Scheme VII(a), Step C, when PG is a methoxycarbonyl protecting group, compound (21), dissolved in a suitable organic solvent such as tetrahydrofuran, is cooled to 0° C. and charged with 4 equivalents of triphenylphosphine followed by 4 equivalents of benzoic acid. The reaction mixture is allowed to warm to room temperature and stirred for about 48 hours. The material is then loaded onto an SCX cation exchange cartridge, and eluted with ethanol, followed by 2 M ammonia in ethanol. The material can then be purified by chromatography on silica gel with a suitable eluent such as methanol/dichloromethane, to provide the purified compound of structure (21a).

In Scheme VII(a), Step G, the compound of structure (21a) may be deprotected and hydrolyzed concomitantly under standard conditions, as described in Scheme VII, Step G above, to provide the compound of Formula II, wherein R9 represents hydroxy, R10 represents hydrogen, and wherein the C-3 and C-5 substituents of the piperidine moiety of Formula II are trans in relation to each other.

Alternatively, in Scheme VII(a), Step D, the C-5 benzoyl ester group of compound (21a) is hydrolyzed to the C-5 hydroxy group as shown in structure (21b). Compound (21b) is then converted, under standard fluorination conditions, to the compound of structure (22), wherein R9 is flourine, R10 is hydrogen, and the C-3 and C-5 substituents of the piperidine moiety of structure (22) are trans in relation to each other For example, in Scheme VII(a), Step D, compound (21a) is dissolved in an appropriate solvent such as ethanol, to which concentrated sulfuric acid (approximately 3 equivalents) is added. The reaction is heated at 80° C. for a period of about 72 hours, then concentrated in vacuo. The residue is partitioned between 3:1 $CHCl_3$/IPA and aqueous sodium hydroxide. The aqueous layer is then extracted with 3:1 $CHCl_3$/IPA and the combined organics dried over $MgSO_4$, filtered, and concentrated under vacuum to provide compound (21b) wherein the C-3 and C-5 substituents of the piperidine moiety are trans in relation to each other. This material may then be purified by techniques well known in the art such as chromatography on silica gel with a suitable eluent, such as 30% methanol/methylene chloride to provide the purified compound of structure (21b).

Compound (21b) may then be converted to compound (22), wherein for purposes of the present scheme $R^9$ represents flurione, $R^{10}$ represents hydrogen, and wherein the C-3 and C-5 substituents of the piperidine moiety are trans in relation to each other, under the same standard fluorination conditions as described in Scheme VII, Step B.

Compound (22) of the present scheme may then be deprotected and hydrolyzed under standard conditions well known in the art, as previously described herein for Scheme VII, Steps E and F above, to provide the compounds oaf Formula II and IIa, wherein $R^9$ represents flurione, $R^{10}$ represents hydrogen, and wherein the C-3 and C-5 substituents of the piperidine moiety are trans in relation to each other. Alternatively, the compound of structure (22) may be deprotected and hydrolyzed concomitantly under standard conditions, as previously described herein for Scheme VII, Step G, to provide the compound of Formula II wherein $R^9$ represents fluorine, $R^{10}$ represents hydrogen, and and wherein the C-3 and C-5 substituents of the piperidine moiety are trans in relation to each other. The compound of Formula II may then be esterified, again under standard conditions well known in the art as described previously for Scheme VII, Step H, to provide the compounds of Formula IIa, wherein $R^9$ represents fluorine, $R^{10}$ represents hydrogen, and and wherein the C-3 and C-5 substituents of the piperidine moiety are trans in relation to each other.

Scheme VIII provides procedures for the synthesis of compounds of Formula II, wherein $R^9$ and $R^{10}$ each independently represents fluorine, or $R^9$ and $R^{10}$, together, represent an oxo group.

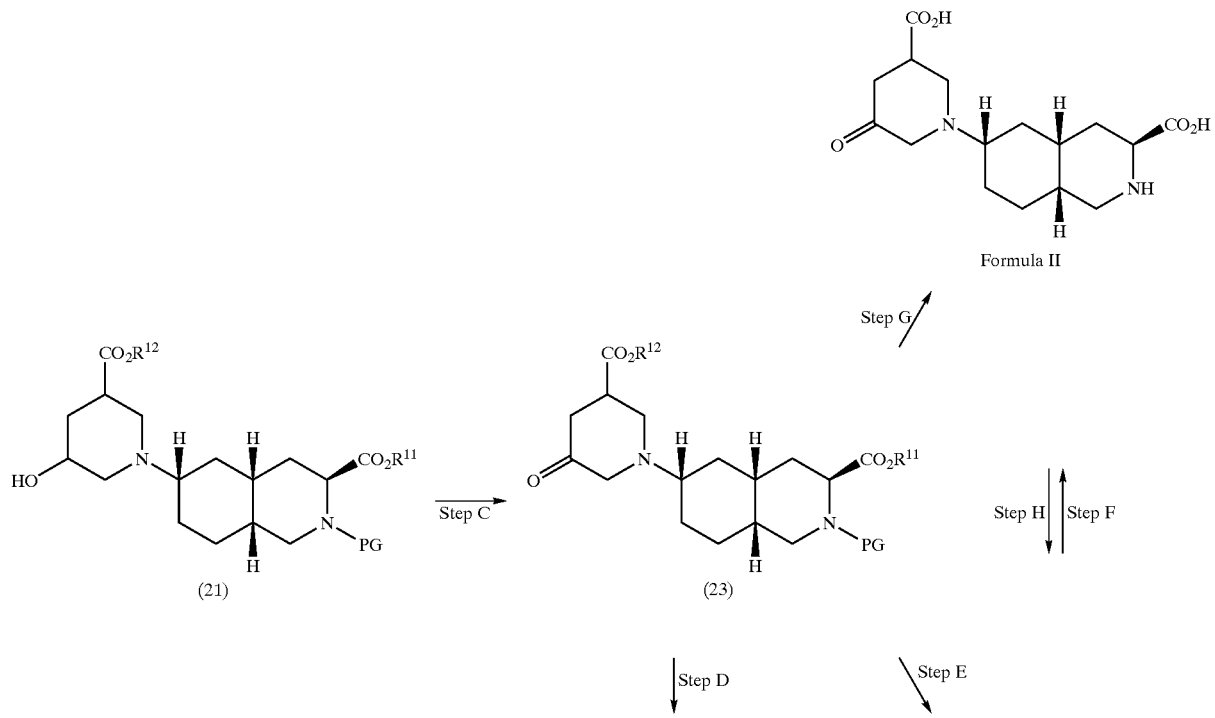

Scheme VIII

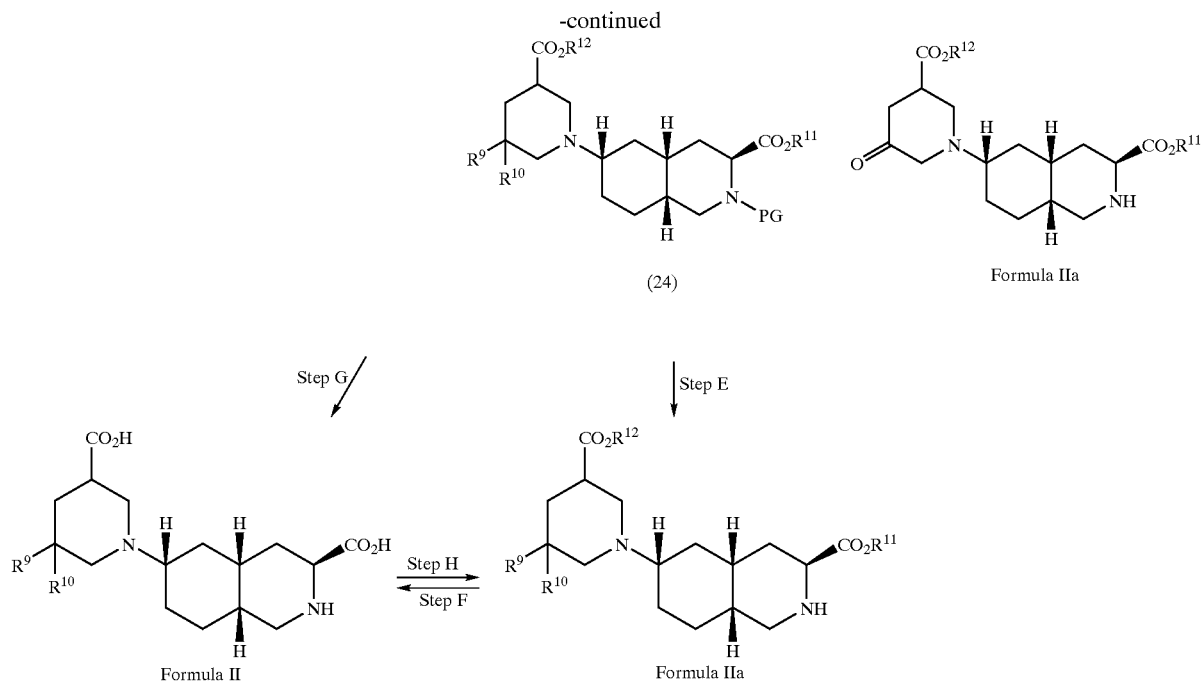

In Scheme VIII, Step C, treatment of compound (21) under standard oxidizing conditions provides the ketone intermediate of compound (23). For example, compound (21) can be added to a mixture of 1.3 equivalents of oxalyl chloride and 2.5 equivalents of DMSO at −78° C., followed by addition of approx. 5.0 equivalents of triethylamine, and subsequent warming of the reaction to room temperature. The reaction mixture is partitioned between water and an organic solvent such as methylene chloride, and the aqueous layer extracted 2–6 times with methylene chloride. The organic layers are combined, dried over anhydrous sodium sulfate, filtered, and concentrated under vacuum to provide the ketone compound of structure (23). Compound (23) can then be purified by chromatography on silica gel with a suitable eluent such as ethyl acetate/hexanes or methanol/chloroform.

In Scheme VIII, Step E, compound (23) is deprotected under standard conditions well known in the art to provide the compound of Formula IIa, wherein $R^9$ and $R^{10}$ together represent an oxo group. For example, when PG is a methoxycarbonyl protecting group, compound (23) is dissolved in a suitable organic solvent such as dichloromethane under an atmosphere of nitrogen and treated with trimethylsilyl iodide. The reation mixture is allowed to warm to room temperature and stirred for about 10–20 hours. The reaction is quenched by addition of saturated aqueous $NaHCO_3$. The aqueous layer is then extracted 2–6 times with dichloromethane. The organics are then combined, washed with a 1N solution of sodium thiosulfate, dried over magnesium sulfate, filtered, and concentrated in vacuo to provide the compound of Formula IIa, wherein $R^9$ and $R^{10}$ together represent an oxo group. This material can then be purified by chromatography on silica gel with a suitable eluent such as methanol/dichloromethane, to provide the purified compound of Formula IIa, wherein $R^9$ and $R^{10}$ together represent an oxo group.

In Scheme VIII, Step F, the compound of Formula IIa is hydrolyzed to the compound of Formula II, wherein $R^9$ and $R^{10}$ together represent an oxo group, under conditions well known in the art For example, the compound of Formula IIa is dissolved in a suitable organic solvent such as methanol, and treated with an excess of a suitable base. Examples of suitable bases include aqueous lithium hydroxide, sodium hydroxide, potassium hydroxide, and the like, with lithium hydroxide being preferred. The reaction is stirred for about 10–20 hours. The reaction mixture is then neutralized to pH 6 with 1N HCl and concentrated under vacuum to provide the crude compound of Formula II, wherein $R^9$ and $R^{10}$ together represent an oxo group. This material can then be purified by techniques well known in the art, such as cation exchange chromatography eluting with tetrahydrofuran/water followed by 10% pyridine/water to provide the purified compound of Formula II, wherein $R^9$ and $R^{10}$ together represent an oxo group.

In Scheme II, Step G, compound (23) may be deprotected and hydrolyzed concomitantly to provide the compound of Formula II, wherein $R^9$ and $R^{10}$ together represent an oxo group. For example, a solution of compound (23) dissolved in 5N HCl is heated to reflux (90–95° C.) for about 15–20 hours. The reaction mixture is then allowed to cool to room temperature and concentrated in vacuo to provide the compound of Formula II, wherein $R^9$ and $R^{10}$ together represent an oxo group. The compound of Formula II can then be purified by techniques well known in the art, such as cation exchange chromatography eluting with tetrahydrofuran/water followed by 10% pyridine/water to provide the purified compound of Formula II, wherein $R^9$ and $R^{10}$ together represent an oxo group.

In Scheme VIII, Step H, the compound of Formula II, wherein $R^9$ and $R^{10}$ together represent an oxo group, can be esterified, under conditions well known in the art, to provide the compound of Formula IIa, $R^9$ and $R^{10}$ together represent an oxo group. For example, the compound of Formula II is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78–85° C.) for about 15–25 hours. The reaction mixture is concentrated under vacuum to provide the crude compound of Formula IIa, wherein $R^9$ and $R^{10}$ together represent an oxo group. This material can then be purified by techniques well known in the art, such as cation exchange chromatography eluting with methanol/water followed by 2N ammonia in ethanol to provide the purified compound of Formula IIa, wherein $R^9$ and $R^{10}$ together represent an oxo group.

Alternatively, in Scheme VIII, Step D the compound of structure (23) is converted to the intermediate of structure (24), wherein for purposes of the present step, $R^9$ and $R^{10}$ each independently represent fluorine. Procedures for synthesizing compounds of structure (24), wherein $R^9$ and $R^{10}$ both represent fluorine, are provided herein essentially as described in Scheme I, Step D supra.

Compound (24) can then be deprotected and hydrolyzed under standard conditions well known in the art, as previously described herein for Scheme VIII, Steps B and F above, to provide the compounds of Formula IIa and Formula II, wherein $R^9$ and $R^{10}$ each independently represent fluorine. Alternatively, the compound of structure (24) may be deprotected and hydrolyzed concomitantly under standard conditions, as previously described herein for Scheme VIII, Step G, to provide the compound of Formula II wherein $R^9$ and $R^{10}$ each independently represent fluorine. The compound of Formula II may then be esterified, again under standard conditions well known in the art as described previously for Scheme VIII, Step H, to provide the compound of Formula IIa, wherein $R^9$ and $R^{10}$ each independently represent fluorine.

Scheme IX provides procedures for the synthesis of compounds of Formula II, wherein $R^9$ represents tetrazole or a group of the formula:

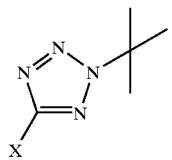

wherein X represents $(C_1–C_4)$alkyl or phenyl, and $R^{10}$ represents hydrogen.

Scheme IX

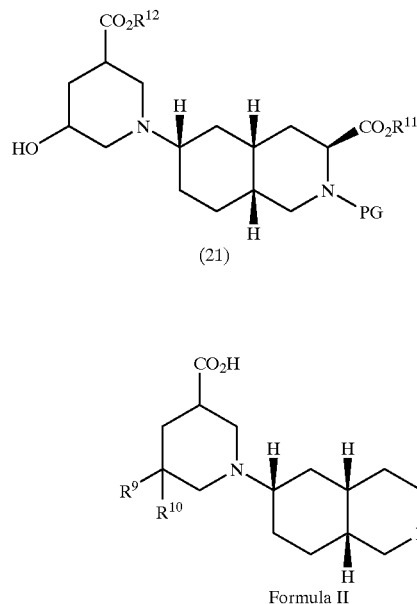

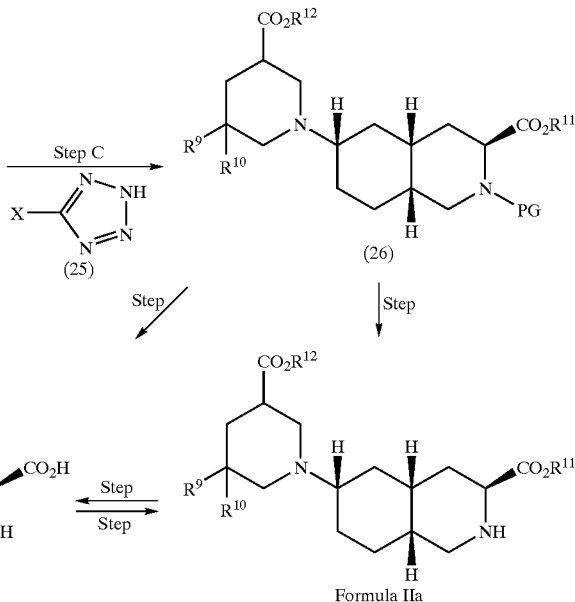

In Scheme IX, Step C, compound (21) is treated with a compound of structure (25), wherein X represents hydrogen, $(C_1–C_4)$alkyl, or phenyl, in the presence of triphenylphosphine and DEAD to give the compound of structure (26), wherein $R^9$ is tetrazole or a group of the structure(a):

Structure (a)

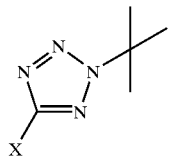

(wherein X for the purposes of Structure (a) represents $(C_1–C_4)$alkyl or phenyl) and $R^{10}$ represents hydrogen. For example, a solution compound (21) about 1–1.4 equivalents of compound (25) (wherein X represents hydrogen, $(C_1–C_4)$ alkyl, or phenyl) and about 1–1.4 equivalents of triphenylphosphine in tetrahydrofuran is cooled to 0° C. Diethyl azodicarboxylate (1–1.4 equivalents) is added and the reaction is allowed to warm to room temperature then stirred for about 72 hours. The reaction may then be purified by chromatography on SCX resin with a suitable eluent such as 2 N ammonia in ethanol, to provide compound (26), wherein $R^9$ represents tetrazole or group of Structure (a) as provided herein above. Compound (26) can then be further purified by chromatography on silica gel with a suitable eluent such as ethyl acetate/hexanes.

In Scheme IX, Step E, compound (26), wherein $R^9$ represents tetrazole or group of Structure (a) (as provided herein in Scheme IX, Step C above), is deprotected under standard conditions well known in the art to provide the compound of Formula IIa, wherein $R^9$ represents tetrazole or group of Structure (a) (as provided herein in Scheme IX, Step C above). For example, when PG is a methoxycarbonyl protecting group, compound (26) is dissolved in a suitable organic solvent such as dichloromethane under an atmosphere of nitrogen and treated with trimethylsilyl iodide. The reation mixture is allowed to warm to room temperature and stirred for about 10–20 hours. The reaction is quenched by addition of saturated aqueous NaHCO$_3$. The aqueous layer is then extracted 2–6 times with dichloromethane. The organics are then combined, washed with a 1N solution of sodium thiosulfate, dried over magnesium sulfate, filtered, and concentrated in vacuo to provide the compound of Formula IIa, wherein $R^9$ represents tetrazole or group of Structure (a) (as provided herein in Scheme IX, Step C above). The material can then be purified by chromatography on silica gel with a suitable eluent such as methanol/dichoromethane, to provide the purified compound of Formula IIa, wherein $R^9$ represents tetrazole or group of Structure (a) (as provided herein in Scheme IX, Step C above).

In Scheme IX, Step F, the compound of Formula IIa from Step E above, is hydrolyzed under conditions well known in the art to the compound of Formula II, wherein $R^9$ represents tetrazole or group of Structure (a) (as provided herein in Scheme IX, Step C above). For example, the compound of Formula IIa, from Scheme IX, Step E, is dissolved in a suitable organic solvent such as methanol, and treated with an excess of a suitable base. Examples of suitable bases include aqueous lithium hydroxide, sodium hydroxide, potassium hydroxide, and the like, with lithium hydroxide being preferred. The reaction is stirred for about 10–20 hours. The reaction mixture is then neutralized to pH 6 with 1N HCl and concentrated under vacuum to provide the crude compound of Formula II, wherein $R^9$ represents tetrazole or group of Structure (a) (as provided herein in Scheme IX, Step C above). This material may then be purified by techniques well known in the art, such as cation exchange chromatography eluting with tetrahydrofuran/water followed by 10% pyridine/water to provide the purified compound of Formula II, wherein $R^9$ represents tetrazole or group of Structure (a) (as provided herein in Scheme IX, Step C above).

In Scheme IX, Step G, compound (26) is deprotected and hydrolyzed concomitantly to provide the compound of Formula II, wherein $R^9$ represents tetrazole or group of Structure (a) (as provided herein in Scheme IX, Step C above). For example, a solution of compound (26) dissolved in 5N HCl is heated to reflux (90–95° C.) for about 15–20 hours. The reaction mixture is then allowed to cool to room temperature and concentrated in vacuo to provide the compound of Formula II, wherein $R^9$ represents tetrazole or group of Structure (a) (as provided herein in Scheme IX, Step C above). The compound of Formula II can then be purified by techniques well known in the art, such as cation exchange chromatography eluting with tetrahydrofuran/water followed by 10% pyrdine/water to provide the purified compound of Formula II, wherein $R^9$ represents tetrazole or group of Structure (a) (as provided herein in Scheme IX, Step C above).

In Scheme IX, Step H, the compound of Formula II can be esterified, under conditions well known in the art, to provide the compound of Formula II, wherein $R^9$ represents tetrazole or group of Structure (a) (as provided herein in Scheme IX, Step C above). For example, the compound of Formula II, wherein $R^9$ represents tetrazole or group of Structure (a) (as provided herein in Scheme IX, Step C above) is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78–85° C.) for about 15–25 hours. The reaction mixture is concentrated under vacuum to provide the crude compound of Formula IIa, wherein $R^9$ represents tetrazole or group of Structure (a) (as provided herein in Scheme IX, Step C above). This material can then be purified by techniques well known in the art, such as cation exchange chromatography eluting with methanol/water followed by 2N ammonia in ethanol to provide the purified compound of Formula IIa, where $R^9$ represents tetrazole or group of Structure (a) (as provided herein in Scheme IX, Step C above).

The compounds of Formula I may be synthesized by one of ordinary skill in the art from intermediates previously disclosed in the art. For example, synthesis of ethyl-6-hydroxymethyl-2-methoxycarbonyl-decahydroisoquinoline-3-carboxylate is provided in U.S. Pat. Nos. 5,356,902, issued Oct. 18, 1994 and 5,670,516, issued Sep. 23, 1997; synthesis of ethyl-6-bromomethyl-2-methoxycarbonyl-decahydroisoquinoline-3-carboxylate is provided in U.S. Pat. No. 5,670,516, issued Sep. 23, 1997; and synthesis of ethyl-6formyl-2-methoxycarbonyl-decahydroisoquinoline-3-carboxylate is provided in U.S. Pat. Nos. 5,356,902, issued Oct. 18, 1994 and 5,670,516, issued Sep. 23, 1997. These intermediates, in turn, may be synthesized from the common intermediate ethyl-2-methoxycarbonyl-6-oxodecahydroisoquinoline-3-carboxylate, the synthesis of which is provided in U.S. Pat. No. 4,902,695, U.S. Pat. No. 5,356,902, U.S. Pat. No. 5,446,051, and U.S. Pat. No. 5,670,516, the contents, all of which, are herein incorporated by reference. Likewise, the compounds of Formula II may also be synthesized from the same common intermediate, ethyl-2-methoxycarbonyl-6-oxodecahydroisoquinoline-3-carboxylate.

A route for the synthesis of the ethyl-2-methoxycarbonyl-6-oxodecahydroisoquinoline-3-carboxylate intermediate, useful for the synthesis of the compounds of the present invention, is shown in Scheme X below. This intermediate may be synthesized from a 2-methoxycarbonyl-6-oxodecahydroisoquinoline-3-carboxylic acid, the synthesis of which is described in U.S. Pat. No. 4,902,695, U.S. Pat. No. 5,446,051, and U.S. Pat. No. 5,356,902 (the contents of which are all herein incorporated by reference)

Scheme X

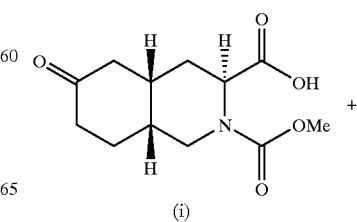

(i)

-continued

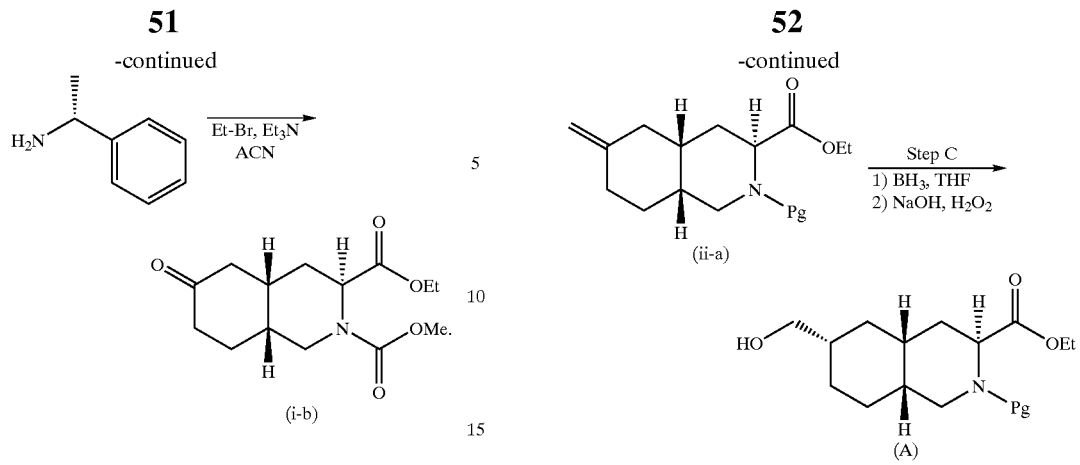

In Scheme X, Step A, the compound of structure (i) is esterified by reaction with a compound of formula Et-Br (where Et represents an ethyl group) to provide the intermediate of compound (i-b). For example 2-methoxycarbonyl-6-oxodecahydroisoquinoline-3-carboxylic acid is dissolved in acetonitrile and treated with triethylamine and bromoethane. The reaction is heated at 50° C. for about 3 hours, cooled and partitioned between 50:50 ethyl acetate/heptane and 1N HCl. The organic phase is isolated and washed 3 times with water, saturated sodium bicarbonate, brine, dried over anhydrous sodium sulfate, filtered, and concentrated under vacuum to provide ethyl-2-methoxycarbonyl-6-oxodecahydroisoquinoline-3-carboxylate, the compound of structure (i-b). This crude material may then be purified under standard conditions well known in the art. For example, the crude material is dissolved in 10% ethyl acetate/heptane and applied to a plug of silica gel (10 g in 10% ethyl acetate/heptane). The plug is eluted with, 10% ethyl acetate/heptane, 15% ethyl acetate/heptane, and 25% ethyl acetate/heptane. The eluents are combined and concentrated under vacuum to provide the purified compound of structure (i-b).

Routes for the synthesis of the ethyl-6-hydroxymethyl-2-methoxycarbonyl-decahydroisoquinoline-3-carboxylate intermediate, useful for the synthesis of the compounds of Formula I, are shown in Schemes XIa and XIb below.

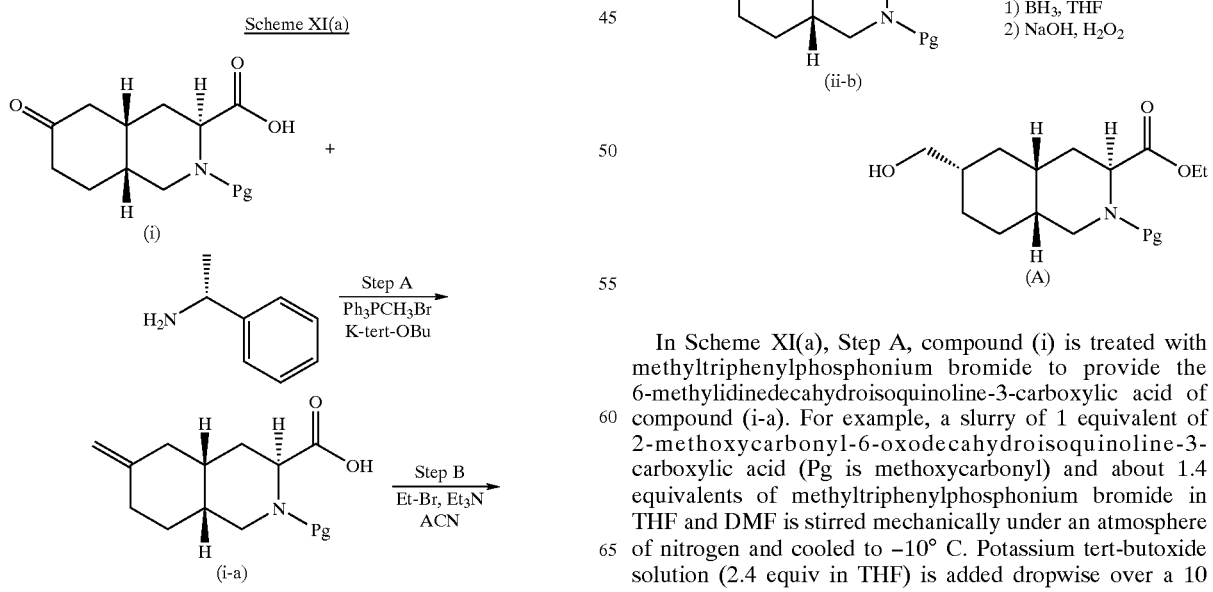

In Scheme XI(a), Step A, compound (i) is treated with methyltriphenylphosphonium bromide to provide the 6-methylidinedecahydroisoquinoline-3-carboxylic acid of compound (i-a). For example, a slurry of 1 equivalent of 2-methoxycarbonyl-6-oxodecahydroisoquinoline-3-carboxylic acid (Pg is methoxycarbonyl) and about 1.4 equivalents of methyltriphenylphosphonium bromide in THF and DMF is stirred mechanically under an atmosphere of nitrogen and cooled to −10° C. Potassium tert-butoxide solution (2.4 equiv in THF) is added dropwise over a 10 minute period. The slurry is allowed to warm to room temperature and stirred thus for about 2.5 hours (complete by TLC at this time). The reaction is partitioned between water and EtOAc and the layers are separated. The organic phase is extracted 2 times with water and the aqueous portions are combined and washed 2–6 times with dichloromethane. The aqueous solution is made acidic by addition of 6 M HCl solution and extracted 2–6 times with dichloromethane. These last three organic extracts are combined, dried with sodium sulfate and concentrated under reduced pressure to provide the compound of structure (i-a).

In Scheme XI(a), Step B, the intermediate 6-methylidine-2-methoxycarbonyl decahydroisoquinoline-3-carboxylic acid (compound (i-a)) is esterified by reaction with a compound of formula Et-Br (where Et represents an ethyl group) to provide the 6-methylidine-decahydroisoquinoline-3-carboxylate intermediate of compound (ii-a). For example 6-methylidine-2-methoxycarbonyl-decahydroisoquinoline-3-carboxylic acid is dissolved in acetonitrile and treated with triethylamine and bromoethane. The reaction is heated at 50° C. for about 3 hours, cooled and partitioned between 50:50 ethyl acetate/heptane and 1N HCL. The organic phase is isolated and washed 3 times with water, saturated sodium bicarbonate, brine, dried over anhydrous sodium sulfate, filtered, and concentrated under vacuum to provide the compound of structure (ii-a). This crude material is dissolved in 10% ethyl acetate/heptane and applied to a plug of silica gel (10 g in 10% ethyl acetate/heptane). The plug is eluted with, 10% ethyl acetate/heptane, 15% ethyl acetate/heptane, and 25% ethyl acetate/heptane. The eluents are combined and concentrated under vacuum to provide the purified compound of structure (ii-a).

In Scheme XI(a), Step C, the 6-methylidine-decahydroisoquinoline-3-carboxylate intermediate (compound (ii-a)) is subjected to hydroboration, followed by oxidation to provide the 6-hydroxymethyl-decahydroisoquinoline-3-carboxylate intermediate of compound (A). For example, ethylmethylidine-2-methoxycarbonyl-decahydroisoquinoline-3-carboxylate is dissolved in THF and cooled to about –15° C. under an atmosphere of nitrogen with stirring. A 1M solution of $BH_3 \cdot THF$ is added dropwise over 5–7 minutes and the reaction mixture is stirred for about 2 hours at –10 to –12° C. The reaction is then slowly treated with a suitable base, such as lithium or sodium hydroxide, and then treated slowly with 30% $H_2O_2$ over 15 minutes. The reaction mixture is allowed to warm to room temperature and then partitioned between ethyl acetate and 50% saturated sodium chloride solution. The aqueous layer is extracted with ethyl acetate and the combined organics are washed with sodium bisulfite solution, brine, dried over anhydrous sodium sulfate, filtered, and concentrated under vacuum to provide the intermediate of compound (A).

Alternatively, the 6-hydroxymethyl-2-methoxycarbonyl-decahydroisoquinoline-3-carboxylate intermediate (compound (A)) may be made according to the synthetic route described in Scheme XI(b). In Scheme XI(b), Step A, 2-methoxycarbonyl-6-oxodecahydroisoquinoline-3-carboxylic acid (Pg is methoxycarbonyl) is esterified by reaction with a compound of formula Et-Br (where Et represents an ethyl group) to provide the 6-oxo-decahydroisoquinoline-3-carboxylate intermediate of compound (i-b). For example 2-methoxycarbonyl-6-oxodecahydroisoquinoline-3-carboxylic acid is dissolved in acetonitrile and treated with triethylamine and bromoethane. The reaction is heated at 50° C. for about 3 hours, cooled and partitioned between 50:50 ethyl acetate/heptane and 1N HCl. The organic phase is isolated and washed 3 times with water, saturated sodium bicarbonate, brine, dried over anhydrous sodium sulfate, filtered, and concentrated under vacuum to provide the compound of structure (i-b). This crude material is dissolved in 10% ethyl acetate/heptane and applied to a plug of silica gel (10 g in 10% ethyl acetate/heptane). The plug is eluted with 10% ethyl acetate/heptane, 15% ethyl acetate/heptane, and 25% ethyl acetate/heptane. The eluents are combined and concentrated under vacuum to provide the purified compound of structure (i-b).

In Scheme XI(b), Step B, the 6-oxodecahydroisoquinoline-3-carboxylate intermediate of compound (i-b) is treated with methyltriphenylphosphonium bromide to provide the 6-methylidine-decahydroisoquinoline-3-carboxylate of compound (ii-b). For example a slurry of 1 equivalent of ethyl-2-methoxycarbonyl-6-oxodecahydroisoquinoline-3-carboxylate (compound (i-b)) and about 1.4 equivalents of methyltriphenylphosphonium bromide in THF and DMF is stirred mechanically under an atmosphere of nitrogen and cooled to –10° C. Potassium tert-butoxide solution (2.4 equiv in THF) is added dropwise over a 10 minute period. The slurry is allowed to warm to room temperature and stirred thus for 2.5 hours (complete by TLC at this time). The reaction is partitioned between water and EtOAc and the layers are separated. The organic phase is extracted 2 times with water and the aqueous portions are combined and washed 2–6 times with dichloromethane. The aqueous solution is made acidic by addition of 6 M HCl solution and extracted 2–6 times with dichloromethane. These last three organic extracts are combined, dried with sodium sulfate and concentrated under reduced pressure to provide the compound of structure (ii-b).

In Scheme XI(b), Step C, following the procedures as described in Scheme I(a), Step C above, the 6-methylidine-decahydroisoquinoline-3-carboxylate intermediate (compound (ii-b)) is subjected to hydroboration, followed by oxidation to provide the ethyl 6-hydroxymethyl-2-methoxycarbonyl-decahydroisoquinoline-3-carboxylate intermediate of compound (A).

The following preparations and examples further illustrate the invention and represent typical synthesis of the compounds of Formula I and Formula II as described generally above. The reagents and starting materials are readily available to one of ordinary skill in the art. As used herein, the following terms have the meanings indicated: "i.v." refers to intravenously; "p.o." refers to orally; "i.p." refers to intraperitoneally; "eq" or "equiv." refers to equivalents; "g" refers to grams; "mg" refers to milligrams; "L" refers to liters; "mL" refers to milliters; "µL" refers to microliters; "mol" refers to moles; "mmol" refers to millimoles; "psi" refers to pounds per square inch; "mm Hg" refers to millimeters of mercury, "min" refers to minutes; "h" or "hr" refers to hours; "° C" refers to degrees Celsius; "ATLCL" refers to thin layer chromatography, "HPLC" refers to high performance liquid chromatography; "$R_f$" refers to retention factor, "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "IPA" refers to isopropyl alcohol; "iPrOAc" refers to isopropyl acetate; "MeOH" refers to methanol; "MTBE" refers to tert-butyl methyl ether; "$PPh_3$" refers to triphenylphosphine; "DEAD" refers to diethyl azodicarboxylate; "RT" refers to room temperature; "Pd-C" refers to palladium over carbon; $NaBH(OAc)_3$ refers to sodium triacetoxyborohydride; "Bn" refers to benzyl; "$BnNH_2$" refers to benzyl amine; $H_2$ refers to hydrogen; "$K_i$" refers to the dissociation constant of an enzyme-antagonist complex and serves as an index of ligand binding; and "$ID_{50}$" and "$ID_{100}$" refer to doses of an administered therapeutic agent which produce, respectively, a 50% and 100% reduction in a physiological response.

EXAMPLE 1

Preparation of 3S, 4aR, 6S, 8aR Ethyl 6-(((2S)-2-(Ethoxycarbonyl)-4,4-difluoropyrrolidinyl)methyl)-1,2,3,4,4a, 5,6,7,8,8a-decahydroisoquinoline-3-carboxylate

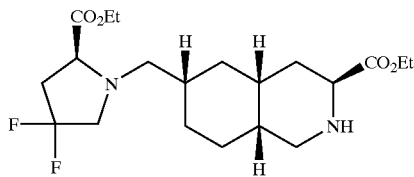

A. Preparation of 3S, 4aR, 6S, 8aR Ethyl 6-(4-Methylphenyl)sulfonyloxy)methyl)-2-methoxycarbonyl-1,2,3,4,4a, 5,6,7,8,8a-decahydroisoquinoline-3-carboxylate To a solution of 15.0 g (50.1 mmol) of 3S, 4aR, 6S, 8aR ethyl 6-hydroxymethyl-2-methoxycarbonyl-decahydroisoquinoline-3-carboxylate (prepared by one of ordinary skill in the art following the procedures as disclosed in U.S. Pat. No. 5,670,516) cooled to 0° C. in $CH_2Cl_2$ (100 mL), was added triethylamine (20.9 mL, 150.3 mmol) followed by p-toluenesulfonyl chloride (19.1 g, 100.2 mmol) dissolved in $CH_2Cl_2$ (100 mL). The reaction was warmed to room temperature and stirred 16 h, then partitioned between $CH_2Cl_2$ and 10% aqueous $NaHSO_4$. The aqueous layer was extracted with $CH_2Cl_2$ and the combined organics were dried over $MgSO_4$, filtered, and concentrated in vacuo. Column chromatography (Stepwise gradient: 10–50% EtOAc/hexane) provided 20.1 g (89%) of the desired intermediate title compound as a colorless oil:

MS(m/e): 451.5 ($M^+$)

Calculated for $C_{22}H_{31}NO_7S \cdot 0.25H_2O$: Theory: C, 57.69; H, 6.93; N, 3.06. Found. C, 57.76; H, 6.93; N. 3.35

$^{13}C$ NMR (DMSO-$d_6$): δ 171.4, 144.8, 132.4, 130.1, 127.6, 74.6, 60.4, 53.1, 52.4, 44.1, 34.6, 31.8, 31.0, 29.8, 28.8, 24.9, 23.3, 21.0, 14.0 ppm B. Preparation of 3S, 4aR, 6S, 8aR Ethyl 6-(((2S)-2-(Ethoxycarbonyl)-(4R)-4-hydroxypyrrolidinyl)methyl)-2-methoxycarbonyl-1,2,3,4,4a, 5,6,7,8,8a-decahydroisoquinoline-3-carboxylate A mixture of trans-4-hydroxy-L-proline ethyl ester hydrochloride (6.5 g, 33.1 mmol), the compound of Step A above (10.0 g, 22.0 mmol), and potassium carbonate (4.6 g, 33.1 mmol) were heated at reflux in acetonitrile (22 mL) for 60 h. The reaction mixture was cooled to room temperature, and partitioned between $CH_2Cl_2$ and $H_2O$. The aqueous layer was extracted two times with $CH_2Cl_2$ and the combined organics were dried over $MgSO_4$, filtered, and concentrated in vacuo. Column chromatography (50% EtOAc/hexane followed by 5% MeOH/$CH_2Cl_2$) gave 9.2 g (95%) of the desired intermediate title compound as a colorless oil:

MS(m/e): 441.3 ($M^+$)

Calculated for $C_{22}H_{36}N_2O_7S$: Theory: C, 59.98; H, 8.24; N, 6.36. Found: C, 60.17; H, 8.23; N, 6.42

C. Preparation of 3S, 4aR, 6S, 8aR Ethyl 6-(((2S)-2-(Ethoxycarbonyl)-4-oxopyrrolidinyl)methyl)-2-methoxycarbonyl-1,2,3,4,4a, 5,6,7,8,8a-decahydroisoquinoline-3-carboxylate To a solution of DMSO (2.3 mL, 32.5 mmol) cooled to −78° C. in $CH_2Cl_2$ (25 mL) was added, dropwise, oxalyl chloride (1.4 mL, 16.3 mmol). The reaction mixture was stirred for 5 min, then the compound of Step B above (6.0 g, 13.6 mmol) dissolved in 20 mL of $CH_2Cl_2$ was added. Upon stirring for 0.75 h at −78° C., triethylamine (9.5 mL, 32.5 mmol) was added. The reaction was warmed to room temperature over approximately 2 hours, and quenched by the addition of 10% aqueous $NaHSO_4$. The aqueous layer was extracted with $CH_2Cl_2$ and the combined organics were dried over $MgSO_4$, filtered, and concentrated in vacuo. Column chromatography (Stepwise gradient: 25–50% EtOAc/hexane) provided 4.6 g (78%) of the desired intermediate title compound as a colorless oil:

MS(m/e): 439.1 ($M^+$)

D. Preparation of 3S, 4aR, 6S, 8aR Ethyl 6(-((2S)-2-(Ethoxycarbonyl)-4,4-difluoropyrrolidinyl)methyl)-2-methoxycarbonyl-1,2,3,4,4a, 5,6,7,8,8a-decahydroisoquinoline-3-carboxylate To a mixture of the compound of Step C above (4.62 g, 10.5 mmol) cooled to −78° C. in $CH_2Cl_2$ (50 mL) was added, dropwise, diethylaminosulfur trifluoride (3.5 mL, 26.3 mmol). The reaction was allowed to warm to room temperature, stirred an additional 48 h, then quenched by the addition of MeOH. After concentrating in vacuo, the residue was partitioned between $CH_2Cl_2$ and saturated aqueous $NaHCO_3$. The aqueous layer was extracted with $CH_2Cl_2$ and the combined organics were dried over $MgSO_4$, filtered, and concentrated in vacuo. Column chromatography (Stepwise gradient: 25–50% BtOAc/hexane) provided 3.3 g (68%) of the desired intermediate title compound as a colorless oil:

MS(m/e): 461.2 ($M^+$)

Calculated for $C_{22}H_{34}F_2N_2O_6$: Theory: C, 57.38; H. 7.44; N, 6.08. Found: C, 57.28; H, 7.52; N, 6.13

E. Preparation of 3S, 4aR, 6S, 8aR Ethyl 6-(((2S)-2-(Ethoxycarbonyl)-4,4-difluoropyrrolidinyl)methyl)-1,2,3,4,4a, 5,6,7,8,8a-decahydroisoquinoline-3-carboxylate A solution of the compound of Step D above (3.3 g, 7.10 mmol) dissolved in $CH_2Cl_2$ (40 mL) was cooled to 0° C. and charged with iodotrimethylsilane (3.0 mL, 21.3 mmol). The reaction was allowed to warm to room temperature, stirred an additional 4 h, then quenched by the addition of saturated aqueous $NaHCO_3$ (50 mL). The aqueous layer was extracted with $CH_2Cl_2$ and the combined organics washed with 1 N $NaS_2O_3$, dried over $MgSO_4$, filtered, and concentrated in vacuo. The material was chromatographed (2% MeOH/$CH_2Cl_2$), dissolved in 20 mL of $Et_2O$, and to it was added 50 mL of 2 M HCl/$Et_2O$. The solvent was removed in vacuo, providing 2.6 g (76%) of the final title compound as a white solid:

MS(m/e): 403.4 ($M^+$)

Calculated for $C_{20}H_{32} \cdot Cl_2F_2N_2O_4$: Theory: C, 50.53; H, 7.21; N, 5.89.

Found: C, 50.90; H. 7.41; N, 5.84

$^{13}C$ NMR ($D_2O$): δ 170.3, 167.7, 125.1 (t, $J_{C-F}$=249.1 Hz), 65.9, 65.0, 64.1, 63.4, 60.1 (t, $J_{C-F}$=33.9 Hz), 57.6, 52.8, 42.9, 37.2 (t, $J_{C-F}$=26.4 Hz), 34.5, 31.7, 31.3, 30.5, 28.4, 26.9, 24.3, 13.6 ppm

EXAMPLE 2

Preparation of 3S, 4aR, 6S, 8aR 6-(((2S)-2-(Carboxylic acid)-4,4-difluoropyrrolidinyl)methyl)-1,2,3,4,4a, 5,6,7,8,8a-decahydroisoquinoline-3-carboxylic Acid

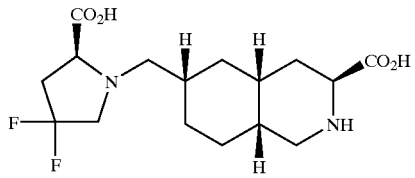

A solution of 3S, 4aR, 6S, 8aR ethyl 6-(((2S)-2-(ethoxycarbonyl)-4,4-difluoropyrrolidinyl)methyl)-2-methoxycarbonyl-1,2,3,4,4a, 5,6,7,8,8a-decahydroisoquinoline-3-carboxylate (3.3 g, 7.10 mmol), the compound from Step D of Example 1 above, dissolved in 5 N aqueous HCl (15 mL), was heated at 90° C. for 18 h. The reaction mixture was cooled to room temperature and concentrated in vacuo. The resulting crude foam was dissolved in $H_2O$ (75 mL) and stirred in the presence of Dowex 50×8 (100–200) ion-exchange resin (10 g) for 2 h. The resin was filtered, washed sequentially with 1:1 THF/$H_2O$ and $H_2O$, then stirred in the presence of 10% pyridine/$H_2O$ for 2 h. After filtration, the resin was washed with $H_2O$, and the filtrate was concentrated in vacuo to provide the title compound (0.6 g, 97%) as a white foam:

MS(m/e): 347.2 ($M^+$)

Calculated for $C_{16}H_{24}F_2N_2O_4 \cdot 0.1H_2O$: Theory. C, 55.19; H 7.01; N, 8.05. Found: C, 54.81; H,6.82; N, 8.13

$^{13}C$ NMR ($D_2O$): δ 175.1, 171.1, 125.6 (t, $J_{C-F}$=249.4 Hz), 67.9, 63.0, 59.3 (t, $J_{C-F}$=34.0 Hz), 54.5, 42.5, 37.5 (t, $J_{C-F}$=24.9 Hz), 34.3, 32.7, 32.4, 30.6, 28.2, 27.0, 24.3 ppm

EXAMPLE 3

Preparation of 3S, 4aR, 6S, 8aR 6{(((2S)$_2$-(Carboxylic acid)-(4R)-4-fluoropyrrolidinyl)methyl)-1,2,3,4,4a,5,6,7,8,8a-decahydroisoquinoline-3-carboxylic Acid

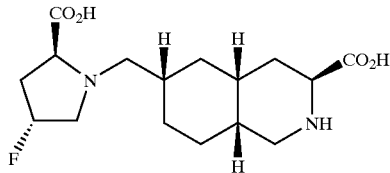

A. Preparation of 3S, 4aR, 6S, 8aR Ethyl 6-(((2S)-2-(Ethoxycarbonyl)(4R)-4-fluoropyrrolidinyl)methyl)-2-methoxycarbonyl-1,2,3,4,4a, 5,6,7,8,8a-decahydroisoquinoline-3-carboxylate To a solution of 1.0 g (2.76 mmol) of 3S, 4aR, 6S, 8aR ethyl 6-bromomethyl-2-methoxycarbonyl-decahydroisoquinoline-3-carboxylate (prepared by one of ordinary skill in the art following the procedures as disclosed in U.S. Pat. No. 5,670,516) dissolved in $CH_3CN$ (2.5 mL) was added $K_2CO_3$ (0.57 g, 4.14 mmol), followed by trans-4-fluoro-L-proline ethyl ester (0.67 g, 4.14 mmol) (Demange, L.; Ménez, A.; Dugave, C. *Tetrahedron Lett.* 1998, 39, 1169–1172.). The reaction mixture was heated at 80° C. for 72 h, then cooled to room temperature and loaded onto a 10 g SCX Mega Bond Elut SPE cartridge (Varian Sample Preparation Products). The resin was washed sequentially with $CH_2Cl_2$ (50 mL) followed by MeOH (50 mL), then 2 M $NH_3$/MeOH (50 mL). Following concentration in vacuo, the resulting residue was chromatographed (50% EtOAc/hexane) to provide 0.64 g (52%) of the desired intermediate title compound:

MS(m/e): 443.2 ($M^+$)

Calculated for $C_{22}H_{35}FN_2O_6$: Theory: C, 59.71; H, 7.97; N, 6.33. Found: C, 59.79; H, 7.71; N, 6.37

B. Preparation of 3S, 4aR, 6S, 8aR 6-(((2S)-2-(Carboxylic acid)-(4R)-4-fluoropyrrolidinyl)methyl)-1,2,3,4,4a, 5,6,7,8,8a-decahydroisoquinoline-3-carboxylic Acid A solution of 3S, 4aR, 6S, 8aR ethyl 6-(((2S)-2-(ethoxycarbonyl)-(4R)-4-fluoropyrrolidinyl)methyl)-1,2,3,4,4a, 5,6,7,8,8a-decahydroisoquinoline-3-carboxylate (0.40 g, 0.90 mmol), the compound of Step A above, dissolved in 5 N aqueous HCl (15 mL), was heated at 90° C. for 18 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 THF/$H_2O$ and $H_2O$, then stirred in the presence of 10% pyridine/$H_2O$ for 2 h. After filtration, the resin was washed with $H_2O$, and the filtrate was concentrated in vacuo to provide the title compound (0.25 g, 84%) as a white foam:

MS(m/e): 329.2 ($M^+$)

Calculated for $C_{16}H_{24}F_2N_2O_4 \cdot 0.7H_2O$: Theory: C, 56.36; H, 7.80; N, 8.22. Found: C, 56.38; H. 7.99; N, 8.00

$^{13}C$ NMR ($D_2O$): δ 175.6, 173.0, 94.7 (d, $J_{C-F}$=175.5 Hz), 70.0, 64.5, 61.6 (d, $J_{C-F}$=24.3 Hz), 54.9, 42.9, 37.5 (d, $J_{C-F}$=21.2 Hz), 35.0, 32.9, 32.7, 31.1, 28.7, 27.5, 24.7 ppm

EXAMPLE 4

Preparation of 3S, 4aR, 6S, 8aR 6-(((2S)-2-(Carboxylic acid)-(4R)-4-chloropyrrolidinyl)methyl)-1,2,3,4,4a, 5,6,7,8,8a-decahydroisoquinoline-3-carboxylic Acid

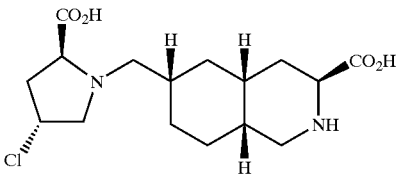

A. Preparation of 3S, 4aR, 6S, 8aR Ethyl 6-(((2S)-2-(Ethoxycarbonyl)-(4S)4 -hydroxypyrrolidiyl)methyl)-2-methoxbonyl-1,2,3,4,4a, 5,6,7,8,8a-decahydroisoquinoline-3-carboxylate A solution of cis-4-hydroxy-L-proline (2.0 g, 15.3 mmol) cooled to 0° C. in 20 mL of EtOH was saturated with gaseous HCl. The reaction was warmed to room temperature and stirred 12 h, then concentrated in vacuo. An excess solution of 2 M $NH_3$/MeOH was added, the solution was stirred for 0.25 h, then allowed to stand for an additional 0.25 h. The residual salt was removed via vacuum filtration, and the filtrate was concentrated in vacuo to provide 2.3 g (98%) of cis-hydroxy-L-pyroline ethyl ester, which was used without further purification.

To a solution of 3.6 g (10.0 mmol) of 3S, 4aR, 6S, 8aR ethyl 6-bromomethyl-2-methoxycarbonyl-decahydroisoquinoline-3-carboxylate (prepared by one of ordinary skill in the art following the procedures as disclosed in U.S. Pat. No. 5,670,516) dissolved in $CH_3CN$ (10 mL) was added $K_2CO_3$ (2.1 g, 15.0 mmol), followed by cis-hydroxy-L-proline ethyl ester (2.3 g, 15.0 mmol). The reaction mixture was heated at 80° C. for 48 h, then cooled to room temperature and partitioned between CH$_2$Cl$_2$ and H$_2$O. The aqueous layer was extracted with CH$_2$Cl$_2$, and the combined organics were dried (MgSO$_4$) and concentrated in vacuo. The resulting residue was chromatographed (50% EtOAc/hexane followed by 10% MeOH/CH$_2$Cl$_2$) to provide 3.83 g (87%) of the desired intermediate title compound.

B. Preparation of 3S, 4aR, 6S, 8aR Ethyl 6-(((2S)-2-(Ethoxycarbonyl)(4R)-4 -chloropyrrolidinyl)methyl)-2-methoxycarbonyl-1,2,3,4,4a, 5,6,7,8,8a-decahydroisoquinoline-3-carboxylate A mixture of triphenylphosphine (3.6 g, 13.6 mmol) and CCl$_4$ (1.3 mL, 13.6 mmol) dissolved in CH$_2$Cl$_2$ (5 mL) was stirred at room temperature for 0.25 h. A solution of 3S, 4aR, 6S, 8aR ethyl 6-(((2S)-2-(ethoxycarbonyl)-(4S)-4-hydroxypyrrolidinyl)methyl)-2-methoxycarbonyl-1,2,3,4, 4a, 5,6,7,8,8a-decahydroisoquinoline-3-carboxylate, the compound of Step A above, dissolved in CH$_2$Cl$_2$ (10 mL) was added, and the reaction was stirred at room temperature for 20 h. The reaction was partitioned between CH$_2$Cl$_2$ and 10% aqueous NaHSO$_4$, the aqueous layer was extracted with CH$_2$Cl$_2$, and the combined organics were dried (MgSO$_4$) and concentrated in vacuo. The resulting residue was chromatographed (50% EtOAc/hexane) to provide 0.63 g (30%) of the desired intermediate title compound:

MS(m/e): 459.5 (M$^+$)

Calculated for C$_{22}$H$_{35}$ClN$_2$O$_6$: Theory: C, 57.57; H, 7.69; N, 6.10.

Found: C, 57.47; H, 7.64; N, 6.02

C. Preparation of 3S, 4aR, 6S, 8aR 6-(((2S)-2-(Carboxylic acid)-(4R)-4-chloropyrrolidinyl)methyl)-1,2,3,4,4a, 5,6,7,8, 8a-decahydroisoquinoline-3-carboxylic Acid.

A solution of 3S, 4aR, 6S, 8aR ethyl 6-(((2S)-2-(ethoxycarbonyl)-(4R)-4-chloropyrrolidinyl)methyl)-2-methoxycarbonyl-1,2,3,4,4a, 5,6,7,8,8a-decahydroisoquinoline-3-carboxylate (0.63 g, 1.37 mmol), the compound of Step B above, cooled to 0° C. in 5 mL of CH$_2$Cl$_2$, was charged with iodotrimethylsilane (0.59 mL, 4.12 mmol). The reaction was warmed to room temperature, stirred for 3 h, and quenched by the addition of saturated aqueous NaHCO$_3$ (50 mL). The aqueous layer was extracted (CH$_2$Cl$_2$), and the combined organic layers were washed sequentially with saturated aqueous NaHCO$_3$, 1N aqueous Na$_2$S$_2$O$_3$, then dried (MgSO$_4$) and concentrated in vacuo. The resulting residue was chromatographed (50% MeOH/CH$_2$Cl$_2$) to provide 0.54 g (98%) of the amine intermediate, which was dissolved in 5 N aqueous HCl (15 mL) and heated at 50–70° C. for a total of 30 h. The reaction mixture was cooled to room temperature and concentrated in vacuo. The resulting crude foam was dissolved in H$_2$O (50 mL) and stirred in the presence of Dowex 50×8 (100–200) ion-exchange resin (3 g) for 2 h. The resin was filtered, washed sequentially with 1:1 TBF/H$_2$O and H$_2$O, then stirred in the presence of 10% pyridine/H$_2$O for 2 h. After filtration, the resin was washed with H$_2$O, and the filtrate was concentrated in vacuo to provide the title compound (0.35 g, 75%) as a white foam:

MS(m/e): 345.1 (M$^+$)

Calculated for C$_{16}$H$_{25}$ClN$_2$O$_4$: Theory: C, 55.73; H, 7.31; N, 8.12.

Found: C, 55.38; H, 7.64; N, 8.06

$^{13}$C NMR (D$_2$O): δ 175.6, 173.0, 70.1, 65.1, 63.7, 56.3, 55.0, 43.0, 40.3, 35.1, 33.1, 32.7, 31.1, 28.7, 27.5, 24.8 ppm

EXAMPLE 5

Preparation of 3S, 4aR, 6S, 8aR 6-(((2S)-2-(Carboxylic acid)-(4S)-4-fluoropyrrolidinyl)methyl)1,2,3,4,4a,5,6,7,8, 8a-decahydroisoquinoline-3-carboxylic Acid

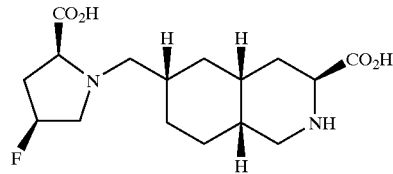

A. Preparation of 3S, 4aR, 6S, 8aR Ethyl 6-(((2S)-2-(Ethoxycarbonyl)-(4S)-4 fluoropyrrolidinyl)methyl)-2-methoxycarbonyl-1,2,3,4,4a, 5,6,7,8,8a-decahydroisoquinoline-3-carboxylate To a solution of 1.0 g (2.76 mmol) of 3S, 4aR, 6S, 8aR ethyl 6-bromomethyl-2-methoxycarbonyl-decahydroisoquinoline-3-carboxylate (prepared by one of ordinary skill in the art following the procedures as disclosed in U.S. Pat. No. 5,670,516) dissolved in CH$_3$CN (2.8 mL) was added K$_2$CO$_3$ (0.57 g, 4.14 mmol), followed by cis-4-fluoro-L-proline ethyl ester (0.57 g, 4.14 mmol) (prepared by one of ordinary skill in the art following the procedures disclosed in Tetrahedron Lett., 39, 1169–1172 (1998)). The reaction mixture was heated at 80° C. for 120 h, cooled to room temperature, then partitioned between CH$_2$Cl$_2$ and H$_2$O. The aqueous layer was extracted with CH$_2$Cl$_2$, and the combined organics were dried (MgSO$_4$), and concentrated. The residue was loaded onto a 10 g SCX cartridge (Varian). The resin was washed sequentially with CH$_2$Cl$_2$ (50 mL) followed by MeOH (50 mL), then 2 M NH$_3$/MeOH (50 mL). Following concentration in vacuo, the resulting residue was chromatographed (50% EtOAc/hexane) to provide 0.75 g (61%) of the desired intermediate title compound:

MS(m/e): 443.2(M$^+$)

Calculated for C$_{22}$H$_{35}$FN$_2$O$_6$: Theory: C, 59.71; H, 7.97; N, 6.33. Found: C, 59.65; H. 8.06; N, 6.43

B. Preparation of 3S, 4aR, 6S, 8aR 6-(((2S)-2-(Carboxylic acid)-(4S)-4-fluoropyrrolidinyl)methyl)-1,2,3,4,4a,5,6,7,8, 8a-decadhydroisoquinoline-3-carboxylic Acid.

A solution of 3S, 4aR, 6S, 8aR ethyl 6-(((2S)-2-(ethoxycarbonyl)-(4S)-4-fluoropyrrolidinyl)methyl)-2-methoxycarbonyl-1,2,3,4,4a, 5,6,7,8,8a-decahydroisoquinoline-3-carboxylate (0.30 g, 0.68 mmol), the compound of Step A above, dissolved in 5 N aqueous HCl (10 mL), was heated at 90° C. for 60 h. The reaction mixture was cooled to room temperature and concentrated in vacuo. The resulting crude foam was dissolved in H$_2$O (50 mL) and stirred in the presence of Dowex 50×8 (100–200) ion-exchange resin (3 g) for 2 h. The resin was filtered, washed sequentially with 1:1 THF/H$_2$O and H$_2$O, then stirred in the presence of 10% pyridine/H$_2$O (75 mL) for 2 h. After filtration, the resin was washed with H$_2$O, and the filtrate was concentrated in vacuo to provide the title compound (0.21 g, 94%) as a white foam:

MS(m/e): 329.2(M$^+$)

Calculated for C$_{16}$H$_{24}$F$_2$N$_2$O$_4$·1.0H$_2$O: Theory: C, 55.48; H, 7.86; N, 8.09. Found: C, 55.32; H, 7.68; N, 7.88

$^{13}$C NMR (D$_2$O): δ 175.6, 174.0, 92.6 (d, J$_{C-F}$=175.1 Hz), 68.7, 62.1, 61.9 (d, J$_{C-F}$=34.3 Hz), 55.0, 43.0, 36.6 (d, J$_C$-F=21.4 Hz), 35.1, 32.9, 32.7, 31.1, 28.9, 27.5, 24.9 ppm

EXAMPLE 6

Preparation of 3S, 4aR, 6S, 8aR 6-(((2S)-2-(Carboxylic acid)-(4R)-4-bromopyrrolidinyl)methyl)-1,2,3,4,4a,5,6,7,8,8a-decahydroisoquinoline-3-carboxylic Acid

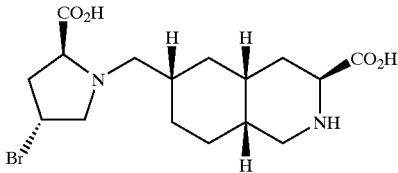

A. Preparation of 3S, 4aR 6S, 8aR Ethyl 6-(((2S)-2-(Methoxycarbonyl)-(4S)-4-hydroxypyrrolidinyl)methyl)-2-methoxycarbonyl-1,2,3,4,4a, 5,6,7,8,8a-decahydroisoquinoline-3-carboxylate To a mixture of acetyl chloride (2.3 mL, 32.0 mmol) cooled to 0° C. in 40 mL of MeOH was added cis-4-hydroxy-L-proline (3.0 g, 22.9 mmol). The reaction was heated at 50° C., stirred for 5 h, then cooled and diluted with $Et_2O$. The solid was collected by vacuum filtration and dried to provide 3.4 g (81%) of cis-hydroxy-L-proline methyl ester hydrochloride salt, 3.0 g (16.6 mmol) of which was suspended in $CH_3CN$ (15 mL), and treated with triethyl amine (2.3 mL 16.6 mmol). After 10 min at room temperature, 3.6 g (10.0 mmol) of 3S, 4aR, 6S, 8aR ethyl 6-bromomethyl-2-methoxycarbonyl-decahydroisoquinoline-3-carboxylate (prepared by one of ordinary skill in the art following the procedures as disclosed in U.S. Pat. No. 5,670,516) dissolved in $CH_3CN$ (30 mL) followed by $K_2CO_3$ (2.1 g, 15.0 mmol), was added. The reaction mixture was heated at 80° C. for 96 h, then the reaction was charged with an additional portion of cis-hydroxy-L-proline methyl ester hydrochloride salt (0.35 g) and triethylamine (0.27 mL). After stirring at 80° C. for an additional 24, the reaction was cooled to room temperature and partitioned between $CH_2Cl_2$ and $H_2O$. The aqueous layer was extracted with $CH_2Cl_2$, and the combined organics were dried ($MgSO_4$) and concentrated in vacuo. The resulting residue was chromatographed (50% EtOAc/hexane followed by 10% MeOH/$CH_2Cl_2$) to provide 1.77 g (50%) of the desired intermediate title compound.

MS(m/e): 427.8 (M+)

Calculated for $C_{21}H_{34}N_2O_7$: Theory: C, 59.14; H, 8.04; N, 6.57. Found: C, 58.84; H, 7.85; N, 6.62

B. Preparation of 3S, 4aR, 6S, 8aR Ethyl 6-(((2S)-2-Methoxycarbonyl)-(4R)-4-bromopyrrolidinyl)methyl)-2-methoxycarbonyl-1,2,3,4,4a, 5,6,7,8,8a-decahydroisoquinoline-3-carboxylate A mixture of triphenylphosphine (0.69 g, 2.64 mmol) and $Br_2$ (0.14 mL, 2.64 mmol) dissolved in $CH_2Cl_2$ (5 mL) was stirred at room temperature for 0.25 h. A solution of 3S, 4aR, 6S, 8aR ethyl 6-(((2S)-2-(methoxycarbonyl)-(4S)-4hydroxypyrrolidinyl)methyl)-2-methoxycarbonyl-1,2,3,4,4a, 5,6,7,8,8a-decahydroisoquinoline-3-carboxylate (0.75 g, 1.76 mmol), the compound of Step A above, and pyridine (0.29 mL, 3.52 mmol) dissolved in $CH_2Cl_2$ (10 mL), was added, and the reaction was stirred at room temperature for 21 h. The reaction was partitioned between $CH_2Cl_2$ and 10% aqueous $NaHSO_4$, the aqueous layer was extracted with $CH_2Cl_2$, and the combined organics were dried ($MgSO_4$) and concentrated in vacuo. Diethyl ether was added, and residual triphenylphosphine oxide was removed by vacuum filtration. After rotary evaporation, the resulting residue was chromatographed (50% EtOAc/hexane then 5% MeOH/$CH_2Cl_2$) to provide 0.43 g (50%) of the desired intermediate title compound:

MS(m/e): 489.3 (M+)

Calculated for $C_{21}H_{35}BrN_2O_6 \cdot 0.5H_2O$: Theory: C, 50.61; H, 6.88; N, 5.62. Found: C, 50.89; H. 6.65; N, 5.62

C. Preparation of 3S, 4aR, 6S, 8aR 6-(((2S)-2-(Carboxylic acid)-(4R)-4-bromopyrrolidinyl)methyl)-1,2,3,4,4a,5,6,7,8,8a-decahydroisoquinoline-3-carboxylic Acid.

A solution of 3S, 4aR, 6S, 8aR ethyl 6-(((2S)-2-methoxycarbonyl)-(4R)-4-bromopyrrolidinyl)methyl)-2-methoxycarbonyl-1,2,3,4,4a, 5,6,7,8,8a-decahydroisoquinoline-3-carboxylate (0.43 g, 0.88 mmol), the compound of Step B above, dissolved in 5 N aqueous HCl (10 mL) was heated at 70° C. for 48 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 THF/$H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.20 g, 58%) as a white foam:

MS(m/e): 389.1 (M+)

Calculated for $C_{16}H_{25}BrN_2O_4$: Theory: C, 49.37; H, 6.47; N, 7.20.

Found: C, 49.78; H, 6.48; N, 6.77

$^{13}C$ NMR ($D_2O$): δ 175.6, 173.0, 70.1, 65.1, 63.7, 56.3, 55.0, 43.0, 40.3, 35.1, 33.1, 32.7, 31.1, 28.7, 27.5, 24.8 ppm

EXAMPLE 7

Preparation of 3S, 4aR, 6S, 8aR 6-(((2S)-2-(Carboxylic acid)(4S)-4-iodopyrrolidinyl)methyl)-1,2,3,4,4a,5,6,7,8,8a-decahydroisoquinoline-3-carboxylic Acid

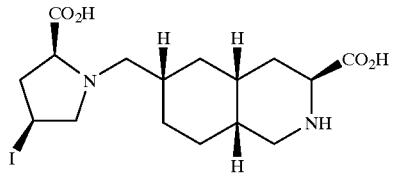

A. Preparation of 3S, 4aR, 6S, 8aR Ethyl 6-(((2S)-2-(Ethoxycarbonyl)-(4S)-4 -iodopyrrolidinyl)methyl)-2-methoxycarbonyl-1,2,3,4,4a,5,6,7,8,8a-decahydroisoquinoline-3-carboxylate A mixture of triphenylphosphine (0.61 g, 2.3 mmol), $I_2$ (0.59 mL, 2.3 mmol), and imidazole (0.16 g, 2.3 mmol), dissolved in $CH_2Cl_2$ (20 mL) was stirred at room temperature for 0.25 h. A solution of 3S, 4aR, 6S, 8aR ethyl 6-(((2S)-2-(ethoxycarbonyl)-(4R)-4-hydroxypyrrolidinyl) methyl)-2-methoxycarbonyl-1,2,3,4,4a,5,6,7,8,8a-decahydroisoquinoline-3-carboxylate, the compound of Step B described in the preparation of Example 1 above (0.68 g, 1.5 mmol), dissolved in $CH_2Cl_2$ (10 mL), was added, and the reaction was stirred at room temperature for 18 h. The reaction was partitioned between $CH_2Cl_2$ and 10% aqueous $NaHSO_4$, the aqueous layer was extracted with $CH_2Cl_2$, and the combined organics were dried ($MgSO_4$) and concentrated in vacuo. The resulting residue was chromatographed (50% EtOAc/hexane) to provide 0.52 g (61%) of the desired intermediate title compound:

MS(m/e): 551.3 (M+)

Calculated for $C_{22}H_{35}IN_2O_6$: Theory: C, 48.01; H, 6.41; N, 5.09. Found: C, 48.02; H, 6.27; N, 4.81

B. Preparation of 3S, 4aR, 6S, 8aR 6-(((2S)-2-(Carboxylic acid)-(4S)-4-iodopyrrolidinyl)methyl)-1,2,3,4,4a,5,6,7,8,8a-decahydroisoquinoline-3-carboxylic Acid.

A solution of 3S, 4aR, 6S, 8aR ethyl 6-(((2S)-2-(ethoxycarbonyl)(4S)-4 iodopyrrolidinyl)methyl)-2-methoxycarbonyl-1,2,3,4,4a,5,6,7,8,8a-decahydroisoquinoline-3carboxylate (0.51 g, 0.93 mmol), the compound of Step A above, dissolved in 5 N aqueous HCl (20 mL) was heated at 100° C. for 12 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 THF/$H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.37 g, 91%) as a white foam:

MS(m/e): 437.2 (M+)

Calculated for $C_{16}H_{25}IN_2O_4$: Theory: C, 44.05; H, 5.78; N, 6.42. Found: C, 44.31; H, 5.80; N, 6.38

EXAMPLE 8

Preparation of 3S, 4aR, 6S, 8aR 6-(((2S)-2-(Carboxylic acid)-(4S)-4-chloropyrrolidinyl)methyl)-1,2,3,4,4a,5,6,7,8,8a-decahydroisoquinoline-3-carboxylic Acid

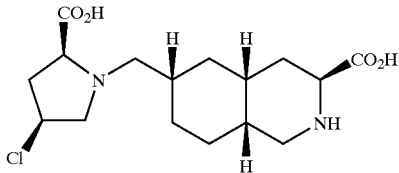

A. Preparation of 3S, 4aR, 6S, 8aR Ethyl 6-(((2S)-2-(Ethoxycarbonyl)(4S)4-chloropyrrolidinyl)methyl)-2-methoxycarbonyl-1,2,3,4,4a,5,6,7,8,8a-decahydroisoquinoline-3-carboxylate A mixture of triphenylphosphine (0.67 g, 2.55 mmol) and $CCl_4$ (0.25 mL, 2.55 mmol) dissolved in $CH_2Cl_2$ (10 mL) was stirred at room temperature for 0.25 h. A solution of 3S, 4aR, 6S, 8aR ethyl 6-(((2S)-2-(ethoxycarbonyl)-(4R)-4-hydroxypyrrolidinyl)methyl)-2-methoxycarbonyl-1,2,3,4,4a,5,6,7,8,8a-decahydroisoquinoline-3-carboxylate, the compound of Step B described in the preparation of Example 1 above (0.75 g, 1.70 mmol), dissolved in $CH_2Cl_2$ (10 mL) was added, and the reaction was stirred at room temperature for 18 h. Additional triphenylphosphine (0.77 mmol) and $CCl_4$ (0.77 mmol) were added, and the reaction was heated at 40° C. for 5 h. The reaction was partitioned between $CH_2Cl_2$ and 10% aqueous $NaHSO_4$, the aqueous layer was extracted with $CH_2Cl_2$, and the combined organics were dried ($MgSO_4$) and concentrated in vacuo. The resulting residue was chromatographed (50% EtOAc/hexane) to provide 0.59 g (76%) of the desired intermediate title compound:

MS(m/e): 459.5 (M+)

Calculated for $C_{22}H_{35}ClN_2O_6$: Theory: C, 57.57; H, 7.69; N, 6.10.

Found. C, 57.64; H, 7.58; N, 5.88

B. Preparation of 3S, 4aR, 6S, 8aR 6(((2S)-2-(Carboxylic acid)(4S)-4-chloropyrrolidinyl)methyl)-1,2,3,4,4a,5,6,7,8,8a-decahydroisoquinoline-3-carboxylic Acid A solution of 3S, 4aR, 6S, 8aR ethyl 6-(((2S)-2-ethoxycarbonyl)(4S)$_4$ chloropyrrolidinyl)methyl),-1,2,3,4,4a,5,6,7,8,8a-decahydroisoquinoline-3-carboxylate (0.58 g, 1.26 mmol), the compound of Step A above, dissolved in 5 N aqueous HCl (20 mL) was heated at 100° C. for 12 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 THF/$H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.38 g, 87%) as a white foam:

MS(m/e): 345.1 (M$^{30}$)

Calculated for $C_{16}H_{25}ClN_2O_4 \cdot 0.25H_2O$: Theory: C, 55.01; 17.36; N, 8.02. Found: C, 54.71; H, 7.26; N, 7.76

$^{13}C$ NMR ($D_2O$): δ 183.1, 181.3, 70.4, 63.5, 62.8, 56.3, 44.3, 41.5, 37.5, 36.8, 34.9, 34.7, 31.2, 29.4, 27.2 ppm

EXAMPLE 9

Preparation of 3S, 4aR, 6S, 8aR 6(((2S)-2-(Carboxylic acid)-(4S)-4-bromopyrrolidinyl)methyl)-1,2,3,4,4a,5,6,7,8,8a-decahydroisoquinoline-3-carboxylic Acid

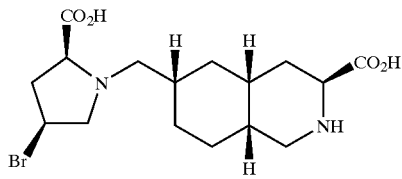

A. Preparation of 3S, 4aR, 6S, 8aR Ethyl 6-(((2S)-2-(Ethoxycarbonyl)-(4R)-4-hydroxypyrrolidinyl)methyl)-1,2,3,4,4a,5,6,7,8,8a-decahydroisoquinoline-3-carboxylate To a solution of 3S, 4aR, 6S, 8aR ethyl 6-(((2S)-2-(ethoxycarbonyl)-(4R)-4-hydroxypyrrolidinyl)methyl)-2-methoxycarbonyl-1,2,3,4,4a,5,6,7,8,8a-decahydroisoquinoline-3-carboxylate, the compound of Step B described in the preparation of Example 1 above (1.5 g, 3.4 mmol), cooled to 0° C. in $CH_2Cl_2$ (10 mL) was added iodotrimethylsilane (1.45 mL, 10.2 mmol). The reaction was warmed to room temperature, stirred for 3 h, and then quenched by the addition of saturated aqueous $NaHCO_3$. The reaction was partitioned between $CH_2Cl_2$ and 10% aqueous $NaHSO_4$, the aqueous layer was extracted with $CH_2Cl_2$, and the combined organics were dried ($MgSO_4$) and concentrated in vacuo to provide 1.22 g (94%) of the desired intermediate title compound.

B. Preparation of 3S, 4aR, 6S, 8aR Ethyl 6-(((2S)-2-(Ethoxycarbonyl)(4R)-4-hydroxypyrrolidinyl)methyl)-2-tert-butoxycarbonyl)-1,2,3,4,4a,5,6,7,8,8a-decahydroisoquinoline-3-carboxylate To a solution of 3S, 4aR, 6S, 8aR ethyl 6-(((2S)-2-(ethoxycarbonyl)-(4R) hydroxypyrrolidinyl)methyl)-1,2,3,4,4a,5,6,7,8,8a-decahydroisoquinoline-3-carboxylate, the compound of Step A described in the preparation above (1.22 g, 3.19 mmol), dissolved in THF (10 mL) was added a solution of 1N aqueous sodium hydroxide (10 mL) followed by di-tert-butyl dicarbonate (1.04 g, 4.78 mmol). The reaction was stirred for 1.5 h, then partitioned between $CH_2Cl_2$ and $H_2O$. The aqueous layer was extracted with $CH_2Cl_2$, and the combined organics were dried ($MgSO_4$) and concentrated in vacuo. Column chromatography (EtOAc, then 5% MeOH/CH$_2$Cl$_2$) provided 1.04 g (68%) of the desired intermediate title compound.

C. Preparation of 3S, 4aR, 6S, 8aR Ethyl 6-(((2S)-2-(Ethoxycarbonyl)-(4S)-4-bromopyrrolidinyl)methyl)-2-(tert-butoxycarbonyl)-1, 2, 3, 4, 4, 5, 6, 7, 8, 8a-decahydroisoquinoline-3-carboxylate A mixture of triphenylphosphine (0.85 g, 3.23 mmol) and Br$_2$ (0.17 mL, 3.23 mmol) dissolved in CH$_2$Cl$_2$ (5 mL) was stirred at room temperature for 0.25 h. A solution of 3S, 4aR, 6S, 8aR ethyl 6-(((2S)$_2$-(ethoxycarbonyl)-(4R)-4-hydroxypyrrolidinyl)methyl)-2-(tert-butoxycarbonyl)-1,2,3,4,4a,5,6,7,8,8a-decahydroisoquinoline-3-carboxylate (1.04 g, 2.15 mmol), the compound of Step B above, and pyridine (0.35 mL, 4.30 mmol) dissolved in CH$_2$Cl$_2$ (15 mL) was added, and the reaction was stirred at room temperature for 20 h. The reaction was partitioned between CH$_2$Cl$_2$ and 10% aqueous NaHSO$_4$, the aqueous layer was extracted with CH$_2$Cl$_2$, and the combined organics were dried (MgSO$_4$) and concentrated in vacuo. Ether was added, and residual triphenylphosphine oxide was removed by vacuum filtration. After rotary evaporation, the resulting residue was chromatographed (25% EtOAc/hexane) to provide 0.62 g (53%) of the desired intermediate title compound:

MS(m/e): 545.5(M$^+$)

D. Preparation of 3S, 4aR, 6S, 8aR Ethyl 6-(((2S)-2-(Ethoxycarbonyl)-(4S)$_4$ bromopyrrolidinyl)methyl)-1,2,3,4,4a,5,6,7,8,8a-decahydroisoquinoline-3-carboxylate A solution of 3S, 4aR, 6S, 8aR ethyl 6-(((2S2-(ethoxycarbonyl)-(4S)-4bromopyrrolidinyl)methyl)-2-(tert-butoxycarbonyl)-1,2,3,4,4a,5,6,7,8,8a-decahydroisoquinoline-3-carboxylate (0.62 g, 1.14 mmol), the compound of Step C above, was dissolved in 1 N HCl/EtOAc, and stirred at room temperature for 20 h. The reaction was concentrated in vacuo, then acetone was added and subsequently removed in vacuo (two times). The residual solid was suspended in diethyl ether, then collected by vacuum filtration to provide 0.55 g (100%) of the desired intermediate title compound:

MS(m/e): 445.2 (M$^+$)

Calculated for C$_{20}$H$_{33}$BrCl$_2$N$_2$O$_4$.2.0H$_2$O: Theory: C, 43.49; H, 6.75; N, 5.07. Found: C, 43.76; H, 6.52; N, 4.96

E. Preparation of 3S, 4aR, 6S, 8aR 6-(((2S)-2-(Carboxylic acid)-(4S)-4-bromopyrrolidinyl)methyl)-1,2, 3, 4, 4a, 5, 6, 7, 8, 8a-decahydroisoquinoline-3-carboxylic Acid A solution of 3S, 4aR, 6S, 8aR ethyl 6((2S)-2-(ethoxycarbonyl)(4S)-4-bromopyrrolidinyl)methyl)-1,2,3,4,4a,5,6,7,8,8a-decahydroisoquinoline-3-carboxylate (0.35 g, 0.68 mmol), the compound of Step D above, dissolved in 5 N aqueous HCl (15 mL) was heated at 70° C. for 12 h. The reaction mixture was cooled to room temperature and concentrated in vacuo. The resulting crude foam was dissolved in H$_2$O (50 mL) and stirred in the presence of Dowex 50×8 (100–200) ion-exchange resin (3 g) for 2 h. The resin was filtered, washed sequentially with 1:1 THF/H$_2$O and H$_2$O, then stirred in the presence of 10% pyridine/H$_2$O (75 mL) for 2 h. After filtration, the resin was washed with H$_2$O, and the filtrate was concentrated in vacuo to provide the title compound (0.20 g, 76%) as a white foam:

MS(m/e): 389.0 (M$^+$)

Calculated for C$_{16}$H$_{25}$BrN$_2$O$_4$0.5H$_2$O: Theory: C, 48.25; H, 6.58; N, 7.03. Found: C, 48.50; H, 6.65; N, 7.07

$^{13}$C NMR (D$_2$O): δ 175.3, 173.9, 70.1, 64.9, 63.0, 54.8, 44.3, 43.0, 40.2, 35.0, 32.8, 32.7, 31.1, 28.7, 27.5, 24.7 ppm

EXAMPLE 10

Preparation of 3S, 4aR, 6S, 8aR 6-(((2S)-2-(Carboxylic acid)-(4S)$_4$(2-methyl-2H-tetrazol-5-ylsulfanyl)pyrrolidinyl)methyl-1,2,3,4,4a,5,6,7,8,8a-decahydroisoquinoline-3-carboxylic Acid

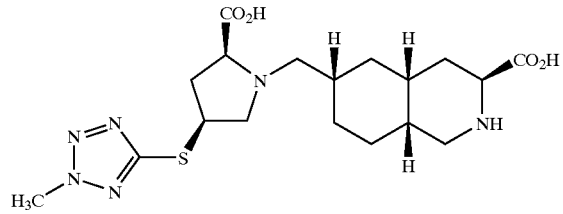

A. Preparation of 3S, 4aR, 6S, 8aR Ethyl 6-(((2S)-2-(Ethoxycarbonyl)-(4R)-4-(methanesulfonyloxy)pyrrolidinyl)methyl)-2-methoxycarbonyl-1,2,3,4,4a,5,6,7,8, 8a-decahydroisoquinoline-3-carboxylate To a solution of 3S, 4aR, 6S, 8aR ethyl 6-(((2S)-2-(ethoxycarbonyl)(4R)-4-hydroxypyrrolidinyl)methyl)-2-methoxycarbonyl-1,2,3,4,4a,5,6,7,8,8a-decahydroisoquinoline-3-carboxylate, the compound of Step B described in the preparation of Example 1 above (5.0 g, 11.3 mmol), cooled to 0° C. in CH$_2$Cl$_2$ (25 mL), was added triethylamine (1.90 mL, 13.6 mmol) followed by methanesulfonyl chloride (1.05 mL, 13.6 mmol). The reaction was warmed to room temperature, stirred for 20 h, and then quenched by the addition of 10% aqueous NaHSO$_4$. The aqueous layer was extracted with CH$_2$Cl$_2$, and the combined organics were dried (MgSO$_4$) and concentrated in vacuo. Column chromatography (50% EtOAc/hexane) provided 3.3 g (57%) of the desired intermediate title compound.

B. Preparation of 3S, 4aR, 6S, 8aR Ethyl 6-(((2S)$_2$-(Ethoxycarbonyl)-(4S)$_{42}$H-tetrazol-5-ylsulfanyl)pyrrolidinyl)methyl)-2-methoxycarbonyl-1,2,3,4,4a,5,6,7,8, 8a-decahydroisoquinoline-3-carboxylate To a solution of 3S, 4aR, 6S, 8aR ethyl 6-(((2S)-2-(ethoxycarbonyl)(4R)-4-(methanesulfonyloxy)pyrrolidinyl)methyl)-2-methoxycarbonyl-1,2,3,4,4a,5,6,7,8,8a-decahydroisoquinoline-3-carboxylate, the compound of Step A described in the preparation above (2.0 g, 3.86 mmol), dissolved in acetonitrile (6 mL), was added thiotetrazole (1.18 g, 11.6 mmol) followed by potassium carbonate (0.80 g, 5.79 mmol). The reaction was heated at 80° C. for 60 h, then partitioned between CH$_2$Cl$_2$ and H$_2$O. The aqueous layer was extracted with CH$_2$Cl$_2$, and the combined organics were dried (MgSO$_4$) and concentrated in vacuo. Column chromatography (75% EtOAc/hexane, then 5% EtOH/CH$_2$Cl$_2$) provided 0.96 g (47%) of the desired intermediate title compound.

C. Preparation of 3S, 4aR, 6S, 8aR Ethyl 6-(((2S)-2-(Ethoxycarbonyl)-(4S)$_4$(2-methyl-2H-tetrazol-5-ylsulfanyl)pyrrolidinyl)methyl)-2-methoxycarbonyl-1, 2, 3, 4, 4a, 5, 6, 7, 8, 8a-decahydroisoquinoline-3-carboxylate A solution of the compound of Step B above (0.48 g, 0.92 mmol), dissolved in THF (5 mL), was charged with NaH (60% dispersion in mineral oil) (0.04 g, 0.92 mmol), and stirred at room temperature for 10 min. Iodomethane (0.05 mL, 0.87 mmol) was added, and the reaction was heated at 45° C. for 48 h. The reaction was partitioned between CH$_2$Cl$_2$ and 10% aqueous NaHSO$_4$, the aqueous layer was extracted with CH$_2$Cl$_2$, and the combined organics were dried (MgSO$_4$) and concentrated in vacuo. The resulting residue was chromatographed (Stepwise gradient: 20%–50% EtOAc/hexane) to provide 0.16 g (32%) of the desired intermediate title compound (Isomer 1), as well as 0.10 g (20%) of the 1-methyl-tetrazole regioisomer (Isomer 2):

Ms(m/e): 539.1 (M$^+$)

D. Preparation of 3S, 4aR, 6S, 8aR 6-(((2S)$_2$-(Carboxylic acid)-(4S)$_4$(2-metyl-2H-tetrazol-5-ylsulfanyl)pyrrolidinyl)methyl)-1,2,3,4,4a,5,6,7,8,8a-decahydroisoquinoline-3-carboxylic Acid A solution of 3S, 4aR, 6S, 8a ethyl 6-(((2S)-2-(ethoxycarbonyl)-(4S)$_4$-(2-methyl-2H-tetrazol-5-ylsulfanyl)pyrrolidinyl)methyl)-2-methoxycarbonyl-1, 2, 3, 4, 4a, 5, 6, 7, 8, 8a-decahydroisoquinoline-3-carboxylate (0.16 g, 0.30 mmol), Isomer 1 of Step C above, dissolved in 5 N aqueous HCl (10 mL), was heated at 90° C. for 20 h. The reaction mixture was cooled to room temperature and concentrated in vacuo. The resulting crude foam was dissolved in H$_2$O (50 mL) and stirred in the presence of Dowex 50×8 (100 200) ion-exchange resin (3 g) for 2 h. The resin was filtered, washed sequentially with 1:1 THF/H$_2$O and H$_2$O, then stirred in the presence of 10% pyridine/H$_2$O (75 mL) for 2 h. After filtration, the resin was washed with H$_2$O, and the filtrate was concentrated in vacuo to provide the title compound (0.11 g, 87%) as a white foam:

MS(m/e): 425.2 (M$^+$)

Calculated for $C_{18}H_{28}N_6O_4S0.5H_2O$: Theory: C, 49.87; H, 6.74; N, 19.39. Found: C, 50.06; H, 6.59; N, 18.68

$^{13}$C NMR (D$_2$O): δ 175.0, 172.4, 161.3, 69.8, 62.2, 59.8, 54.4, 42.5, 41.6, 40.4, 35.4, 34.5, 32.4, 32.2, 30.7, 28.3, 27.0, 24.4 ppm

EXAMPLE 11

Preparation of 3S, 4aR, 6S, 8aR 6-(((2S)-2-(Carboxylic acid)-(4S) 4(1-methyl-1H-tetrazol-5-ylsulfanyl)pyrrolidinyl)methyl)-1,2,3,4,4a,5,6,7,8,8a-decahydroisoquinoline-3-carboxylic Acid

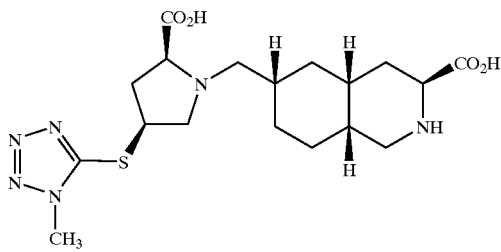

A solution of 3S, 4aR, 6S, 8aR ethyl 6-(((2S)-2-(ethoxycarbonyl)-(4S)-1-methy-1H-tetrazol-5-ylsulfonyl)pyrrolidinyl)methyl)-2-methoxycarbonyl-1, 2, 3, 4, 4a, 5, 6, 7, 8, 8a decahydroisoquinoline-3-carboxylate (0.10 g, 0.19 mmol), Isomer 2 from Step C of Example 10 above, dissolved in 5 N aqueous HCl (10 mL), was heated at 90° C. for 20 h. The reaction mixture was cooled to room temperature and concentrated in vacuo. The resulting crude foam was dissolved in H$_2$O (50 mL) and stirred in the presence of Dowex 50×8 (100–200) ion-exchange resin (3 g) for 2 h. The resin was filtered, washed sequentially with 1:1 THF/H$_2$O and H$_2$O, then stirred in the presence of 10% pyridine/H$_2$O (75 mL) for 2 h. After filtration, the resin was washed with H$_2$O, and the filtrate was concentrated in vacuo to provide the title compound (0.08 g, 95%) as a white foam:

MS(m/e): 425.2 (M$^+$)

Calculated for $C_{18}H_{28}N_6O_4S0.75H_2O$: Theory: C, 49.36; H, 6.79; N, 19.19. Found: C, 49.08; H. 6.58; N, 18.39

$^{13}$C NMR (D$_2$O): δ 174.9, 172.3, 153.6, 69.8, 62.1, 60.1, 54.4, 42.5, 42.3, 35.5, 34.5, 34.3, 32.4, 32.2, 30.7, 28.3, 27.0, 24.4 ppm

EXAMPLE 12

Preparation of 3S, 4aR, 6S, 8aR 6-(((2S)-2-(Carboxylic acid)(4R)$_4$-(1H-(1, 2, 4)triazol-3-ylsulfanyl)pyrrolidinyl)methyl)1, 2, 3, 4, 4a, 5, 6, 7, 8, 8a-decahydroisoquinoline-3-carboxylic Acid

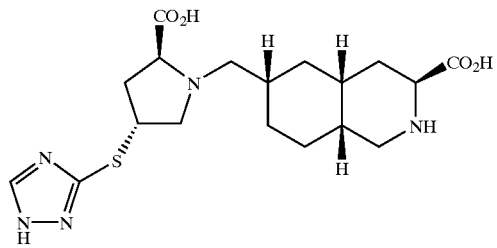

A. Preparation of 3S, 4aR, 6S, 8aR Ethyl 6-(((2S)-2-(Ethoxycarbonyl)(4S)4-bromopyrrolidinyl)methyl)-2-methoxycarbonyl-1,2,3,4,4a,5,6,7,8,8a-decahydroisoquinoline-3-carboxylate A mixture of triphenylphosphine (0.89 g, 3.40 mmol) and Br$_2$ (0.17 mL, 3.40 mmol) dissolved in CH$_2$Cl$_2$ (5 mL) was stirred at room temperature for 0.25 h. A solution of 3S, 4aR, 6S, 8aR ethyl 6-(((2S)-2-(ethoxycarbonyl)$_4$R)-4-hydroxypyrrolidinyl)methyl)-2-methoxycarbonyl-1,2,3,4,4a,5,6,7,8,8a-decahydroisoquinoline-3-carboxylate (1.00 g, 2.27 mmol), the compound of Step B described in the preparation of Example 1 above, and pyridine (0.37 mL, 4.54 mmol) dissolved in CH$_2$Cl$_2$ (10 mL), was added, and the reaction was stired at room temperature for 20 h. The reaction was partitioned between CH$_2$Cl$_2$ and 10% aqueous NaHSO$_4$, the aqueous layer was extracted with CH$_2$Cl$_2$, and the combined organics were dried (MgSO$_4$) and concentrated in vacuo. After rotary evaporation, the resulting residue was chromatographed (25% EtOAc/hexane) to provide 0.66 g (58%) of the desired intermediate title compound.

B. Preparation of 3S, 4aR, 6S, 8aR Ethyl 6-(((2S)-2-(Ethoxycarbonyl)-(4R)$_4$(1H (1, 2, 4)triazol-3-ylsulfanyl)pyrrolidinyl)methyl)-2-methoxycarbonyl-1, 2, 3, 4, 4a, 5, 6, 7, 8, 8a-decahydroisoquinoline-3-carboxylate To a solution of the compound of Step A described in the preparation above (0.66 g, 1.31 mmol), dissolved in acetonitrile (2 mL), was added thiotriazole (0.40 g, 3.93 mmol) followed by potassium carbonate (0.27 g, 1.97 mmol). The reaction was heated at 80° C. for 96 h, then partitioned between CH$_2$Cl$_2$ and H$_2$O. The aqueous layer was extracted with CH$_2$Cl$_2$, and the combined organics were dried (MgSO4) and concentrated in vacuo. Column chromatography (50% EtOAc/hexane, then 5% EtOH/CH$_2$Cl$_2$) provided 0.60 g (87%) of the desired intermediate title compound:

MS(m/e): 524.3 (M$^+$)

Calculated for $C_{24}H_{37}N_5O_6S.0.75H_2O$: Theory: C, 53.67; H, 7.22; N, 13.04. Found: C, 53.64; H, 6.91; N, 12.94

C. Preparation of 3S, 4aR, 6S, 8aR 6-(((2S)-2-(Carboxylic acid)-4R-4-(1H-(1,2,4)triazol-3-ylsulfanyl)pyrrolidinyl)methyl)-1,2,3,4,4a,5,6,7,8,8a-decahydroisoquinoline-3-carboxylic Acid A solution of 3S, 4aR, 6S, 8aR ethyl 6(((2S)$_2$-(ethoxycarbonyl)(4S)$_4$(1H-(1, 2, 4)triazol-3-ylsulfanyl)pyrrolidinyl)methyl)-2-methoxycarbonyl-1, 2, 3, 4, 4a, 5, 6, 7, 8, 8a-decahydroisoquinoline-3-carboxylate (0.59 g, 1.13 mmol), the compound of Step B above, dissolved in 5 N aqueous HCl (15 mL), was heated at 90° C. for 20 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 $THF/H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.36 g, 78%) as a white foam:

MS(m/e): 410.3 (M$^+$)

Calculated for $C_{18}H_{27}N_5O_4S.0.25H_2O$: Theory: C, 52.22; H, 6.70; N, 16.92. Found: C, 52.00; H, 6.70; N, 16.55

EXAMPLE 13

Preparation of 3S, 4aR, 6S, 8aR 6-(((2S)$_2$-(Carboxylic acid)-(4S)$_4$(1H-(1, 2, 4)triazol-3-ylsulfanyl)pyrrolidinyl)methyl)-1,2,3,4, 4a, 5, 6, 7, 8, 8a decahydroisoquinoline-3-carboxylic Acid

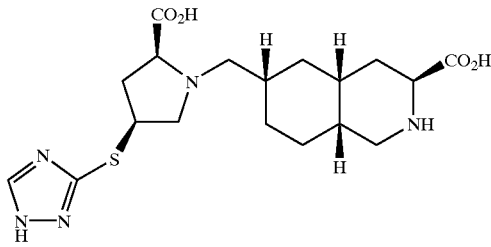

A. Preparation of 3S, 4aR, 6S, 8aR Ethyl 6-(((2S)$_2$-(Ethoxycarbonyl)-(4S)$_4$(1H-(1, 2, 4)triazol-3-ylsulfanyl)pyrrolidinyl)methyl)-2-methoxycarbonyl-1, 2, 3, 4, 4a, 5, 6, 7, 8, 8a-decahydroisoquinoline-3-carboxylate To a solution of 3S, 4aR, 6S, 8aR ethyl 6-(((2S)-2-ethoxycarbonyl)-(4R)-4-(methanesulfonyloxy)pyrrolidinyl)methyl)$_2$-methoxycarbonyl-1,2,3,4,4a,5,6,7,8,8a-decahydroisoquinoline-3-carboxylate, the compound of Step B described in the preparation of Example 10 above (1.0 g, 1.93 mmol), dissolved in acetonitrile (2 mL) was added thiotriazole (0.58 g, 5.78 mmol) followed by potassium carbonate (0.40 g, 2.90 mmol). The reaction was heated at 80° C. for 48 h, then partitioned between $CH_2Cl_2$ and $H_2O$. The aqueous layer was extracted with $CH_2Cl_2$, and the combined organics were dried ($MgSO_4$) and concentrated in vacuo. Column chromatography (50% EtOAc/hexane, then 5% MeO/$CH_2Cl_2$) provided 0.87 g (86%) of the desired intermediate title compound:

MS(m/e): 524.4 (M$^+$)

Calculated for $C_{18}H_{27}N_5O_4S.0.5H_2O$: Theory: C, 54.12; H, 7.19; N, 13.15. Found: C, 54.04; H, 6.85; N, 13.07

$^{13}$C NMR ($D_2O$): δ 175.1, 172.7, 146.7, 70.1, 69.4, 62.9, 60.1, 54.5, 42.5, 41.5, 35.3, 34.5, 32.4, 32.2, 30.7, 28.3, 27.0, 24.4 ppm D. Preparation of 3S, 4aR, 6S, 8aR 6-(((2S)-2Carboxylic acid)(4S)$_4$(1H-(1, 2, 4)triazol-3-ylsulfanyl)pyrrolidinyl)methyl)1, 2, 3, 4, 4a, 5, 6, 7, 8, 8a-decahydroisoquinoline-3-carboxylic Acid A solution of 3S, 4aR, 6S, 8aR ethyl 6-(((2S2-(ethoxycarbonyl)-(4S)$_4$(1H-(1, 2, 4)triazol-3-ylsulfanyl)pyrrolidinyl)methyl)$_2$-methoxycarbonyl-1, 2, 3, 4, 4a, 5, 6, 7, 8, 8a-decahydroisoquinoline-3-carboxylate (0.79 g, 1.51 mmol), the compound of Step A above, dissolved in 5 N aqueous HCl (20 mL), was heated at 90° C. for 17 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 $THF/H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.60 g, 97%) as a white foam:

MS(m/e): 410.3 (M$^+$)

Calculated for $C_{18}H_{27}N_5O_4S.0.7H_2O$: Theory: C, 51.22; H, 6.78; N, 16.59. Found: C, 51.56; H, 6.65; N, 16.29

$^{13}$C NMR ($D_2O$): δ 175.1, 172.4, 146.6, 70.1, 69.5, 61.6, 60.0, 54.5, 42.5, 41.0, 35.5, 34.6, 32.7, 32.1, 30.7, 28.2, 27.0, 24.1 ppm

EXAMPLE 14

Preparation of 3S, 4aR, 6S, 8aR 6-(((2S)$_2$-(Carboxylic acid)-(4R)$_4$(1H-tetrazol-5-ylsulfanyl)pyrrolidinyl)methyl)-1,2, 3, 4, 4a, 5, 6, 7, 8, 8a-decahydroisoquinoline-3-carboxylic Acid

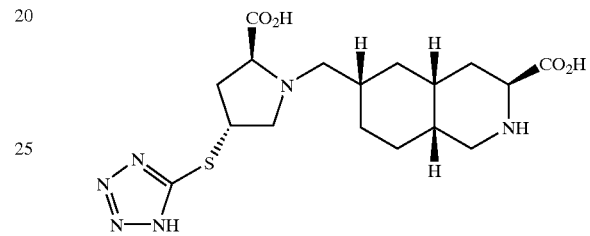

A. Preparation of 3S, 4aR, 6S, 8aR Ethyl 6-(((2S)-2-(Ethoxycarbonyl)-(4R)-4-(1H-tetrazo-5-ylsulfanyl)pyrrolidinyl)methyl)-2-methoxycarbonyl-1,2,3,4,4a,5,6,7,8,8a-decahydroisoquinoline-3-carboxylate A solution of 3S, 4aR, 6S, 8aR ethyl 6-(((2S)-2-methoxycarbonyl)-(4S)-4-bromopyrrolidinyl)methyl)-2-methoxycarbonyl-1,2,3,4,4a,5,6,7,8,8a-decahydroisoquinoline-3-carboxylate (0.64 g, 1.27 mmol), the compound of Step A described in the preparation of Example 12 above, dissolved in acetonitrile (1.25 mL) was added thiotetrazole (0.52 g, 5.09 mmol) followed by potassium carbonate (0.35 g, 2.54 mmol). The reaction was heated at 80° C. for 72 h, then partitioned between $CH_2Cl_2$ and $H_2O$. The aqueous layer was extracted with $CH_2Cl_2$, and the combined organics were dried ($MgSO_4$) and concentrated in vacuo. Column chromatography (50% EtOAc/hexane, then 5% EtOH/$CH_2Cl_2$) provided 0.19 g (29%) of the desired intermediate title compound:

MS(m/e): 525.3 (M$^+$)

B. Preparation of 3S, 4aR, 6S, 8aR 6-(((2S2-(Carboxylic acid)-(4R)-4-(1H-tetrazol-5-ylsulfanyl)pyrrolidinyl)methyl)-1,2,3,4,4a,5,6,7,8,8a-decahydroisoquinoline-3-carboxylic Acid A solution of the compound of Step A above (0.17 g, 0.32 mmol), dissolved in 5 N aqueous HCl (10 mL), was heated at 90° C. for 19 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 $THF/H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.10 g, 71%) as a white foam:

MS(m/e): 411.2 (M$^+$)

EXAMPLE 15

Preparation of 3S, 4aR, 6S, 8aR 6((2S)-2-(Carboxylic acid)-(4S)-4-(Carboxylic acid methylsulfanyl)pyrrolidinyl)methyl)-1,2, 3, 4, 4a, 5, 6, 7, 8, 8a-decahydroisoquinoline-3-carboxylic Acid

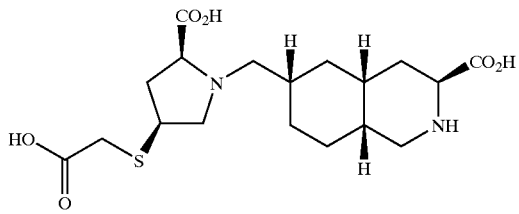

A. Preparation of Ethyl 2S, 4S4-Acetylsulfanylpyrrolidine-1-(tert-butoxycarbonyl)-2-carboxylate A solution of cis-4-hydroxy-L-proline-hydrochloride (3.0 g, 15.3 mmol) dissolved in $CH_2Cl_2$ (25 mL) was stirred at room temperature in the presence of triethylamine (6.4 mL, 46.0 mmol). After 0.25 h, di-tert-butyl dicarbonate (4.2 mL, 18.4 mmol) was added. The reaction was stirred at room temperature for 22 h, then partitioned between $Et_2O$ and $H_2O$. The organic layer was dried over $MgSO_4$ and concentrated in vacuo. Column chromatography (10% MeOH/ $CH_2Cl_2$) provided 4.0 g (93%) of ethyl 2S, 4R-1tert-butoxycarbonyl)-4-hydroxypyrrolidine-2-carboxylate.

A solution of triphenylphosphine (8.1 g, 30.8 mmol) and diethyl azodicarboxylate (4.1 mL, 30.8 mmol) cooled to 0° C. in THF (50 mL) was stirred for 0.5 h, whereupon ethyl 2S, 4R-1-(tert-butoxycarbonyl)-4-hydroxypyrrolidine-2-carboxylate (4.0 g, 15.4 mmol), dissolved in THF (20 mL), and thioacetic acid (2.2 mL, 30.8 mmol) were added. The reaction was stirred at 0° C. for 1 h, then warmed to room temperature and stirred for an additional 18 h. The reaction was concentrated in vacuo, then $Et_2O$ (100 mL) was added, and the residual solid was removed by vacuum filtration. The filtrate was concentrated in vacuo and chromatographed (20% EtOAc/hexane) to provide 4.40 g (90%) of the intermediate title compound.

B. Preparation of Ethyl 2S, 4S4-Ethoxycarbonylmethylsulfanylpyrrolidine-2-carboxylate To a solution of the intermediate of Step A described above (2.20 g, 6.93 mmol) dissolved in MeOH (20 mL) was added a solution of 1N aqueous NaOH (7.6 mL, 7.6 mmol), followed, after 0.5 h, by ethyl bromoacetate (0.84 mL, 7.6 mmol). The reaction was stirred at room temperature for 2 h, then partitioned between $CH_2Cl_2$ and 10% saturated aqueous $NaHSO_4$. The aqueous layer was extracted with $CH_2Cl_2$, and the combined organics were dried ($MgSO_4$) and concentrated in vacuo. Column chromatography (25% EtOAc/hexane) provided 2.0 g (5.5 mmol) of the BOC-protected intermediate. This material was dissolved in 1 N HCl/EtOAc (20 mL), the reaction was stirred at room temperature for 42 h, then concentrated. Acetone was added, then removed in vacuo. The residue was taken up in a solution of 2 M $NH_3$/EtOH (5 mL), the resulting salt was removed by vacuum filtration, and the filtrate was concentrated in vacuo. Column chromatography (50% EtOAc/hexane) provided the titled intermediate (1.28 g, 95%).

C. Preparation of 3S, 4aR, 6S, 8aR Ethyl 6-(((2S2 (Ethoxycarbonyl)(4S)-4-(Ethoxycarbonylmethylsulfanyl)pyrrolidinyl)methyl)-2-methoxycarbonyl-1, 2, 3, 4, 4a, 5, 6, 7, 8, 8a-decahydroisoquinoline-3-carboxylate To a solution of 1.0 g (2.2 mmol) of 3S, 4aR, 6S, 8aR ethyl 6-((4- methylphenyl)sulfonyloxy)methyl)-2-methoxycarbonyl-1,2,3,4,4a,5,6,7,8,8a-decahydroisoquinoline-3-carboxylate, the compound of Step A of Example 1 described above, dissolved in $CH_3CN$ (2.0 mL) was added $K_2CO_3$ (0.46 g, 3.3 mmol) followed by ethyl 2S, 4S4-ethoxycarbonylmethylsulfanylpyrrolidine-2-carboxylate, the compound of Step B above (0.81 g, 3.1 mmol). The reaction mixture was heated at 80° C. for 72 h, cooled to room temperature, then partitioned between $CH_2Cl_2$ and $H_2O$. The aqueous layer was extracted with $CH_2Cl_2$, and the combined organics were dried ($MgSO_4$), and concentrated. The resulting residue was chromatographed (50% EtOAc/hexane) to provide 0.88 g (74%) of the desired intermediate title compound:

MS(m/e): 543.3 ($M^+$)

Calculated for $C_{26}H_{42}N_2O_8S$: Theory: C, 57.54; H, 7.80; N, 5.16. Found: C, 57.57; H, 7.67; N, 5.22

D. Preparation of 3S, 4aR, 6S, 8aR 6((2S)$_2$-(Carboxylic acid)-(4S)-4-(Carboxylic acid methylsulfanyl)pyrrolidinyl)methyl)-1,2,3,4,4a,5,6,7,8,8a-decahydroisoquinoline-3-carboxylic Acid A solution of the compound of Step C above (0.87 g, 0.1.6 mmol), dissolved in 5 N aqueous HCl (20 mL), was heated at 90° C. for 18 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 THF/$H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.53 g, 83%) as a white foam:

MS(m/e): 401.2($M^+$)

Calculated for $C_{18}H_{28}N_2O_6S \cdot 0.5H_2O$: Theory: C, 52.79; H, 7.14; N, 6.84.

Found: C, 52.74; H, 6.80; N, 6.65

$^{13}$C NMR ($D_2O$): δ 176.0, 175.2, 173.4, 70.1, 63.0, 60.9, 54.7, 43.0, 41.7, 36.2, 35.3, 34.9, 32.7, 32.6, 31.1, 28.8, 27.5, 24.9 ppm

EXAMPLE 16

Preparation of 3S, 4aR, 6S, 8aR 6-(((2S)-2-(Carboxylic acid)-(4S)-4-(methylsulfanyl)pyrrolidinyl)methyl)-1,2,3,4, 4a,5,6,7,8,8a-decahydroisoquinoline-3-carboxylic Acid

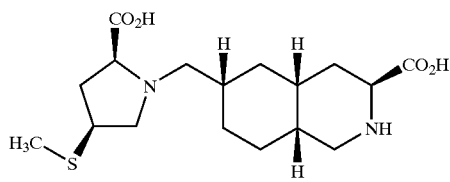

A. Preparation of Ethyl 2S, 4S-4-Methylsulfanylpyrrolidine-2-carboxylate

To a solution of the intermediate of Step A described in the preparation of Example 15 above (2.2 g, 6.9 mmol) dissolved in MeOH (20 mL) was added a solution of 1N aqueous NaOH (7.6 mL, 7.6 mmol), followed, after 0.5 h, by dimethylsulfate (0.72 mL, 7.6 mmol). The reaction was stirred at room temperature for 2 h, then partitioned between $CH_2Cl_2$ and 10% saturated aqueous $NaHSO_4$. The aqueous layer was extracted with $CH_2Cl_2$, and the combined organics were dried ($MgSO_4$) and concentrated in vacuo. Column chromatography (25% EtOAc/hexane) provided 1.6 g (5.4 mmol) of the BOC-protected intermediate. This material was dissolved in 1 N HCl/EtOAc (17.4 mL), the reaction was stirred at room temperature for 42 h, then concentrated. Acetone was added, then removed in vacuo. The residue was taken up in a solution of 2 M $NH_3$/EtOH (5 mL), the resulting salt was removed by vacuum filtration, then the filtrate was concentrated in vacuo. Column chromatography (50% EtOAc/hexane then 5% MeOH/$CH_2Cl_2$) provided the titled intermediate (0.73 g, 89%).

B. Preparation of 3S, 4aR, 6S, 8aR Ethyl 6-(((2S)-2-(Ethoxycarbonyl)-(4S)-4-(methylsulfanyl)pyrrolidinyl)methyl)-2-methoxycarbonyl-1,2,3,4,4a,5,6,7,8,8a-decahydroisoquinoline-3-carboxylate To a solution of 1.0 g (2.2 mmol) of 3S, 4aR, 6S, 8aR ethyl 6-((4-methylphenyl)sulfonyloxy)methyl)-2-methoxycarbonyl-1,2,3,4,4a,5,6,7,8,8a-decahydroisoquinoline-3-carboxylate, the compound of Step A of Example 1 described above, dissolved in $CH_3CN$ (2.0 mL) was added $K_2CO_3$ (0.46 g, 3.3 mmol), followed by ethyl 2S, 4S-4-methylsulfanylpyrrolidine-2-carboxylate, the compound of Step A above (0.73 g, 3.9 mmol). The reaction mixture was heated at 80° C. for 72 h, cooled to room temperature, then partitioned between $CH_2Cl_2$ and $H_2O$. The aqueous layer was extracted with $CH_2Cl_2$, and the combined organics were dried ($MgSO_4$), and concentrated. The resulting residue was chromatographed (50% EtOAc/hexane) to provide 0.78 g (75%) of the desired intermediate title compound:

MS(m/e): 471.3 ($M^+$)

Calculated for $C_{23}H_{38}N_2O_6S \cdot 0.5H_2O$: Theory: C, 57.60; H, 8.20; N, 5.84.

Found: C, 57.23; H, 7.96; N, 6.03

C. Preparation of 3S, 4aR, 6S, 8aR 6-(((2S)-2-Carboxylic acid)-(4S)-4-(methylsulfanyl)pyrrolidinyl)methyl)-1,2,3,4,4a,5,6,7,8,8a-decahydroisoquinoline-3-carboxylic Acid A solution of the compound of Step B above (0.77 g, 0.1.6 mmol), dissolved in 5 N aqueous HCl (25 mL), was heated at 80° C. for 72 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 THF/$H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.45 g, 77%) as a white foam:

MS(m/e): 357.3 ($M^+$)

Calculated for $C_{18}H_{28}N_2O_6S \cdot 0.25H_2O$: Theory: C, 56.57; H. 7.96; N, 7.76. Found: C, 56.37; H, 7.85; N, 7.72

$^{13}C$ NMR ($D_2O$): δ 175.6, 173.7, 70.2, 63.0, 60.7, 54.9, 43.0, 42.5, 35.8, 34.9, 32.9, 32.7, 31.1, 28.8, 27.5, 24.9, 14.5 ppm

EXAMPLE 17

Preparation of 3S, 4aR, 6S, 8aR 6-(((2S)-2(Carboxylic acid)-(4S)-4-(1H-tetrazol-5-ylsulfanyl)pyrrolidinyl)methyl)-1,2, 3, 4, 4a, 5, 6, 7, 8, 8a-decahydroisoquinoline-3-carboxylic Acid

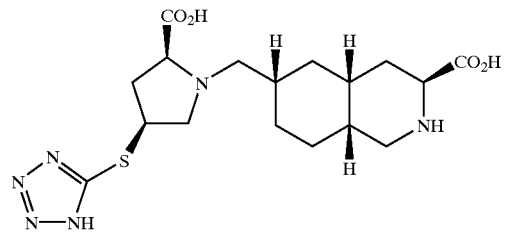

A. Preparation of 3S, 4aR, 6S, 8aR Ethyl 6-(((2S)-2-(Ethoxycarbonyl)-(4S)$_4$(1H-tetrazol-5-ylsulfanyl)pyrrolidinyl)methyl)$_2$-methoxycarbonyl-1,2,3,4,4a,5,6,7,8, 8a-decahydroisoquinoline-3-carboxylate A solution of 3S, 4aR, 6S, 8aR ethyl 6(((2S)-2-(ethoxycarbonyl)(4R)$_4$-bromopyrrolidinyl)methyl)-2-methoxycarbonyl-1,2,3,4,4a,5,6,7,8,8a-decahydroisoquinoline-3-carboxylate (0.79 g, 1.57 mmol), the compound of Step B described in the preparation of Example 6 above, dissolved in acetonitrile (1.5 mL) was added thiotetrazole (0.64 g, 6.28 mmol) followed by potassium carbonate (0.43 g, 3.14 mmol). The reaction was heated at 80° C. for 120 h, then partitioned between $CH_2Cl_2$ and $H_2O$. The aqueous layer was extracted with $CH_2Cl_2$, and the combined organics were dried ($MgSO_4$) and concentrated in vacuo. Column chromatography (50% EtOAc/hexane, then 5% EtOH ($CH_2Cl_2$) provided 0.44 g (53%) of the desired intermediate title compound:

MS(m/e): 525.3 ($M^+$)

B. Preparation of 3S, 4aR, 6S, 8aR 6((2S)-2-(Carboxylic acid)-(4S)$_4$(1H-tetrazol-5-ylsulfanyl)pyrrolidinyl)methyl)-1,2,3,4,4a,5,6,7,8,8a-decahydroisoquinoline-3-carboxylic Acid A solution of the compound of Step A above (0.30 g, 0.57 nmol), dissolved in 5 N aqueous HCl (15 mL), was heated at 90° C. for 18 h. The reaction mixture was cooled to room temperature and concentrated in vacuo. The resulting crude foam was dissolved in $H_2O$ (50 mL) and stirred in the presence of Dowex 50×8 (100–200) ion-exchange resin (3 g) for 2 h. The resin was filtered, washed sequentially with 1:1 THF/$H_2O$ and $H_2O$, then stirred in the presence of 10% pyridine/$H_2O$ (75 mL) for 2 h. After filtration, the resin was washed with $H_2O$, and the filtrate was concentrated in vacuo to provide the title compound (0.23 g, 98%) as a white foam:

MS(m/e): 411.2($M^+$)

$^{13}C$ NMR ($D_2O$): δ 183.3, 181.3, 149.5, 70.9, 62.5, 61.0, 56.3, 44.3, 42.4, 38.1, 37.5, 36.9, 35.0, 34.6, 31.2, 29.4, 27.2 ppm

EXAMPLE 18

Preparation of 3S, 4aR, 6S, 8aR 6-(((2R)-2-(Carboxylic acid)4,4-difluoropyrrolidinyl)methyl)-1,2, 3, 4, 4a, 5, 6, 7, 8, 8a-decahydroisoquinoline-3-carboxylic Acid

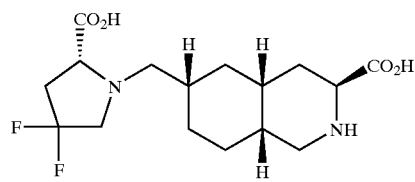

A. Preparation of 3S, 4aR, 6S, 8aR Ethyl 6((2R)-(Ethoxycarbonyl)-(4S)-4hydroxypyrrolidinyl)methyl)-2-methoxycarbonyl-1,2,3,4,4a,5,6,7,8,8a-decahydroisoquinoline-3-carboxylate A solution of cis-4-hydroxy-D-proline methyl ester hydrochloride (4.0 g, 2.1 mmol) dissolved in acetonitile (20 mL) was stirred in the presence of triethylamine (3.1 mL, 22.1 mmol) for 0.25 h. A solution of 4.0 g (11.0 mmol) of 3S, 4aR, 6S, 8aR ethyl 6-bromomethyl-2-methoxycarbonyl-decahydroisoquinoline-3-carboxylate (prepared by one of ordinary skill in the art following the procedures as disclosed in U.S. Pat. No. 5,670,516) dissolved in $CH_3CN$ (30 mL) was added, followed by potassium carbonate (2.3 g, 2.28 mmol). The reaction was heated at reflux for 96 h, the reaction mixture was cooled to room temperature, then partitioned between $CH_2Cl_2$ and $H_2O$. The aqueous layer was extracted two times with $CH_2Cl_2$ and the combined organics were dried over $MgSO_4$, filtered, and concentrated in vacuo. Column chromatography (50% EtOAc/hexane followed by 10% MeOH/$CH_2Cl_2$) gave 1.92 g (41%) of the desired intermediate title compound as a colorless oil:

MS(m/e): 427.3 ($M^+$)

Calculated for $C_{21}H_{34}N_2O_7$: Theory: C, 59.14; H, 8.04; N, 6.57. Found: C, 58.85; H. 7.83; N, 6.62

B. Preparation of 3S, 4aR, 6S, 8aR Ethyl 6(((2R)-2(Ethoxycarbonyl)-4-oxopyxrolidinyl)methyl)-2-methoxycarbonyl-1,2,3,4,4a,5,6,7,8,8a-decahydroisoquinoline-3-carboxylate To a solution of DMSO (0.63 mL, 8.80 mmol) cooled to −78° C. in $CH_2Cl_2$ (10 mL) was added, dropwise, oxalyl chloride (0.37 mL, 4.20 mmol). The reaction mixture was stirred for 5 min, then the compound of Step A above (1.5 g, 3.52 mmol) dissolved in 10 mL of $CH_2Cl_2$ was added. Upon stirring for 45 min at −78° C., triethylamine (2.45 mL, 17.6 mmol) was added. The reaction was warmed to room temperature over approximately 2 hours, and quenched by the addition of 10% aqueous $NaHSO_4$. The aqueous layer was extracted with $CH_2Cl_2$ and the combined organics were dried over $MgSO_4$, filtered, and concentrated in vacuo. Column chromatography (50% EtOAc/hexane) provided 0.57 g (38%) of the desired intermediate title compound as a colorless oil.

C. Preparation of 3S, 4aR, 6S, 8aR Ethyl 6((2R)-2-(Ethoxycarbonyl)-4,4-difluoropyrrolidinyl)methyl)-2-methoxycarbonyl-1,2,3,4,4a,5,6,7,8,8a-decahydroisoquinoline-3-carboxylate.

To a mixture of the compound of Step B above (0.57 g, 1.34 mmol) cooled to −78° C. in $CH_2Cl_2$ (10 mL) was added, dropwise, diethylaminosulfur trifluoride (0.44 mL, 3.36 mmol). The reaction was allowed to warm to room temperature, stirred an additional 55 h, then quenched by the addition of MeOH. After concentrating in vacuo, the residue was partitioned between $CH_2Cl_2$ and saturated aqueous $NaHCO_3$. The aqueous layer was extracted with $CH_2Cl_2$ and the combined organics were dried over $MgSO_4$, filtered, and concentrated in vacuo. Column chromatography (stepwise gradient: 10–50% EtOAc/hexane) provided 0.51 g (85%) of the desired intermediate title compound as a colorless oil:

MS(m/e): 447.2($M^+$)

Calculated for $C_{21}H_{32}F_2N_2O_6 \cdot 0.5H_2O$: Theory: C, 55.38; H, 7.30; N, 6.16.

Found: C, 55.71; H. 7.03; N, 6.29

D. 3S, 4aR, 6S, 8aR 6-(((2R)-2-(Carboxylic acid)-4,4-difluoropyrrolidinyl)methyl)-1, 2, 3, 4, 4a, 5, 6, 7, 8, 8a-decahydroisoquinoline-3-carboxylic Acid A solution of 3S, 4aR, 6S, 8aR ethyl 6-(((2R)-2-(ethoxycarbonyl)4,4-difluoropyrrolidinyl)methyl)$_2$-methoxycarbonyl-1,2,3,4,4a,5,6,7,8,8a-decahydroisoquinoline-3-carboxylate (0.49 g, 1.10 mmol), the compound of Step C above, dissolved in 5 N aqueous HCl (15 mL) was heated at 90° C. for 18 h. The reaction mixture was cooled to room temperature and concentrated in vacuo. The resulting crude foam was dissolved in $H_2O$ (75 mL) and stirred in the presence of Dowex 50×8 (100–200) ion-exchange resin (10 g) for 2 h. The resin was filtered, washed sequentially with 1:1 THF/$H_2O$ and $H_2O$, then stirred in the presence of 10% pyridine/$H_2O$ for 2 h. After filtration, the resin was washed with $H_2O$, and the filtrate was concentrated in vacuo to provide the title compound (0.26 g, 68%) as a white foam:

MS(m/e): 345.1 ($M^+$)

Calculated for $C_{16}H_{24}F_2N_2O_4 \cdot 0.5H_2O$: Theory: C, 54.07; H, 7.09; N, 7.88. Found: C, 53.77; H, 6.93; N, 7.85

$^{13}C$ NMR ($D_2O$), δ174.8, 171.1, 125.6 (t, $J_{C-F}$=249.6 Hz), 68.1, 63.2, 59.4 (t, $J_{C-F}$=33.9 Hz), 54.3, 42.5, 37.5 (t, $J_{C-F}$=24.9 Hz), 34.3, 32.3, 32.4, 30.6, 28.5, 16.9, 24.1 ppm

EXAMPLE 19

Preparation of 3S, 4aR, 6S, 8aR 6-((3R)-3-(Carboxylic acid)(5S)-5-hyroxypiperidinyl)-1, 2, 3, 4, 4a, 5, 6, 7, 8, 8a-decahydroisoquinoline-3-carboxylic Acid

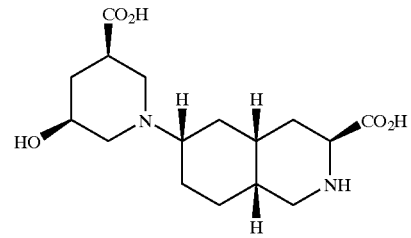

A. Preparation and resolution of 3R, 5S ethyl 5-hydroxypiperidine-3-carboxylate and 3S, 5R ethyl 5-hydroxypiperidine-3-carboxylate Anhydrous HCl was bubbled through a suspension of (±)-5-hydroxypiperidine-3-carboxylic acid (5.6 g, 38.6 mmol) (according to the procedures as disclosed in *J. Med. Chem.*, 25, 1157–1162, (1982)), cooled to 0° C. in EtOH (100 mL), until saturation was reached. The reaction mixture was warmed to room temperature, stirred overnight, then concentrated in vacuo. The crude salt was cooled to 0° C. in $CHCl_3$ (80 mL), and anhydrous $NH_3$ was bubbled through the solution. The resulting white precipitate was removed by vacuum filtration, and the filtrate was concentrated in vacuo to provide 6.6 g (99%) of (±) ethyl 5-hydroxypiperidine-3-carboxylate as a pale yellow oil.

To a solution of (±) ethyl 5-hydroxypiperidine-3-carboxylate (1.00 g, 5.77 nmol) dissolved in 95% EtOH (8.0 mL) was added p-toluoyl-D-tartaric acid (2.20 g, 5.77 mmol). Following complete dissolution of the acid, the solution remained at room temperature overnight. The resulting crystals were filtered and washed with cold 95% EtOH to provide 581 mg (1.04 mmol, 18%, 95% ee) of 3R,5S-(+) ethyl 5-hydroxypiperidine-3-carboxylate as the tartrate salt. Resolution to provide 3S,5R-(−) ethyl 5-hydroxypiperidine-3-carboxylate was performed in an analogous fashion, using p-toluoyl-L-tartaric acid. The absolute configuration of this isomer was assigned by x-ray crystallography.

Determination of % ee: A solution of 10 mg of the resulting salt (0.018 mmol), potassium carbonate (8 mg, 0.054 mmol), and (S)-(−)-MTPA (4 mL, 0.022 mmol), was stirred for 2 h at room temperature in 1 mL of 1:1 THF/$H_2O$. An aliquot of the reaction was removed and analyzed by reverse-phase HPLC (Hypersil BDS-C18 column, using a 0.1% TFA/ACN-0.1% TFA/H20 gradient system): RT 52.0 rain for (+) enantomer, 53.2 min for (−) enatiomer.

B. Preparation of 3S, 4aR, 6S, 8aR Ethyl 6-((3R)-Ethoxycarbonyl(5S)-5-hydroxypiperidinyl)-2-methoxycarbonyl-1,2,3,4,4a,5,6,7,8,8a-decahydroisoquinoline-3-carboxylate A mixture of 3R,5S-(+) ethyl 5-hydroxypiperidine-3-carboxylate (0.37 g. 2.13 mmol), 3S, 4aS, 8aS-(–) ethyl 2-methoxycarbonyl-6-oxodecahydroisoquinoline-3-carboxylate (1.21 g, 4.27 mmol) (prepared by one of ordinary skill in the art following the procedures as disclosed in U.S. Pat. No. 5,670,516), NaBH(OAc)$_3$ (0.90 g, 4.27 mmol), and HOAc (0.25 mL, 4.27 mmol) was stirred at room temperature in THF (15 mL) for 72 h. The reaction mixture was partitioned between 3:1 CHCl$_3$/IPA and saturated aqueous NaHCO$_3$, extracted with CHCl$_3$/IPA, washed with saturated aqueous NaCl, dried (MgSO$_4$), and concentrated. Chromatography (Stepwise gradient: CH$_2$Cl$_2$–5% MeOH/CH$_2$Cl$_2$) provided the titled compound (0.48 g, 52%):

MS(m/e): 441.3 (M$^+$)

Calculated for C$_{22}$H$_{36}$N$_2$O$_7$: Theory: C, 59.98; H, 8.24; N, 6.36. Found: C, 59.86; H, 8.00; N, 6.41

C. Preparation of 3S, 4aR, 6S, 8aR 6-((3R)-3-(Carboxylic acid)(5S)$_5$-hydroxypiperidinyl)-1,2, 3, 4, 4a, 5, 6, 7, 8, 8a-decahydroisoquinoline-3-carboxylic Acid A solution of the compound of Step B above (205 mg, 0.46 mmol) dissolved in 5 N aqueous HCl (10 mL) was heated at 95° C. for 12 h. The reaction mixture was cooled to room temperature and concentrated in vacuo. The resulting crude foam was dissolved in H$_2$O and stirred in the presence of Dowex 50×8 (100–200) ion-exchange resin for 4 h. The resin was filtered, washed sequentially with 1:1 THF/H$_2$O and H$_2$O, then stirred in the presence of 10% pyridine/H$_2$O for 12 h. After filtration, the resin was washed with H$_2$O, and the filtrate was concentrated in vacuo to provide the title compound (123 mg, 82%) as a white foam:

MS(m/e): 327.3 (M$^+$)

Calculated for C$_{16}$H$_{26}$N$_2$O$_5$0.75H$_2$O: Theory: C, 56.54; H, 8.16; N, 8.24.

Found: C, 56.34; H, 8.02; N, 8.09

$^{13}$C NMR (D$_2$O): □ 182.2, 175.9, 67.0, 63.3, 55.2, 54.7, 51.3, 43.5, 42.7, 36.9, 32.9, 32.8, 31.1, 27.1, 26.3, 22.0 ppm

EXAMPLE 20

Preparation of 3S, 4aR, 6S, 8aR 6-((3S)-3-carboxylic acid) (5R)-5-hydroxypiperidinyl)-1, 2, 3, 4, 4a, 5, 6, 7, 8, 8a-decahydroisoquinoline-3-carboxylic Acid

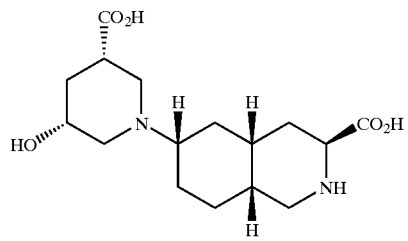

A. Preparation of 3S, 4aR, 6S, 8aR Ethyl 6-((3S)-(Ethoxycarbonyl)(5R)-5-hydroxypiperidinyl)-2-methoxycarbonyl-1,2,3,4,4a,5,6,7,8,8a-decahydroisoquinoline-3-carboxylate Employing the same method described for the preparation of the compound in Step B of Example 19, using 3S, 5R (–) ethyl 5-hydroxypiperidine-3-carboxylate, the preparation of which is described in Step A of Example 19, provided the title compound:

MS(m/e): 441.3 (M$^+$)

Calculated for C$_{22}$H$_{36}$N$_2$O$_7$: Theory: C, 59.98; H, 8.24; N, 6.36. Found: C, 60.40; H, 8.18; N, 6.47

B. Preparation of 3S, 4aR, 6S, 8aR 6-((3S)-3-(Carboxylic acid)-(5R)-5-hydroxypiperidinyl)-1,2,3,4,4a,5,6,7,8,8a-decahydroisoquinoline-3-carboxylic Acid A solution of the compound of Step A above (140 mg, 0.0.32 mmol) dissolved in 5 N aqueous HCl (10 mL) was heated at 95° C. for 12 h. The reaction mixture was cooled to room temperature and concentrated in vacuo. The resulting crude foam was dissolved in H$_2$O and stirred in the presence of Dowex 50×8 (100–200) ion-exchange resin for 4 h. The resin was filtered, washed sequentially with 1:1 THF/H$_2$O and H$_2$O, then stirred in the presence of 10% pyridine/H$_2$O for 12 h. After filtration, the resin was washed with H$_2$O, and the filtrate was concentrated in vacuo to provide the title compound (84 mg, 81%) as a white foam:

MS(m/e): 327.3 (M$^+$)

Calculated for C$_{16}$H$_{26}$N$_2$O$_5$1.5H$_2$O: Theory: C, 54.38; H. 8.27; N, 7.93.

Found: C, 54.69; H, 8.08; N, 7.62

$^{13}$C NMR (D$_2$O): □ 182.5, 67.2, 63.9, 55.8, 55.3, 51.6, 43.8, 43.7, 37.0, 36.1, 34.3, 34.0, 28.3, 27.0, 22.9 ppm

EXAMPLE 21

Preparation of 3S, 4aR, 6S, 8aR 6-((3S)-3-(Carboxylic acid)-(5S)-5-hydroxypiperidinyl)-1, 2, 3, 4, 4a, 5, 6, 7, 8, 8a-decahydroisoquinoline-3-carboxylic Acid

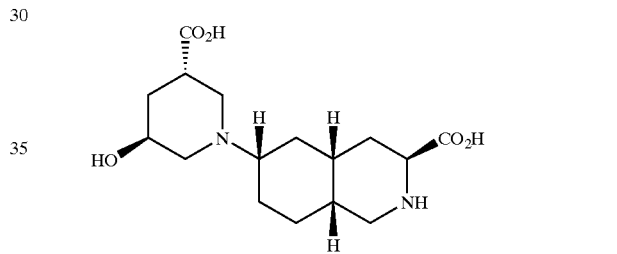

A. Preparation of 3S, 4aR, 6S, 8aR Ethyl 6-((3S)-(Ethoxycarbonyl){5S)-5-benzoyloxypiperidinyl)-2-methoxycarbonyl-1,2,3,4,4a,5,6,7,8,8a-decahydroisoquinoline-3-carboxylate A solution of 3S, 4aR, 6S, 8aR ethyl 6{(3S) (ethoxycarbonyl)-(5S)-5-hydroxypiperidinyl)$_2$-methoxycarbonyl-1,2,3,4,4a,5,6,7,8,8a-decahydroisoquinoline-3-carboxylate (0.52 g, 1.16 mmol), the compound of Step A described in the preparation of Example 20 above, cooled to 0° C. in THF (10 mL) was charged with triphenylphospine (1.22 g, 4.68 mmol), benzoic acid (0.57 g, 4.68 mmol), and diethyl azodicarboxylate (0.68 g, 4.68 mmol). After stirring at room temperature for 48 h, the reaction mixture was loaded onto a 5 g SCX Mega Bond Elut SPE cartridge (Varian Sample Preparation Products) and eluted with EtOH, followed by CH$_2$Cl$_2$. The product was removed with 2 M NH$_3$/EtOH, and the solution was concentrated then chromatographed (stepwise gradient: hexane-50% EtOAc/hexane), providing the intermediate title compound (0.51 g, 81%).

B. Preparation of 3S, 4aR, 6S, 8aR 6-((3S)-3-(Carboxylic acid)(5S)$_5$-hydroxypiperidinyl)-1,2,3,4,4a,5,6,7,8,8a-decahydroisoquinoline-3-carboxylic Acid A solution of the compound of Step A above (276 mg, 0.51 mmol) dissolved in 5 N aqueous HCl (15 mL) was heated at 95° C. for 12 h. The reaction mixture was cooled to room temperature and concentrated in vacuo. The resulting crude foam was dissolved in $H_2O$ and loaded onto a 5 g SCX Mega Bond Elut SPE cartridge. The cartridge was washed sequentially with $H_2O$ 1:1 $THF/H_2O$, and $H_2O$. The product was removed with 1:1 pyridine/$H_2O$, and concentrated to provide the title compound (139 mg, 84%) as a white foam:

MS(m/e): 325.3 (M⁻)

Calculated for $C_{16}H_{26}N_2O_5 \cdot 1.2H_2O$: Theory: C, 55.23; H, 8.23; N, 8.05.

Found: C, 54.87; H. 8.12; N, 8.09

$^{13}C$ NMR ($D_2O$): □ 179.4, 174.7, 65.6, 62.2, 59.3, 54.4, 52.3, 50.8, 43.3, 42.2, 32.2, 31.9, 31.1, 30.0, 26.1, 23.3 ppm

EXAMPLE 22

Preparation of 3S, 4aR, 6S, 8aR 6-((3R)-3-(Carboxylic acid)-(5R)-5-hyroxypiperidinyl)-1, 2, 3, 4, 4a, 5, 6, 7, 8, 8a-decahydroisoquinoline-3-carboxylic Acid

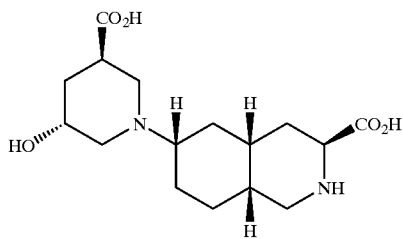

A. Preparation of 3S, 4aR, 6S, 8aR Ethyl 6-((3R)-(Ethoxycarbonyl)-(5R)-5-benzoyloxypiperidinyl)-2-methoxycarbonyl-1,2,3,4,4a,5,6,7,8,8a-decahydroisoquinoline-3-carboxylate A solution of 3S, 4aR, 6S, 8aR ethyl 6-((3R)(ethoxycarbonyl)-(5S)-5-hydroxypiperidinyl)-2-methoxycarbonyl-1,2,3,4,4a,5,6,7,8,8a-decahydroisoquinoline-3-carboxylate (2.5 g, 5.68 mmol), the compound descnibed in Step B of Example 19, was subjected to the reaction described in Step A of Example 21 above to provide the titled intermediate (1.89 g, 61%):

MS(m/e): 545.2 (M⁺)

Calculated for $C_{29}H_{40}N_2O_8$: Theory: C, 63.95; H, 7.40; N, 5.14. Found: C, 63.98; H, 7.34; N, 5.11

B. Preparation of 3S, 4aR, 6S, 8aR 6-((3R)₃-(Carboxylic acid)-(SR)-5-hydroxypiperidinyl)-1,2, 3, 4, 4a, 5, 6, 7, 8, 8a-decahydroisoquinoline-3-carboxylic Acid Acid hydrolysis of the compound from Step A above, using the procedure described for the preparation of the compound in Step B of Example 21, provided the title compound as a white solid:

MS(m/e): 327.3 (M⁺)

Calculated for $C_{16}H_{26}N_2O_5 \cdot 0.75H_2O$: Theory: C, 56.54; H, 8.16; N, 8.24.

Found: C, 56.53; H. 8.09; N, 8.20

$^{13}C$ NMR ($D_2O$): □ 179.3, 174.7, 66.0, 62.6, 54.4, 52.4, 43.6, 42.2, 32.2, 31.8, 31.0, 30.1, 27.5, 26.1, 25.9, 21.0 ppm

EXAMPLE 23

Preparation of 3S, 4aR, 6S, 8aR 6-((3S}3-(Carboxylic acid)-(5S)-5-fluoropiperidinyl)-1, 2, 3, 4, 4a, 5, 6, 7, 8, 8a-decahydroisoquinoline-3-carboxylic Acid

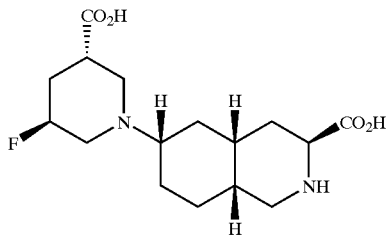

A. Preparation of 3S, 4aR, 6S, 8aR Ethyl 6-((3S)-(Ethoxycarbonyl)-(5S)-5-fluoropiperidinyl)-2-methoxycarbonyl-1,2,3,4,4a,5,6,7,8,8a-decahydroisoquinoline-3-carboxylate To a solution of the compound prepared in Step A of Example 20 (204 mg, 0.46 mmol) cooled to −78° C. in $CH_2Cl_2$ (5 mL) was added diethylaminosulfur trifluoride (92 □L, 0.69 mmol). The reaction was warmed to room temperature, stirred for 48 h, quenched with MeOH, then concentrated in vacuo. The residue was partitioned between 3:1 $CHCl_3/IPA$ and saturated aqueous $NaHCO_3$, extracted with $CHCl_3/IPA$, washed with saturated aqueous NaCl, dried ($MgSO_4$), and concentrated. Chromatography (stepwise gradient: hexane-75% EtOAc/hexane) provided the title compound (147 mg, 72%):

MS(m/e): 444.3 (M+)

Calculated for $C_{22}H_{35}FN_2O_6$: Theory: C, 59.71; H, 7.97; N, 6.33. Found: C, 60.12; H, 7.99; N, 6.48

B. Preparation of 3S, 4aR, 6S, 8aR 6-((3S}3-(Carboxylic acid)-(5S)-5-fluoropiperidinyl)-1,2,3,4,4a,5,6,7,8,8a-decahydroisoquinoline-3-carboxylic Acid Acid hydrolysis of the compound from Step A above, using the procedure described) for the preparation of the compound in Step B of Example 21, provided the title compound as a white solid:

MS(m/e): 329.0(M⁺)

HRMS (m/z): [M+H]⁺ calcd for $C_{16}H_{25}FN_2O_4$, 329.1877; found 329.1894

$^{13}C$ NMR ($D_2O$): □ 180.7, 174.7, 87.0 (d, $J_{C-F}$=171.2 Hz), 81.1 (d, $J_{C-F}$=170.5 Hz), 69.6 (d, $J_{C-F}$=207.9 Hz), 65.9, 54.4, 52.8, 49.7, 42.2, 32.2, 31.9, 30.1, 25.5, 23.3, 22.0 ppm

EXAMPLE 24

Preparation of 3S, 4aR, 6S, 8aR 6-((3R)-3-(Carboxylic acid)-(5S)-5-fluoropiperidinyl)-1, 2, 3, 4, 4a, 5, 6, 7, 8, 8a-decahydroisoquinoline-3-carboxylic Acid

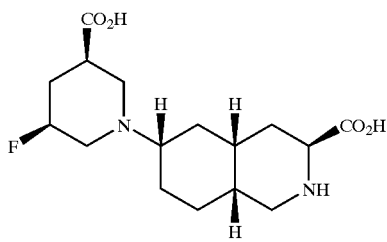

A. Preparation of 3S, 4aR, 6S, 8aR Ethyl 6-((3R)-(Ethoxycarbonyl)-(5S)-5-fluoropiperidinyl)-2-methoxycarbonyl-1,2,3,4,4a,5,6,7,8,8a-decahydroisoquinoline-103-carboxylate To a solution of 3S, 4aR, 6S, 8aR ethyl 6-((3R)-(ethoxycarbonyl)(5R)-5-benzoyloxypiperidinyl)-2-methoxycarbonyl-1,2,3,4,4a,5,6,7,8,8a-decahydroisoquinoline-3-carboxylate (1.2 g, 2.17 mmol), the compound described in Step A of Example 22, dissolved in EtOH (50 mL) was added $H_2SO_4$ (0.69 g, 6.51 mmol). The reaction was heated at 80° C. for 72 h, then concentrated in vacuo. The residue was partitioned between 3:1 $CHCl_3$/IPA and 1 N NaOH, extracted with $CHCl_3$/IPA, washed with saturated aqueous NaCl, dried ($MgSO_4$), and concentrated. Chromatography (Stepwise gradient: $CH_2Cl_2$-30% MeOH/$CH_2Cl_2$) provided the N-methyl carbamate diethyl ester intermediate (0.38 g, 40%), which was subjected to the DAST fluorination reaction as in the preparation of the compound described in Step A of Example 23 above, providing the title compound in 85% yield:

MS(m/e): 443.2($M^+$)

Calculated for $C_{22}H_{35}FN_2O_6 0.25H_2O$: Theory: C, 59.11; H, 8.00; N, 6.27. Found. C, 58.76; H. 7.54; N, 6.14

B. Preparation of 3S, 4aR, 6S, 8aR 6((3R)-3-(Carboxylic acid)-(S)$_5$-fluoropiperidinyl)-1,2,3,4,4a,5,6,7,8,8a-decahydroisoquinoline-3-carboxylic Acid Acid hydrolysis of the compound from Step A above, using the procedure described for the preparation of the compound in Step B of Example 21, provided the title compound as a white solid:

MS(m/e): 329.2 ($M^+$)

Calculated for $C_{16}H_{25}FN_2O 0.75H_2O$: Theory: C, 56.21; H, 7.81; N, 8.19.

Found: C, 56.03; H, 7.50; N, 7.98

EXAMPLE 25

Preparation of 3S, 4aR, 6S, 8aR 6((3R)-3-(Carboxylic acid)-(5R)-5-fluoropiperidinyl)-1, 2, 3, 4, 4a, 5, 6, 7, 8, 8a decahydroisoquinoline-3-carboxylic Acid

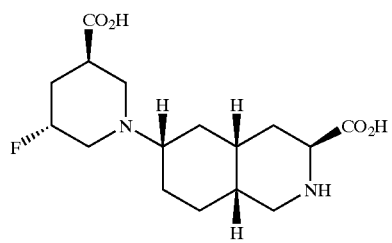

A. Preparation of 3S, 4aR, 6S, 8aR Ethyl 6-((3R)(Ethoxycarbonyl)-(5R)-5-fluoropiperidinyl)-2-methoxycarbonyl-1,2,3,4,4a,5,6,7,8,8a-decahydroisoquinoline-3-carboxylate The compound prepared in Step B of Example 19, 3S, 4aR, 6S, 8aR ethyl 6-((3R)$_7$-(ethoxycarbonyl)-(4S)-5-hydroxypiperidinyl)-2-methoxycarbonyl-1, 2, 3, 4, 4a, 5, 6, 7, 8, 8a-decahydroisoquinoline-3-carboxylate, was subjected to the DAST fluorination reaction described in the preparation of the compound described in Step A of Example 23 above to provide the title compound in 68% yield:

MS(m/e): 444.3 ($M^+$)

Calculated for $C_{22}H_{35}FN_2O_6 0.25H_2O$: Theory: C, 59.11; H, 8.01; N, 6.27. Found: C, 59.05; H, 7.85; N, 6.37

B. Preparation of 3S, 4aR, 6S, 8aR 6-((3R)-3-(Carboxylic acid)(5R)-5-fluoropiperidinyl)-1,2, 3, 4, 4a, 5, 6, 7, 8, 8a-decahydroisoquinoline-3-carboxylic Acid Acid hydrolysis of the compound from Step A above, using the procedure described for the preparation of the compound in Step B of Example 21, provided the title compound as a white solid:

MS(m/e): 329.3 ($M^+$)

HRMS (m/z): $[M+H]^+$ calcd for $C_{16}H_{25}FN_2O$, 329.1877; found 329.1903

$^{13}C$ NMR ($D_2O$): □174.7, 87.0 (d, $J_{C-F}$=173.2 Hz), 81.2 (d, $J_{C-F}$=170.6 Hz), 72.5 (d, $J_{C-F}$=228.2 Hz), 65.9, 54.4, 52.9, 50.4, 42.2, 32.2, 31.8, 30.1, 26.1, 25.9, 20.2 ppm

EXAMPLE 26

Preparation of 3S, 4aR, 6S, 8aR 6-((3S)$_3$-(Carboxylic acid)-5-oxopiperidinyl)-1, 2, 3, 4, 4a, 5, 6, 7, 8, 8a-decahydroisoquinoline-3-carboxylic Acid

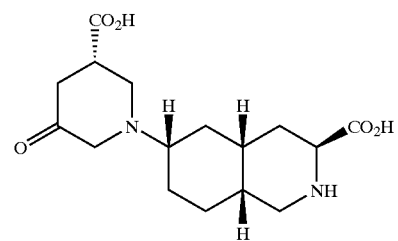

A. Preparation of 3S, 4aR, 6S, 8aR Ethyl 6-((3S)-(Ethoxycarbonyl)-5-oxopiperidinyl)-2-methoxycarbonyl-1, 2,3,4,4a,5,6,7,8,8a-decahydroisoquinoline-3-carboxylate A solution of DMSO (0.20 mL, 2.8 mmol) was cooled to −78° C. in $CH_2Cl_2$ (10 mL) and charged with $(COCl)_2$ (0.13 mL, 1.4 mmol). The mixture was stirred for 5 min, then 3S, 4aR, 6S, 8a ethyl 6(3S)-(ethoxycarbonyl)(5R)-5-hydroxypiperidinyl)-2-methoxycarbonyl-1,2,3,4,4a,5,6,7,8, 8a-decahydroisoquinoline-3-carboxylate (0.50 g, 1.1 mmol), the compound described in Step A of Example 20 above, dissolved in $CH_2Cl_2$ (10 mL) was added. After 1 h, triethylamine (0.80 mL, 5.6 mmol) was added and the reaction was warmed to room temperature overnight. The mixture was partitioned between $CH_2Cl_2$ and saturated aqueous $NaHCO_3$, extracted with $CH_2Cl_2$, washed with saturated aqueous NaCl, dried (MgSO4), and concentrated. Chromatography (stepwise gradient: $CH_2Cl_2$-10% EtOH/$CH_2Cl_2$) provided the title compound (0.47 g, 98%):

MS(m/e): 439.3 ($M^+$)

Calculated for $C_{22}H_{34}N_2O_7 . 0.25H_2O$: Theory: C, 59.65; 7.85; N, 6.32.

Found: C, 59.32; H. 7.55; N, 6.32

B. Preparation of 3S, 4aR, 6S, 8aR 6-((3S)-3-(carboxylic acid)-5-oxopiperidinyl)-1, 2, 3, 4, 4a, 5, 6, 7, 8, 8a-decahydroisoquinoline-3-carboxylic Acid Acid hydrolysis of the compound from Step A above, using the procedure described for the preparation of the compound in Step B of Example 21, provided the tide compound as a white solid:

MS(m/e): 325.4($M^+$)

Calculated for $C_{16}H_{24}N_2O_5 . 0.5H_2O$: Theory: C, 57.65; H. 7.56; N, 8.40.

Found: C, 57.79; H, 7.42; N, 8.56

EXAMPLE 27

Preparation of 3S, 4aR, 6S, 8aR 6-((3R)-3-(Carboxylic acid)-5-oxopiperidinyl)-1, 2, 3, 4, 4a, 5, 6, 7, 8, 8a-decahydroisoquinoline-3-carboxylic Acid

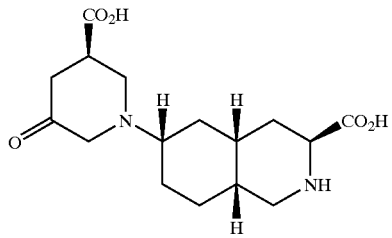

A. Preparation of 3S, 4aR, 6S, 8aR Ethyl 6-((3R)-(Ethoxycarbonyl)-5-oxopiperidinyl)-2-methoxycarbonyl-1,2,3,4,4a,5,6,7,8,8a-decahydroisoquinoline-3-carboxylate A solution of DMSO (0.75 mL, 10.5 mmol) was cooled to −78° C. in $CH_2Cl_2$ (20 mL) and charged with $(COCl)_2$ (0.43 mL, 5.0 mmol). The mixture was stirred for 5 min, then 3S, 4aR, 6S, 8aR ethyl 6-((3R)-(ethoxycarbonyl)-(5R)-hydroxypiperidinyl)-2-methoxycarbonyl-1,2,3,4,4a,5,6,7,8,8a-decahydroisoquinoline-3-carboxylate (1.85 g, 4.2 mmol), the compound described in Step B of Example 19 above, dissolved in $CH_2Cl_2$ (25 mL) was added. After 0.75 h, triethylamine (2.94 mL, 20.9 mmol) was added and the reaction was warmed to room temperature overnight. The mixture was partitioned between $CH_2Cl_2$ and saturated aqueous $NaHCO_3$, extracted with $CH_2Cl_2$, washed with saturated aqueous NaCl, dried ($MgSO_4$), and concentrated. Chromatography (stepwise gradient: $CH_2Cl_2$-10% EtOH/$CH_2Cl_2$) provided the title compound (1.03 g, 60%):

MS(m/e): 439.3 ($M^+$)

Calculated for $C_{22}H_{34}N_2O_7.0.25H_2O$: Theory: C, 59.65; H 7.85; N, 6.32. Found: C, 59.45; H. 7.57; N, 6.43

B. Preparation of 3S, 4aR, 6S, 8aR 6-((3R)₃-(Carboxylic acid)₅-oxopiperidinyl)-1, 2, 3, 4, 4a, 5, 6, 7, 8, 8-decahydroisoquinoline-3-carboxylic Acid Acid hydrolysis of the compound from Step A above, using the procedure described for the preparation of the compound in Step B of Example 21, provided the title compound as a white solid:

MS(m/e): 323.4 ($M^-$)

Calculated for $C_{16}H_{24}N_2O_5$: Theory: C, 59.24; H, 7.46; N, 8.64. Found: C, 58.87; H, 7.37; N, 8.85

EXAMPLE 28

Preparation of 3S, 4aR, 6S, 8aR 6-((3S)-3-(Carboxylic acid) 5,5-difluoropiperidinyl)-1, 2, 3, 4, 4a, 5, 6, 7, 8, 8-decahydroisoquinoline-3-carboxylic Acid

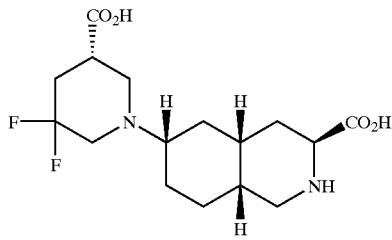

A. Preparation of 3S, 4aR, 6S, 8aR Ethyl 6((3S)(Ethoxycarbonyl)-5,5-difluoropiperidinyl)-2-methoxycarbonyl-1,2,3,4,4a,5,6,7,8,8a-decahydroisoquinoline-3-carboxylate To a solution of 3S, 4aR, 6S, 8aR ethyl 6-((3S)-(ethoxycarbonyl)-5-oxopiperidinyl)₂-methoxycarbonyl-1,2,3,4,4a,5,6,7,8,8a-decahydroisoquinoline-3-carboxylate (520 mg, 1.2 mmol), the compound described in Step A of Example 26 cooled to −78° C. in $CH_2Cl_2$ (15 mL) was added diethylaminosulfur trifluoride (400 □L, 2.8 mmol). The reaction was warmed to room temperature, stirred for 48 h, quenched with EtOH, then concentrated in vacuo. The residue was partitioned between $CH_2Cl_2$ and saturated aqueous $NaHCO_3$, extracted with $CH_2Cl_2$, washed with saturated aqueous NaCl, dried ($MgSO_4$), and concentrated. Chromatography (Stepwise gradient: hexane-50% EtOAc/hexane) provided the title compound (281 mg, 51%):

MS(m/e): 461.2 ($M^+$)

Calculated for $C_{22}H_{34}F_2N_2O_6.0.25H_2O$: Theory: C, 56.83; H, 7.48; N, 6.02. Found: C, 56.78; H, 7.09; N, 6.25

B. Preparation of 3S, 4aR, 6S, 8aR 6-((3S)-3-(Carboxylic acid)-5,5-difluoropiperidinyl)-1,2, 3, 4, 4a, 5, 6, 7, 8, 8a-decahydroisoquinoline-3-carboxylic Acid Acid hydrolysis of the compound from Step A above, using the procedure described for the preparation of the compound in Step B of Example 21, provided the title compound as a white solid:

MS(m/e): 347.2 ($M^+$)

Calculated for $C_{16}H_{24}F_2N_2O_5.0.75$ $H_2O$: Theory: C, 53.40; H,7.14; N, 7.78. Found: C, 53.19; H, 7.01; N, 7.47

$^{13}C$ NMR ($D_2O$): □177.0, 174.7, 119.4(d, $J_{C-F}$=243.9 Hz),66.6, 54.4, 52.1 (d, $J_{C-F}$=30.6 Hz), 50.1, 42.1, 38.6, 34.0 (d, $J_{C-F}$=23.5 Hz), 32.3, 31.9, 30.0, 26.1, 24.8, 21.5 ppm

EXAMPLE 29

Preparation of 3S, 4aR, 6S, 8aR 6-((3R)-3-(Carboxylic acid)-5,5-difluoropiperidinyl)-1, 2, 3, 4, 4a, 5, 6, 7, 8, 8a-decahydroisoquinoline-3-carboxylic Acid

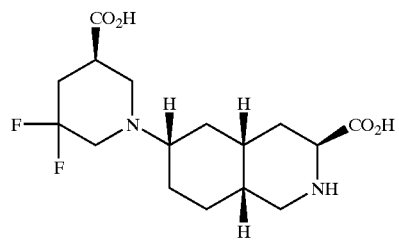

A. Preparation of 3S, 4aR, 6S, 8aR Ethyl 6-((3R)-(Ethoxycarbonyl)-5,5-difluoropiperidinyl)-2-methoxycarbonyl-1,2,3,4,4a,5,6,7,8,8a-decahydroisoquinoline-3-carboxylate The title compound was prepared from the compound described in Step A of Example 27 in the manner described for the preparation of the compound described in Step A of

EXAMPLE 28

MS(m/e): 461.4(M+)

Calculated for $C_{22}H_3F_2O_6 \cdot 0.25H_2O$: Theory. C, 56.83; H, 7.48; N, 6.02. Found: C, 56.79; H, 7.16; N, 6.08.

B. Preparation of 3S, 4aR, 6S, 8aR 6-((3R)$_3$-(Carboxylic acid)-5,5-difluoropiperidinyl)-1,2,3,4,4a,5,6,7,8,8a-decahydroisoquinoline-3-carboxylic Acid Acid hydrolysis of the compound from Step A above, using the procedure described for the preparation of the compound in Step B of Example 21, provided the title compound as a white solid:

MS(m/e): 347.2(M+)

Calculated for $C_{16}H_{24}F_2N_2O_4 \cdot 1.0H_2O$: Theory: C, 52.74; H, 7.19; N, 7.69. Found: C, 52.97; H, 7.02; N, 7.42

$^{13}C$ NMR (D$_2$O): □177.0, 174.6, 119.4 (d, $J^{C-F}$=243.2 Hz), 66.5, 54.4, 51.8 (d, $J_{C-F}$=33.9 Hz), 50.3, 42.1, 38.6, 34.0 (d, $J_{C-F}$=23.2 Hz), 32.3, 31.8, 30.0, 26.0, 25.6, 21.0 ppm

EXAMPLE 30

Preparation of 3S, 4aR, 6S, 8aR 6(3S)-3-carboxylic acid)-(5S)-5-(5-phenyltetrazol-2-yl)piperidinyl)-1,2, 3, 4, 4a, 5, 6, 7, 8, 8a-decahydroisoquinoline-3-carboxylic Acid

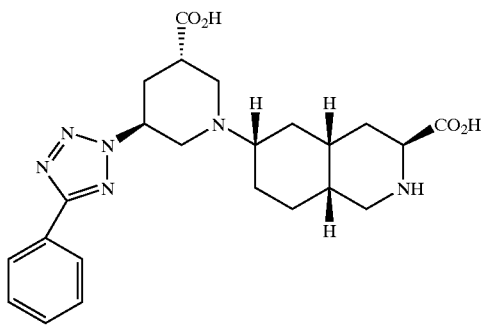

A. Preparation of 3S, 4aR, 6S, 8aR Ethyl 6-((3S)-(Ethoxycarbonyl)-(5S)-5-(5-phenyltetrazol-2-yl)piperidinyl)$_2$-methoxycarbonyl-1,2,3,4,4a,5,6,7,8,8a-decahydroisoquinoline-3-carboxylate A solution of 3S, 4aR, 6S, 8aR ethyl 6((3S)-(ethoxycarbonyl)-(5R)-5-hydroxypiperdinyl)-2-methoxycarbonyl-1,2,3,4,4a,5,6,7,8,8a-decahydroisoquinoline-3-carboxylate (0.59 g, 1.3 mmol), the compound described in Step A of Example 20 was cooled to 0° C. in THF (15 mL). Triphenylphosphine (1.4 g, 5.3 mmol), 5-phenyltetrazole (0.78 g, 5.3 mmol), and diethyl azodicarboxylate (0.68 g, 4.68 mmol) were added. After stirring at room temperature for 72 h, the reaction mixture was loaded onto a 5 g SCX Mega Bond Elut SPE cartridge (Varian Sample Preparation Products) and eluted with EtOH, followed by CH$_2$Cl$_2$. The product was removed with 2 M NH$_3$/EtOH, and the solution was concentrated then chromatographed (Stepwise gradient: hexane-50% EtOAc/hexane), to provide the title compound (0.39 g, 53%):

MS(m/e): 569.3 (M+)

Calculated for $C_{29}H_{40}N_6O_6$: Theory: C, 61.25; H, 7.09; N, 14.78. Found: C, 61.41; H, 7.07; N, 14.52

B. Preparation of 3S, 4aR, 6S, 8aR 6-((3S)-3-(Carboxylic acid)-(5S)-5-5-phenyltetrazol-2-yl)piperidinyl)-1,2,3,4,4a,5,6,7,8,8a-decahydroisoquinoline-3-carboxylic Acid Acid hydrolysis of the compound from Step A above, using the procedure described for the preparation of the compound in Step B of Example 21, provided the title compound as a white solid:

MS(m/e): 453.3 (M+)

HRMS (m/z): [M+H]+ calcd for $C_{23}H_{31}N_6O_4$, 455.2407; found 455.2433

EXAMPLE 31

Preparation of 3S, 4aR, 6S, 8aR 6((3R)-3-(Carboxylic acid)-(5R)-5-(5-phenyl-tetrazol-2-yl)piperidinyl)-1,2,3,4,4a,5,6,7,8,8a-decahydroisoquinoline-3-carboxylic Acid

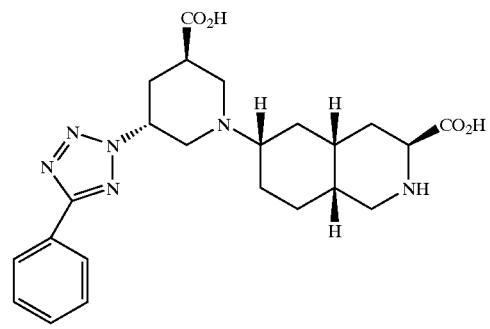

The title compound was prepared in the same two Step sequence described for the preparation of the compound in Step B of Example 30, starting with the compound described in Step B of Example 19:

MS(m/e): 453.2 (M+)

HRMS (m/z): [M+H] calcd for $C_{23}H_{31}N_6O_4$, 455.2407; found 455.2437

EXAMPLE 32

Preparation of 3S, 4aR, 6S, 8aR 6-((3R)-3-(Carboxylic acid)-(5R5-(5-phenyl-tetrazol-2-yl)piperidinyl-1,2,3,4,4a,5,6,7,8,8a-decahydroisoquinoline-3-carboxylic Acid

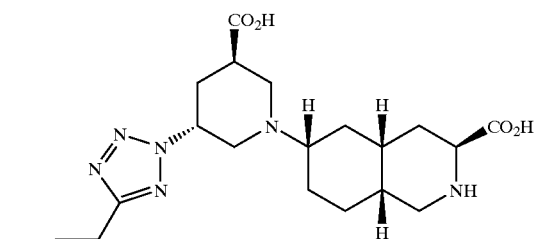

The title compound was prepared in the same two Step sequence described for the preparation of the compound in Step B of Example 30, starting with the compound described in Step B of Example 19, and using 5-propyltetrazole:

MS (m/e): 421.4 (M+)

HRMS (miz): [M+H]+calcd for $C_{20}H_{33}N_6O_4$, 421.2563; found 421.2588

EXAMPLE 33

Preparation of 3S, 4aR, 6S, 8aR 6-(((2S)-2-(Carboxylic acid)-pyrrolidinylmethyl-1,2,3,4,4a,5,6,7,8,8a-decahydroisoquinoline-3-carboxylic Acid

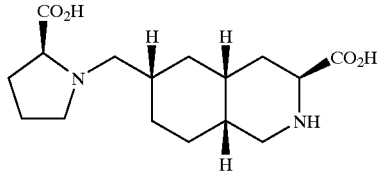

A. Preparation of 3S, 4aR, 6S, 8aR Ethyl 6-(((2S)-2-(tert-Butoxycarbonyl) pyrrolidinylmethyl)$_2$-methoxycarbonyl-1,2,3,4,4a,5,6,7,8,8a-decahydroisoquinoline-3-carboxylate A mixture of L-proline tert-butyl ester (0.44 g, 2.54 mmol), 3S, 4aR, 6S, 8aR ethyl6-formyl-2-methoxycarbonyl-decahydroisoquinoline-3-carboxylate (prepared by one of ordinary skill in the art following the procedures as disclosed in U.S. Pat. No. 5,670,516) (0.75 g, 2.52 mmol), NaBH(OAc)$_3$ (0.75 g, 3.53 mmol), and HOAc (0.15 mL, 2.53 mmol) was stirred at room temperature in TBF (15 mL) for 18 h. The reaction mixture was partitioned between 3:1 CHCl$_3$/IPA and saturated aqueous NaHCO$_3$, extracted with CHCl$_{31}$IPA, washed with saturated aqueous NaCl, dried (MgSO$_4$), and concentrated. Chromatography (75% EtOAc/hexane) provided the title compound (0.73 g, 64%):

MS(m/e): 453.3 (M$^+$)

Calculated for C$_{24}$H$_{40}$N$_2$O$_6$: Theory: C, 63.69; H, 8.91; N, 6.19. Found: C, 63.41; H, 8.83; N, 6.31

B. Preparation of 3S, 4aR, 6S, 8aR 6-(((2S)-2-(Carboxylic acid)-pyrrolidinylmethyl-1, 2, 3, 4, 4a, 5, 6, 7, 8, 8a-decahydroisoquinoline-3-carboxylic Acid A solution of the compound from Step A above (1.35 g, 2.98 mmol) dissolved in 5 N aqueous HCl (20 mL) was heated at 100° C. for 48 h. The reaction mixture was cooled to room temperature and concentrated in vacuo. The resulting crude foam was dissolved in H$_2$O (75 mL) and stirred in the presence of Dowex 50×8 (100–200) ion-exchange resin (10 g) for 2 h. The resin was filtered, washed sequentially with 1:1 THF/H$_2$O and H$_2$O, then stirred in the presence of 10% pyridine/H$_2$O for 2 h. After filtration, the resin was washed with H$_2$O, and the filtrate was concentrated in vacuo to provide the title compound (0.78 g, 84%) as a white foam:

MS(m/e): 311.3 (M$^+$)

Calculated for C$_{16}$H$_{26}$N$_2$O$_4$.1.5H$_2$O: Theory: C, 57.00; H, 8.66; N, 8.30.

Found: C, 57.03; H, 8.48; N, 8.18.

$^{13}$C NMR (D$_2$O): δ 177.5, 176.1, 70.5, 62.5, 56.1, 53.1, 43.3, 35.5, 33.9, 33.2, 32.3, 32.0, 29.9, 25.1, 23.8 ppm.

EXAMPLE 34

Preparation of 3S, 4aR, 6S, 8aR 6-(((2S)-2-(Carboxylic acid)-(4R)-4-hydroxypyrrolidinylmethyl-1,2,3,4,4a,5,6,7,8,8a-decahydroisoquinoline-3-carboxylic Acid

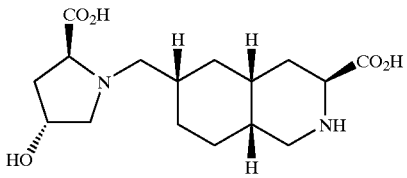

A. Preparation of 3S, 4aR, 6S, 8aR Ethyl 6-(((2S)-2-(Ethoxycarbonyl)-(4R)-4-hydroxypyrrolidinylmethyl)-2-methoxycarbonyl-1,2,3,4,4a,5,6,7,8,8a-decahydroisoquinoline-3-carboxylate A mixture of 4-hydroxy-L-proline ethyl ester (0.40 g, 2.53 mmol), 3S, 4aR, 6S, 8aR ethyl-6-formyl-2-methoxycarbonyl-decahydroisoquinoline-3-carboxylate (prepared by one of ordinary skill in the art following the procedures as disclosed in U.S. Pat. No. 5,670,516) (0.75 g, 2.52 mmol), NaBH(OAc)$_3$ (0.75 g, 3.53 mmol), and HOAc (0.15 mL, 2.53 mmol) was stirred at room temperature in THF (15 mL) for 18 h. The reaction mixture was partitioned between 3:1 CHCl$_3$/IPA and saturated aqueous NaHCO$_3$, extracted with CHCl$_3$/IPA, washed with saturated aqueous NaCl, dried (MgSO$_4$), and concentrated. Chromatography (75% EtOAc/hexane) provided the title compound (0.68 g, 61%):

MS(m/e): 441.3 (M$^+$)

B. Preparation of 3S, 4aR, 6S, 8aR Ethyl 6-(((2S)-2-(Ethoxycarbonyl)-(4R)-4-hydroxypyrrolidinylmethyl)-1,2,3,4,4a,5,6,7,8,8a-decahydroisoquinoline-3-carboxylate A mixture of the compound prepared in Step A above (0.63 g, 1.43 mmol) and iodotrimethylsilane (1.0 mL, 7.15 mmol), was stirred at 45° C. in CH$_2$Cl$_2$ (10 mL) for 3 h. The reaction mixture was quenched by the addition of saturated aqueous NaHCO3 and extracted with CH$_2$Cl$_2$. The combined organics were washed with saturated aqueous NaCl, dried (MgSO$_4$), and concentrated to provide the title compound (0.42 g, 77%).

C. Preparation of 3S, 4aR, 6S, 8aR 6-(((2S)-2-(Carboxylic acid)-(4R)$_4$-hydroxypyrrolidinylmethyl-1,2,3,4,4a,5,6,7,8,8a-decahydroisoquinoline-3-carboxylic Acid A solution of the compound from Step B above (0.42 g, 1.10 mmol) dissolved in 1:1 1 N aqueous NaOH/EtOH (5 mL) was heated at 50° C. for 4 h. The reaction mixture was cooled to room temperature, the pH of the reaction was adjusted to ~4 with 1 N aqueous HCl, and the reaction was concentrated in vacuo. The resulting crude foam was dissolved in H$_2$O (75 mL) and stired in the presence of Dowex 50×8 (100–200) ion-exchange resin (10 g) for 2 h. The resin was filtered, washed sequentially with 1:1 THF/H$_2$O and H$_2$O, then stirred in the presence of 10% pyridine/H$_2$O for 2 h. After filtration, the resin was washed with H$_2$O, and the filtrate was concentrated in vacuo to provide the title compound (0.29 g, 81%) as a white foam:

MS(m/e): 311.3 (M$^+$)

Calculated for C$_{16}$H$_{26}$N$_2$O$_5$.2.0H$_2$O: Theory: C, 53.03; H, 8.34; N, 7.73.

Found: C, 52.88; H, 8.21; N, 7.56

$^{13}$C NMR (D$_2$O): δ 181.3, 178.7, 70.4, 69.7, 63.4, 62.2, 55.8, 43.6, 39.5, 37.1, 34.9, 33.7, 32.9, 30.4, 28.9, 26.4 ppm

EXAMPLE 35

To establish that the iGluR$_5$ receptor subtype is mediating a pharmacological response in a neurological disease or disorder, the binding affinity of the panel compounds to the iGluR$_5$ receptor is first measured using standard methods. For example, the activity of compounds acting at the iGluR$_5$ receptor can be determined by radiolabelled ligand binding studies at the cloned and expressed human iGluR5 receptor (Korczak et al., 1994, Recept Channels 3; 41–49), and by whole cell voltage clamp electrophysiological recordings of currents in acutely isolated rat dorsal root ganglion neurons (Bleakman et al., 1996, Mol. Pharmacol. 49; 581–585). The selectivity of compounds acting at the iGluR$_5$ receptor subtype can then be determined by comparing antagonist activity at the iGluR$_5$ receptor with antagonist activity at other AMPA and kainate receptors. Methods useful for such comparison studies include: receptor-ligand binding studies and whole-cell voltage clamp electrophysiological recordings of functional activity at human GluR$_1$, GluR$_2$, GluR$_3$ and GluR$_4$ receptors (Fletcher et al., 1995, Recept Channels 3; 21–31); receptor-ligand binding studies and whole-cell voltage clamp electrophysiological recordings of functional activity at human GluR$_6$ receptors (Hoo et al., Recept. Channels 2;327–338); and whole-cell voltage clamp electrophysiological recordings of functional activity at AMPA receptors in acutely isolated cerebellar Purkinje neurons (Bleakman et al., 1996, Mol. Pharmacol. 49; 581–585) and other tissues expressing AMPA receptors (Fletcher and Lodge, 1996, Pharmacol. Ther. 70; 65–89).

iGluR5 Antagonist Binding Affinity Profiles

Cell lines (HEK293 cells) stably transfected with human iGluR receptors are employed. Displacement of 3[H]AMPA by increasing concentrations of antagonist is measured on iGluR$_1$, iGluR$_2$, iGluR$_3$, and iGluR$_4$ expressing cells, while displacement of $^3$[H] kainate (KA) is measured on iGluR$_5$, iGluR$_6$, iGluR$_7$, and KA2-expressing cells. Estimated antagonist binding activity (K$_i$) in μM, for example, is determined for Compounds of Formula I. As an indicia of selectivity, the ratio of binding affinity to the iGluR$_2$ AMPA receptor subtype, versus the binding affinity to iGluR$_5$ kainate receptor subtype (K$_i$ at iGluR$_2$/K$_i$ at iGluR5) is also determined. The iGluR5 receptor antagonist compounds, as provided by the present invention, provide a K$_i$ at the iGluR$_5$ receptor subtype of less than 5000 μM, preferably less than 500 μM, even more preferably less than 50 μM, and most preferably less than 5 μM. The preferred selective iGluR5 receptor antagonists compounds, as provided by the present invention, display a greater binding affinity (lower K$_i$) for iGluR$_5$ than that for iGluR$_2$, preferably at least 10 fold greater for iGluR$_5$ than that for iGluR$_2$, and even more preferably at least 100 fold, and most preferably at least 1000 fold than that for iGluR$_2$.

EXAMPLE 36

The following animal model may be employed to determine the ability of each of the compounds of Formula I to inhibit protein extravasation, an exemplary functional assay of the neuronal mechanism of migraine.

Animal Model of Dural Protein Extravasation

Harlan Sprague-Dawley rats (225–325 g) or guinea pigs from Charles River Laboratories (225–325 g) are anesthetized with sodium pentobarbital intraperitoneally (65 mg/kg or 45 mg/kg respectively) and placed in a stereotaxic frame (David Kopf Instruments) with the incisor bar set at –3.5 mm for rats or –4.0 mm for guinea pigs. Following a midline sagital scalp incision, two pairs of bilateral holes are drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the tips (Rhodes Medical Systems, Inc.), are lowered through the holes in both hemispheres to a depth of 9 mm (rats) or 10.5 mm (guinea pigs) from dura.

The femoral vein is exposed and a dose of the test compound is injected intravenously (i.v.) at a dosing volume of 1 ml/kg or, in the alternative, test compound is administered orally (p.o) via gavage at a volume of 2.0 ml/kg. Approximately 7 minutes post i.v. injection, a 50 mg/kg dose of Evans Blue, a fluorescent dye, is also injected intravenously. The Evans Blue complexes with proteins in the blood and functions as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals are euthanized by exsanguination with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monchromator and a spectrophotometer is used to quantify the amount of Evans Blue dye in each sample. An excitation wavelength of approximately 535 nm is utilized and the emission intensity at 600 nm is determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion has an ipsilateral effect (i.e. occurs only on the side of the dura in which the trigeminal ganglion was stimulated). This allows the other (unstimulated) half of the dura to be used as a control. The ratio ("extravasation ratio") of the amount of extravasation in the dura from the stimulated side, over the amount of extravasation in the unstimulated side, is calculated. Control animals dosed with only with saline, yield an extravasation ratio of approximately 2.0 in rats and apprximately 1.8 in guinea pigs. In contrast, a compound that completely prevents the extravasation in the dura from the stimulated side would yield a ratio of approximately 1.0.

Dose-response curves are generated for each of the compounds of Formula I and the dose that inhibits the extravasation by 50% (ID$_{50}$) or 100% (ID$_{100}$) is approximated.

EXAMPLE 37

To demonstrate the utility of compounds of the present invention to treat pain or provide analgesic effects, several well known animal models may be employed. For example, international application WO 98/45270 describes the well known Formalin Test, which is described below:

Formalin Test

For example, male Sprague-Dawley rats (200–250 g; Charles River, Portage, Mich.) are housed in group cages and maintained in a constant temperature and a 12 hour light/12 hour dark cycle 4–7 days before studies are performed. Animals have free access to food and water at all times prior to the day of the experiment.

Drugs or vehicles are administered intraperitoneally (i.p.) or orally (p.o.) by gavage in a volume of about 1 ml/kg. The test is performed in custom made Plexiglas® boxes about 25×25×20 cm in size (according to Shibata et al., Pain 38;347–352, 1989, Wheeler-Aceto et al., Pain, 40; 229–238, 1990). A mirror placed at the back of the cage allows the unhindered observation of the formalin injected paw. Rats are acclimated individually in the cubicles at least 1 hour prior to the experiment. All testing is conducted between, for example, 08:00 and 14:00 h and the testing room temperature is maintained at about 21–23° C.

Test compounds are administered about 30 minutes prior to the formalin injection. Formalin (50 micoliters of a 5% solution in saline) is injected subcutaneously into the dorsal lateral surface of the right hind paw with a 27 gauge needle. Observation is started immediately after the formalin injection. Formalin-induced pain is quantified by recording, for example, in 5 minute intervals, the number of formalin injected pawlicking events and the number of seconds each licking event lasts. These recordings are made for about 50 minutes after the formalin injection.

Several different scoring parameters have been reported for the formalin test. The total time spent licking and biting the injected paw is demonstrated to be most relevant (Coderre et al.,*Eur. J. Neurosci.* 6; 1328–1334, 1993; Abbott et al., Pain, 60; 91–102, 1995) and may be chosen for the testing score. The early phase score is the sum of time spent licking, in seconds, from time 0 to 5 minutes. The late phase is scored in 5 minute blocks from 15 minutes to 40 minutes and is expressed accordingly or also by adding the total number of seconds spent licking from minute 15 to minute 40 of the observation period.

Data may be presented as means with standard errors of means (±SEM). Data may also be evaluated by one-way analysis of variance (ANOVA) and the appropriate contrasts analyzed by Dunnett "t" test for two sided comparisons. Differences are considered to be significant if, for example, the P-value is less than 0.05. Statistics may be determined at the 5 minute time point and at 5 minute intervals between 15 and 40 minutes. Where data are expressed as total amount of time spent licking in the late phase, statistics may be performed on the total time spent licking as well and may be indicated accordingly.

In addition to the Formalin Test, the well known Mouse Writhing Test, essentially as described in published International Application WO 00/028980, may also be employed to demonstrate the analgesic properties of compounds of the present invention.

Mouse Writhing Test

An accepted procedure for detecting and comparing the analgesic activity of different classes of analgesic drugs, for which there is a good correlation with human analgesic activity, is the prevention of acetic acid-induced writhing in mice. Mice are orally administered various doses of a test compound or placebo prior to testing. The mice are then injected intraperitoneally with acetic acid (0.55% solution, 10 mL/kg) five minutes prior to a designated observation period. Inhibition of writhing behavior is demonstrative of analgesic activity. Haubrich et al., "Pharmacology of pravadoline: a new analgesic agent", *The Journal of Pharmacology and Experimental Therapeutics*, 255 (1990) 511–522. For scoring purposes "writhe" is indicated by whole body stretching or contracting of the abdomen during an observation period beginning about five minutes after receiving the acetic acid.

$ED_{50}$ values, and their standard error of means (SEM) are determined using accepted numerical methods for all test compounds administered. For example, see R. E. Kirk (1982) "Experimental Design: Procedures for the behavioral sciences," 2nd ed. One method to establish the significance of the analgesic activity of a given test compound compared to that of another is to calculate the SEM values for each $ED_{50}$ value. If the SEM values do not overlap the line of addition, then the ED50 values are significantly different from the line of addition.

Yet another accepted animal model to demonstrate the ability of a particular compound to treat pain, or provide analgesic effects, is the well known Rat Model of Carrageenan-induced Thermal Hyperalgesia, also described in published International Application WO 00/028980.

Carrageenan-Induced Thermal Hyperalgesia in Rats

Another accepted method for detecting and comparing the analgesic activity of different classes of analgesic compounds for which there is good correlation with human analgesic activity is the reversal of carrageenan-induced thermal hyperalgesia in rats (Hargreaves et al. *Pain* 32:77–88, 1988).

Rats are administered a dose test compound or vehicle and then injected subcutaneously into one hindpaw, with carrageenan (1.5% w/v, 100 µl). The response to noxious thermal stimulus is determined two hours later using a commercially available thermal plantar device (Ugo Basil, Italy) according to established methods (Hargreaves et al. *Pain* 32:77–88, 1988). Briefly, animals are habituated to a plastic behavioral enclosure for 5 min. A heat source is positioned directly beneath a hindpaw and the time taken for hindpaw withdrawal monitored automatically. If the animal does not respond within 20 sec, the stimulus is automatically terminated to prevent tissue damage. Measurements for both the injured and contralateral (control) hindpaw are recorded. Thermal hyperalgesia is evidenced by a shorter response latency by the injured as compared to the control paw.

$ED_{50}$ values and their standard error of means (SEM) are determined using accepted numerical methods. For example, see R. E. Kirk (1982) "Experimental Design: Procedures for the behavioral sciences," 2nd ed.

What is claimed is:

1. A compound of the formula:

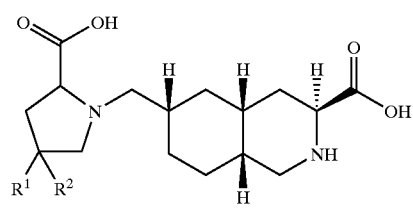

wherein, $R^1$ represents hydrogen, chlorine, bromine, iodine, fluorine, $SR^3$, or hydroxy;

$R^2$ represents hydrogen or fluorine, with the proviso that where $R^1$ is other than fluorine, then $R^2$ represents hydrogen; and $R^3$ represents tetrazole, substituted tetrazole, triazole, $(C_1-C_4)$alkyl, or $(C_1-C_4)$alkyl-$CO_2H$;

with the further proviso that where $R^1$ and $R^2$ each independently represent fluorine, the compound is of the formula or a pharmaceutically acceptable salt or prodrug thereof.

2. A compound of formula:

wherein,
- $R^2$ represents hydrogen or fluorine;
- $R^4$ represents hydrogen, chlorine, bromine, iodine, fluorine, $SR^7$, or hydroxy, with the proviso that where $R^4$ is other than fluorine, then $R^2$ represents hydrogen;
- $R^7$ represents tetrazole, substituted tetrazole, triazole, $(C_1-C_4)$alkyl, $(C_1-C_4)$alkyl-$CO_2R^8$; and
- $R^5$, $R^6$, and $R^8$ each independently represent hydrogen, $(C_1-C_{20})$alkyl, $(C_2-C_6)$alkenyl, $(C_1-C_6)$alkylaryl, $(C_1-C_6)$alkyl $(C_3-C_{10})$cycloalkyl, $(C_1-C_6)$alkyl-N,N—$C_1-C_6$ dialkylamine, $(C_1-C_6)$alkyl-pyrrolidine, $(C_1-C_6)$alkyl-piperidine, or $(C_1-C_6)$alkyl-morpholine, with the proviso that at least one of $R^5$, $R^6$, or $R^8$ is other than hydrogen;
- with the further proviso that where $R^2$ and $R^4$ each independently represent fluorine, then the compound is of the formula or a pharmaceutically acceptable salt thereof.

3. The compound according to claim 2 wherein $R^5$ represents hydrogen and $R^6$ represents $(C_1-C_{20})$alkyl.

4. The compound according to claim 3 wherein $R^6$ represents $(C_1-C_6)$alkyl.

5. The compound according to claim 2 wherein $R^5$ represents $(C_1-C_{20})$alkyl and R6 represents hydrogen.

6. The compound according to claim 5 wherein $R^5$ represents $(C_1-C_6)$alkyl.

7. The compound according to claim 2 wherein $R^5$ and $R^6$ each independently represent $(C_1-C_{20})$alkyl.

8. The compound according to claim 7 wherein $R^5$ and $R^6$ each independently represent $(C_1-C_6)$alkyl.

9. The compound according to claim 8 wherein $R^5$ and $R^6$ each independently represent ethyl.

10. A compound of the formula wherein,
- R9 represents hydrogen, chlorine, bromine, iodine, fluorine, hydroxy, tetrazole, or a group of the formula:

wherein X represents $(C_1-C_4)$alkyl or phenyl; and
- $R^{10}$ represents hydrogen or fluorine, with the proviso that where $R^9$ is other than fluorine, then $R^{10}$ represents hydrogen, or a pharmaceutically acceptable salt or prodrug thereof.

11. A compound of the formula wherein,
- $R^9$ represents hydrogen, chlorine, bromine, iodine, fluorine, hydroxy, tetrazole, or a group of the formula:

wherein X represents $(C_1-C_4)$alkyl or phenyl;
- $R^{10}$ represents hydrogen or fluorine, with the proviso that where $R^9$ is other than fluorine, then $R^{10}$ represents hydrogen,
- $R^{11}$ and $R^{12}$ each independently represent hydrogen, $(C_1-C_{20})$alkyl, $(C_2-C_6)$alkenyl, $(C_1-C_6)$alkylaryl, $(C_1-C_6)$alkyl$(C_3-C_{10})$cycloalkyl, $(C_1-C_6)$alkyl-N,N—$C_1-C_6$ dialkylamine, $(C_1-C_6)$alkyl-pyrrolidine, $(C_1-C_6)$alkyl-piperidine, or $(C_1-C_6)$alkyl-morpholine, with the proviso that at least one of $R^{11}$ or $R^{12}$ is other than hydrogen, or a pharmaceutically acceptable salt thereof.

12. The compound according to claim 11 wherein $R^{11}$ represents hydrogen and R12 represents $(C_1-C_{20})$alkyl.

13. The compound according to claim 12 wherein $R^{12}$ represents $(C_1-C_6)$alkyl.

14. The compound according to claim 11 wherein $R^{11}$ represents $(C_1-C_{20})$alkyl and R12 represents hydrogen.

15. The compound according to claim 14 wherein $R^{11}$ represents $(C_1-C_6)$alkyl.

16. The compound according to claim 11 wherein $R^{11}$ and $R^{12}$ each independently represent $(C_1-C_{20})$alkyl.

17. The compound according to claim 16 wherein $R^{11}$ and $R^{12}$ each independently represent $(C_1-C_6)$alkyl.

18. The compound according to claim 17 wherein $R^{11}$ and $R^{12}$ each independently represent ethyl.

19. A method of treating a neurological disorder or neurodegenerative disease which comprises administering to a patient in need thereof an effective amount of a compound according to claim 1.

20. The method according to claim 19 wherein the neurological disorder is migraine.

21. The method according to claim 19 wherein the neurological disorder is pain.

22. A pharmaceutical composition comprising an effective amount of a compound according to claim 1 in combination with a pharmaceutically acceptable carrier, diluent, or excipient.

23. A method of treating a neurological disorder or neurodegenerative disease which comprises administering to a patient in need thereof an effective amount of a compound according to claim 2.

24. A method of treating a neurological disorder or neurodegenerative disease which comprises administering to a patient in need thereof an effective amount of a compound according to claim 10.

25. A method of treating a neurological disorder or neurodegenerative disease which comprises administering to a patient in need thereof an effective amount of a compound according to claim 11.

26. A pharmaceutical composition comprising an effective amount of a compound according to claim 2 in combination with a pharmaceutically acceptable carrier, diluent, or excipient.

27. A pharmaceutical composition comprising an effective amount of a compound according to claim 10 in combination with a pharmaceutically acceptable carrier, diluent, or excipient.

28. A pharmaceutical composition comprising an effective amount of a compound according to claim 11 in combination with a pharmaceutically acceptable carrier, diluent, or excipient.

* * * * *